US012742759B2

(12) United States Patent
Hutter et al.

(10) Patent No.: US 12,742,759 B2
(45) Date of Patent: Sep. 22, 2026

(54) GAS DETECTOR DEVICES AND METHODS OF MAKING AND USE THEREOF

(71) Applicants: BOARD OF REGENTS, THE UNIVERSITY OF TEXAS SYSTEM, Austin, TX (US); INL—INTERNATIONAL IBERIAN NANOTECHNOLOGY LABORATORY, Braga (PT)

(72) Inventors: Tanya Hutter, Austin, TX (US); Vinaya Kumar Kadayra Basavarajappa, Braga (PT)

(73) Assignees: BOARD OF REGENTS, THE UNIVERSITY OF TEXAS SYSTEM, Austin, TX (US); INL—INTERNATIONAL IBERIAN NANOTECHNOLOGY LABORATORY, Braga (PT)

( * ) Notice: Subject to any disclaimer, the term of this patent is extended or adjusted under 35 U.S.C. 154(b) by 471 days.

(21) Appl. No.: 18/272,230

(22) PCT Filed: Jan. 13, 2022

(86) PCT No.: PCT/US2022/012259
§ 371 (c)(1),
(2) Date: Jul. 13, 2023

(87) PCT Pub. No.: WO2022/155293
PCT Pub. Date: Jul. 21, 2022

(65) Prior Publication Data

US 2024/0302340 A1 Sep. 12, 2024

Related U.S. Application Data

(60) Provisional application No. 63/137,910, filed on Jan. 15, 2021.

(51) Int. Cl.
*G01N 33/00* (2006.01)

(52) U.S. Cl.
CPC ..... *G01N 33/0047* (2013.01); *G01N 33/0013* (2013.01); *G01N 33/0073* (2013.01)

(58) Field of Classification Search
None
See application file for complete search history.

(56) References Cited

U.S. PATENT DOCUMENTS 3,164,718 A 1/1965 King
3,831,029 A 8/1974 Jones et al.
(Continued)

FOREIGN PATENT DOCUMENTS

CN 101442871 B 9/2013
DE 102004060103 A1 12/2005
(Continued)

OTHER PUBLICATIONS

International Search Report and Written Opinion received in PCT/US2022/012259 mailed Apr. 11, 2022.
(Continued)

*Primary Examiner* — Daniel S Larkin
(74) *Attorney, Agent, or Firm* — Meunier Carlin & Curfman LLC

(57) ABSTRACT

Disclosed herein are gas detector devices and methods of making and use thereof. The gas detector devices comprise: a temperature control layer; a grounded electrode; and a pyroelectric layer; the grounded electrode being disposed between the temperature control layer and the pyroelectric layer; and a detection electrode opposite and spaced apart from the pyroelectric layer defining an ionization zone therebetween. Disclosed herein are gas detection methods comprising: introducing a gas into the ionization zone; heating/cooling the temperature control layer to induce a
(Continued)

first potential in the pyroelectric layer sufficient to ionize a first gas component, thereby producing a first ion; detecting the first ion; subsequently, heating/cooling the temperature control layer to induce a second potential in the pyroelectric layer sufficient to ionize the first gas component and a second gas component, thereby producing the first ion and a second ion; and electrically detecting the first ion and the second ion.

17 Claims, 31 Drawing Sheets

(56) References Cited

U.S. PATENT DOCUMENTS

| | | | | |
|---|---|---|---|---|
| 3,930,157 | A | 12/1975 | Watton | |
| 4,008,444 | A | 2/1977 | Zar et al. | |
| 4,383,174 | A * | 5/1983 | Matsumura | H10N 15/10 250/338.3 |
| 4,671,852 | A | 6/1987 | Pyke | |
| 7,741,615 | B2 | 6/2010 | Putterman et al. | |
| 7,791,019 | B2 | 9/2010 | Beauchamp et al. | |
| 8,056,395 | B2 | 11/2011 | Oki | |
| 8,362,584 | B2 * | 1/2013 | Noda | G01J 5/068 257/295 |
| 9,140,610 | B2 * | 9/2015 | Noda | H10N 15/10 |
| 9,646,797 | B2 | 5/2017 | Einat | |
| 9,683,967 | B2 | 6/2017 | Lal et al. | |
| 9,685,295 | B2 | 6/2017 | King et al. | |
| 9,685,296 | B1 | 6/2017 | Hoff et al. | |
| 9,881,763 | B2 | 1/2018 | Ujimoto | |
| 10,431,412 | B2 | 10/2019 | Akinwande et al. | |
| 2008/0179514 | A1 | 7/2008 | Beauchamp et al. | |
| 2010/0065754 | A1 | 3/2010 | Bromberg et al. | |
| 2011/0024617 | A1 | 2/2011 | Neidholdt et al. | |
| 2011/0072887 | A1 | 3/2011 | Oki | |
| 2017/0133190 | A1 | 5/2017 | Ujimoto | |
| 2019/0094195 | A1 | 3/2019 | Gentner | |

FOREIGN PATENT DOCUMENTS

| | | | |
|---|---|---|---|
| DE | 102014207829 | A1 | 10/2015 |
| GB | 2330456 | A | 7/2002 |
| JP | 2000230859 | A | 8/2000 |
| WO | 2004048964 | A1 | 6/2004 |
| WO | 2009052176 | A1 | 4/2009 |
| WO | 2014124041 | A2 | 8/2014 |

OTHER PUBLICATIONS

Extended European Search Report mailed Nov. 11, 2024 in corresponding EP application 22740039.7 (9 pages).

Alimagham et al. "Mid-IR evanescent-field fiber sensor with enhanced sensitivity for volatile organic compounds." RSC advances 9, No. 37 (2019): 21186-21191.

Arab et al. "Initial results on electron beam generation using pyroelectric crystals." Proc. IPAC'10 (2010): 4384-4386.

Bamiedakis et al. "PCB-integrated optical waveguide sensors: an ammonia gas sensor." Journal of Lightwave Technology 31, No. 10 (2013): 1628-1635.

Danon. A Novel Compact Pyroelectric X-Ray and Neutron Source. No. DOE/ID/14596. Rensselaer Polytechnic Institute, 2007. 196 pages.

Fletcher et al. "Pyroelectric electron emission from nanometer-thick films of PbZrxTi1—xO3." Applied Physics Letters 102, No. 19 (2013): 192908.

Hopwood. "A microfabricated inductively coupled plasma generator." Journal of Microelectromechanical Systems 9, No. 3 (2000): 309-313.

Hutter et al. "Method for increasing reliability in gas detection based on indicator gradient in a sensor array." Sensors and Actuators B: Chemical 152, No. 1 (2011): 29-36.

Kukhtarev et al. "Generation of focused electron beam by pyroelectric and photogalvanic crystals." Journal of applied physics 96, No. 11 (2004): 6794-6798.

Longwitz et al. "Study of micro-glow discharges as ion sources for ion mobility spectrometry." Journal of Vacuum Science & Technology B: Microelectronics and Nanometer Structures Processing, Measurement, and Phenomena 21, No. 4 (2003): 1570-1573.

Marcus et al. "Formation of silicon tips with< 1 nm radius." Applied Physics Letters 56, No. 3 (1990): 236-238.

Modi et al. "Miniaturized gas ionization sensors using carbon nanotubes." Nature 424.6945 (2003): 171-174.

Neidholt et al. Compact Ambient Pressure Pyroelectric Ion Source for Mass Spectrometry, Analytical Chemistry, 2007, 79(10), 3945-3948.

Neidholt et al. Ionization Mechanism of the Ambient Pressure Pyroelectric Ion Source (Appis) and its Applications To Chemical Nerve Agent Detection, J Am Soc Mass Spectrom, 2009, 20, 2093-2099.

Ni et al. "Multi Kilovolt Lithium Niobate Pyroelectric Cantilever Switched Power Supply." In 2019 IEEE 32nd International Conference on Micro Electro Mechanical Systems (MEMS), pp. 970-973. IEEE, 2019.

Ou et al. "Design and Implementation of a Novel Multifunction and Frequency Tunable Ionizer." 2019 IEEE 4th International Future Energy Electronics Conference (IFEEC). IEEE, 2019. doi: 10.1109/IFEEC47410.2019.9014980.

She et al. "Comparative study of electron emission characteristics of silicon tip arrays with and without amorphous diamond coating." Journal of Vacuum Science & Technology B: Microelectronics and Nanometer Structures Processing, Measurement, and Phenomena 17, No. 2 (1999): 592-595.

Velasquez-Garcia et al. "CNT-based MEMS/NEMS gas ionizers for portable mass spectrometry applications." Journal of Microelectromechanical Systems 19, No. 3 (2010): 484-493.

Vinayakumar et al. "Enhanced lithium niobate pyroelectric ionizer for chip-scale ion mobility-based gas sensing." In 2016 IEEE Sensors, pp. 1-3. IEEE, 2016. doi: 10.1109/ICSENS.2016.7808451.

Yoon et al. "Fabrication of two types of micro ion sources for a micro time-of-flight mass spectrometer." Journal of Micromechanics and Microengineering 17, No. 8 (2007): 1542.

Yoon et al. "Test of hot electron emission for the micro mass spectrometer." In Design, Test, Integration, and Packaging of MEMS/MOEMS 2001, vol. 4408, pp. 360-367. International Society for Optics and Photonics, 2001.

International Preliminary Report on Patentability issued for Application No. PCT/US2022/012259, dated Jul. 27, 2023.

* cited by examiner 420
420
420
402
400
404

Wafer-2 Processing

Metal Pyroelectric Silicon Silicon oxide

SOI wafer

Oxide deposition on back side

Patterning silicon for metal deposition

Metal deposition

Deep reactive ion etching

GAS DETECTOR DEVICES AND METHODS OF MAKING AND USE THEREOF

CROSS-REFERENCE TO RELATED APPLICATIONS

This application is a U.S. National Stage application filed under 35 U.S.C. § 371 of PCT/US2022/012259 filed Jan. 13, 2022, which claims the benefit of priority to U.S. Provisional Application No. 63/137,910 filed Jan. 15, 2021, each of which is hereby incorporated herein by reference in its entirety.

BACKGROUND

Air pollution strongly affects physical and mental health. The first step towards controlling air quality is measuring and understanding the chemical components present at multiple locations. Performance, size, and cost of gas sensors play a key role in enabling air quality and toxic gas monitoring. Currently available small and portable/distributed technologies suffer from a variety of limitations, including high cost, low sensitivity, and/or inability to identify the detected gas molecules. Efficient, low-cost, chip-scale, miniature gas sensor for multi-gas detection are still needed. The devices and methods described herein address these and other needs.

SUMMARY

In accordance with the purposes of the disclosed device and methods, as embodied and broadly described herein, the disclosed subject matter relates to gas detector devices and methods of making and use thereof.

Disclosed herein are gas detector devices comprising: a temperature control layer; a grounded electrode disposed on the temperature control layer, wherein the grounded electrode is thermally conductive and is in thermal contact with the temperature control layer; a pyroelectric layer comprising a pyroelectric material, wherein the pyroelectric layer is disposed on the grounded electrode such that the grounded electrode is disposed between the temperature control layer and the pyroelectric layer, and wherein the pyroelectric layer is in thermal contact and electrical contact with the grounded electrode; and a detection electrode opposite and spaced apart from the pyroelectric layer by a distance, such that the detection electrode and the pyroelectric layer define an ionization zone between the detection electrode and the pyroelectric layer.

In some examples, the temperature control layer comprises a metallic resistive heating or cooling material, a ceramic heating or cooling material, a thermoelectric material, an induction heating or cooling material, an optical heating or cooling material, or a combination thereof. In some examples, the temperature control layer comprises a thermoelectric material. In some examples, the temperature control layer comprises a Peltier element.

In some examples, the grounded electrode comprises a transparent conducting oxide, a metal oxide, a conducting polymer, a carbon material, a metal, or a combination thereof.

In some examples, the pyroelectric material comprises lithium niobate ($LiNbO_3$), barium titanate ($BaTO_3$), lithium tantalate ($LiTaO_3$), lead zirconate titanate (PZT), cesium nitrate ($CsNO_3$), tourmaline, aluminum nitride (AlN), scandium doped aluminum nitride (ScAlN), potassium-sodium niobate (KNN), and combinations thereof. In some examples, the pyroelectric material comprises lithium niobate ($LiNbO_3$).

In some examples, the pyroelectric layer has a top surface and a bottom surface opposite and spaced apart from the top surface, wherein the top surface of the pyroelectric layer together with the patterned detection electrode defines the ionization zone, and wherein the top surface of the pyroelectric layer is textured. In some examples, the pyroelectric layer comprises a set of particles disposed on the top surface.

In some examples, the pyroelectric layer comprises a set of protrusions extending from the top surface. In some examples, the set of protrusions comprises a plurality of protrusions arranged in an ordered array on the top surface of the pyroelectric layer. In some examples, the set of protrusions extending from the top surface of the pyroelectric layer each has a longitudinal axis, a first surface, and a second surface opposite and axially spaced apart from the first surface, and wherein each of the set of protrusions has a cross-sectional shape in a plane perpendicular to the longitudinal axis, the cross-sectional shape of each of the set of protrusions independently being substantially circular, semicircular, ovate, ovoid, elliptic, triangular, rectangular, or polygonal. In some examples, the longitudinal axis of the set of protrusions extending from the top surface of the pyroelectric layer are each substantially parallel to the to the top surface of the pyroelectric layer. In some examples, the first surface of each of the set of protrusions is planar and the longitudinal axis of each of the set of protrusions is substantially perpendicular to the top surface, such that each of the set of protrusions extends from the first surface at the top surface of the pyroelectric layer along the longitudinal axis to the second surface. In some examples, the second surface is planar. In some examples, the second surface is non-planar.

In some examples, the detection electrode comprises a transparent conducting oxide, a metal oxide, a conducting polymer, a carbon material, a metal, printed circuit board (PCB), double sided PCB, or a combination thereof. In some examples, the detection electrode comprises a metal, carbon nanotubes, doped silicon, a conductive ink, or a combination thereof.

In some examples, the detection electrode is patterned such that the detection electrode comprises a patterned detection electrode, wherein the patterned detection electrode comprises a set of cavities, a set of protrusions, a set of particles, or a combination thereof.

In some examples, the patterned detection electrode has a top surface and a bottom surface opposite and spaced apart from the top surface, and wherein the patterned detection electrode comprises a set of cavities, wherein each of the cavities perforates the patterned detection electrode from the top surface to the bottom surface. In some examples, the set of cavities comprises a plurality of cavities arranged in an ordered array. In some examples, each of the set of cavities has a longitudinal axis and a cross-sectional shape in a plane perpendicular to the longitudinal axis, wherein the cross-sectional shape of each of the set of cavities is independently substantially circular, ovate, ovoid, elliptic, triangular, rectangular, or polygonal. In some examples, the set of cavities comprises a plurality of cavities and wherein the longitudinal axis of each of the plurality of second cavities is substantially parallel to each other and substantially perpendicular to the bottom surface of the patterned detection electrode.

In some examples, the patterned detection electrode has a top surface and a bottom surface opposite and spaced apart from the top surface, and wherein the patterned detection electrode comprises a set of protrusions, wherein each protrusion extends from the bottom surface of the patterned detection electrode. In some examples, the set of protrusions extending from the bottom surface of the patterned detection electrode comprises a plurality of protrusions arranged in an ordered array. In some examples, the set of protrusions extending from the bottom surface of the patterned detection electrode each has a longitudinal axis, a first surface, and a second surface opposite and axially spaced apart from the first surface, and wherein each of the set of protrusions has a cross-sectional shape in a plane perpendicular to the longitudinal axis, the cross-sectional shape of each of the set of protrusions independently being substantially circular, semicircular, ovate, ovoid, elliptic, triangular, rectangular, or polygonal. In some examples, the longitudinal axis of the set of protrusions extending from the bottom surface of the patterned detection electrode are each substantially parallel to the to the bottom surface of the patterned detection electrode. In some examples, the first surface of each of the set of protrusions is planar and the longitudinal axis of each of the set of protrusions is substantially perpendicular to the bottom surface, such that each of the set of protrusions extends from the first surface at the bottom surface of the patterned detection electrode along the longitudinal axis to the second surface. In some examples, the second surface is planar. In some examples, the second surface is non-planar.

In some examples, the patterned detection electrode has a top surface and a bottom surface opposite and spaced apart from the top surface, and wherein the patterned detection electrode comprises a set of particles disposed on the bottom surface of the patterned detection electrode.

In some examples, the distance is from 1 nm to 10 mm. In some examples, the distance is adjustable and the device further comprises a means for a means for controlling and/or adjusting the distance.

In some examples, the device further comprises a first substrate, wherein the temperature control layer is disposed on the first substrate. In some examples, the device further comprises a second substrate and a fluid flow control device, wherein the second substrate is disposed opposite and spaced apart from the first substrate and the fluid flow control device is disposed between the first substrate and the second substrate, and wherein the fluid flow control device is configured to control the flow of a fluid proximate to the first substrate to control dissipation of heat from temperature control layer. In some examples, the fluid flow control device comprises a fan or microfluidic channel.

Also disclosed herein are methods of making any of the gas detector devices disclosed herein. In some examples, the methods comprise making the patterned detection electrode. In some examples, the methods comprise making the textured top surface of the pyroelectric layer.

Also disclosed herein are gas detection methods for distinguishing a first gas component and a second gas component, the methods comprising: introducing a gas into the ionization zone of any of the gas detector devices disclosed herein while heating or cooling the temperature control layer to a first temperature at a first rate, which induces a first potential in the pyroelectric layer via the pyroelectric effect; wherein the gas comprises the first gas component and the second gas component; wherein the first gas component has a first ionization potential and the second gas component has a second ionization potential; wherein the second ionization potential is greater than the first ionization potential; wherein the first potential is greater than or equal to the first ionization potential and less than the second ionization potential; thereby ionizing the first gas component to produce a first ion; and electrically detecting the first ion via the detection electrode; subsequently, heating or cooling the temperature control layer to a second temperature at a second rate, which induces a second potential in the pyroelectric layer via the pyroelectric effect; wherein the second potential is greater than or equal to the second ionization potential; thereby ionizing the first gas component to produce the first ion and ionizing the second gas component to produce a second ion; and electrically detecting the first ion and the second ion via the detection electrode.

In some examples, the gas further comprises a third gas component; wherein the third gas component has a third ionization potential; wherein the third ionization potential is greater than the second ionization potential; and the methods further comprises distinguishing the third gas component. In some examples, the method comprises subsequently heating or cooling the temperature control layer to a third temperature at a third rate, which induces a third potential in the pyroelectric layer via the pyroelectric effect; wherein the third potential is greater than or equal to the third ionization potential; thereby ionizing the first gas component to produce the first ion, ionizing the second gas component to produce the second ion, and ionizing the third gas component to produce a third ion; and electrically detecting the first ion, the second ion, and the third ion via the detection electrode.

In some examples, the first gas component, the second gas component, the third gas component (when present), or a combination thereof independently comprise, for example, a volatile organic compound, an inorganic gas, or a combination thereof. In some examples, the gas comprises ambient air. In some examples, the first gas component, the second gas component, the third gas component (when present), or a combination thereof comprises a biomarker. In some examples, the gas comprises a gaseous or aerosolized bodily fluid. In some examples, the first gas component, the second gas component, the third gas component (when present), or a combination thereof comprises a pathogen, a biomarker indicative of a pathogen, or a combination thereof. In some examples, the first gas component, the second gas component, the third gas component (when present), or a combination thereof comprises a toxin, a contaminant, a warfare agent, or a combination thereof.

In some examples, the first ionization potential, the second ionization potential, and the third ionization potential (when the third gas component is present) are, independently, from 1 eV to 30 eV or from 7 eV to 26 eV. In some examples, the first temperature, the second temperature, and the third temperature (when the third gas component is present) are, independently, from −200° C. to 500° C. In some examples, the first rate, the second rate, and the third rate when the third gas component is present) are, independently, from 0.01° C./second to 100° C./second.

In some examples, the methods further comprise processing the electrical signals from the detection electrode to determine a property, wherein the property comprises the presence of the first gas component, the second gas component, the third gas component, or a combination thereof; the identity of the first gas component, the second gas component, the third gas component (when present), or a combination thereof; the relative amount of the first gas component, the second gas component, the third gas component (when present), or a combination thereof in the gas; or a combination thereof. In some examples, processing the electrical signal from the detection electrode comprises integrating the electrical signal from the detection electrode and the property comprises the total number of ions detected by the detection electrode.

In some examples, the method further comprises diagnosing and/or monitoring a disease in a subject by determining the property of the gas. In some examples, the method further comprises selecting a course of therapy for the subject based on the property of the gas.

In some examples, the methods comprise air quality monitoring, environmental monitoring, toxic gas detection, exhaled breath analysis, or a combination thereof.

Also disclosed herein are methods of use of any of the devices described herein, the methods comprising using the gas detector devices for air quality monitoring, environmental monitoring, toxic gas detection, exhaled breath analysis, or a combination thereof. Also disclosed herein are methods of use of any of the devices described herein, the methods comprising using the gas detector devices for chemical process monitoring, monitoring of gases in pipes, monitoring inside reactors, monitoring inside fridge/oven/and other consumer appliances, monitoring inside a subject's body, or a combination thereof.

Additional advantages of the disclosed devices and methods will be set forth in part in the description which follows, and in part will be obvious from the description. The advantages of the disclosed devices and methods will be realized and attained by means of the elements and combinations particularly pointed out in the appended claims. It is to be understood that both the foregoing general description and the following detailed description are exemplary and explanatory only and are not restrictive of the disclosed devices and methods, as claimed.

The details of one or more embodiments of the invention are set forth in the accompanying drawings and the description below. Other features, objects, and advantages of the invention will be apparent from the description and drawings, and from the claims.

DESCRIPTION OF FIGURES

The accompanying figures, which are incorporated in and constitute a part of this specification, illustrate several aspects of the disclosure, and together with the description, serve to explain the principles of the disclosure.

(FIG. 41A) Ionization energies of common gaseous molecules in order of increasing ionization potential. (FIG. 41B) Schematic shows the variation in temperature rate required to ionize gaseous molecules with different ionization energies.

(FIG. 49A) Ionization of acetone (left three panels). (FIG. 49B) Ionization of ambient air (right three panels).

DETAILED DESCRIPTION

Figure 1:
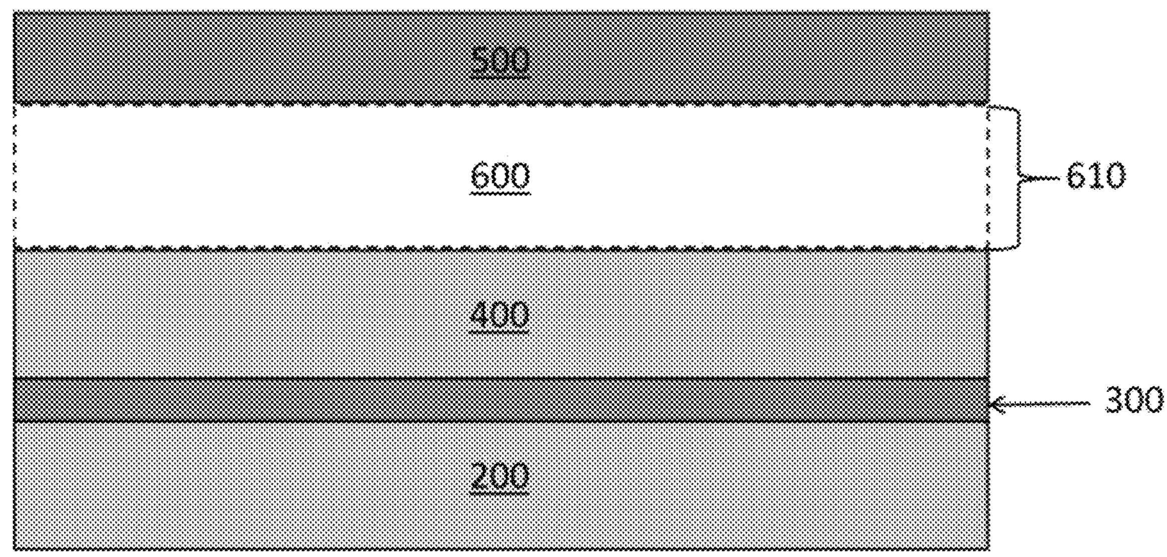
FIG. 1 is a schematic plan view of an example device as disclosed herein according to one implementation.

The systems and methods described herein may be understood more readily by reference to the following detailed description of specific aspects of the disclosed subject matter and the Examples included therein.

Before the present systems and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Exemplary" means "an example of" and is not intended to convey an indication of a preferred or ideal embodiment. "Such as" is not used in a restrictive sense, but for explanatory purposes.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

It is understood that throughout this specification the identifiers "first" and "second" are used solely to aid the reader in distinguishing the various components, features, or steps of the disclosed subject matter. The identifiers "first" and "second" are not intended to imply any particular order, amount, preference, or importance to the components or steps modified by these terms.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

Disclosed herein are gas detector devices and methods of making and use thereof.

Figure 2:
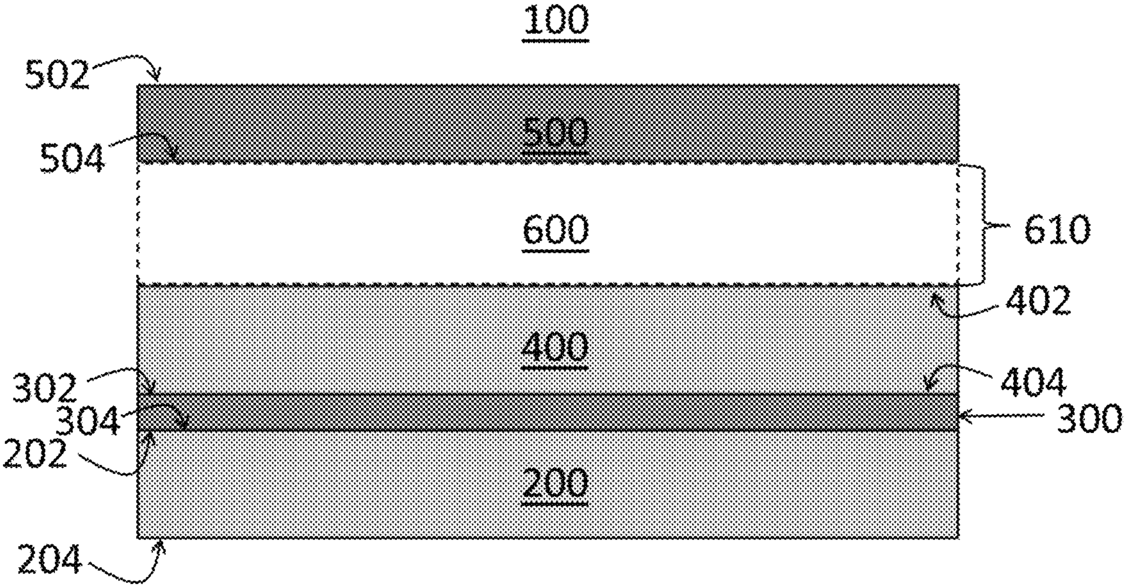
FIG. 2 is a schematic plan view of an example device as disclosed herein according to one implementation.

Referring now to FIG. 1-FIG. 2, disclosed herein are gas detector devices 100 comprising: a temperature control layer 200; a grounded electrode 300 disposed on the temperature control layer 200, wherein the grounded electrode 300 is thermally conductive and is in thermal contact with the temperature control layer 200; a pyroelectric layer 400 comprising a pyroelectric material, wherein the pyroelectric layer 400 is disposed on the grounded electrode 300 such that the grounded electrode 300 is disposed between the temperature control layer 200 and the pyroelectric layer 400, and wherein the pyroelectric layer 400 is in thermal contact and electrical contact with the grounded electrode 300; and a detection electrode 500 opposite and spaced apart from the pyroelectric 400 layer by a distance 610, such that the detection electrode 500 and the pyroelectric layer 400 define an ionization zone 600 between the detection electrode 500 and the pyroelectric layer 400.

The temperature control layer 200 can comprise any material consistent with the methods, devices, and systems disclosed herein. The temperature control layer 200 can comprise any thermally conductive material. In some examples, the temperature control layer 200 can comprise a semiconductor, a ceramic, a transparent conducing oxide, a polymer, a carbon material, a metal, or a combination thereof. In some examples, the temperature control layer 200 can comprise a metallic resistive heating or cooling material, a ceramic heating or cooling material, a thermoelectric material, an induction heating or cooling material, an optical heating or cooling material, or a combination thereof.

In some examples, the temperature control layer 200 comprises a thermoelectric material. Examples of thermoelectric materials include, but are not limited to, bismuth telluride ($Bi_2Te_3$), lead telluride (PbTe), silicon germanium (SiGe), derivatives thereof, and combinations thereof. In some examples, the temperature control layer 200 comprises a Peltier element.

In some examples, the temperature control layer 200 can comprise a metal, such as a metal selected from the group consisting of Al, Ti, Ni, Cu, Ga, In, Ag, Ir, Pt, Au, Cr, Mo, Pd, Sn, W, and combinations thereof.

In some examples, the temperature control layer 200 can comprise a carbon material. Examples of carbon materials include, but are not limited to, graphitic carbon and graphites, including pyrolytic graphite (e.g., highly ordered pyrolytic graphite (HOPG)) and isotropic graphite, amorphous carbon, carbon black, single- or multi-walled carbon nanotubes, buckminsterfullerene ($C_{60}$), graphene, glassy carbon, diamond-like carbon (DLC) or doped DLC, such as boron-doped diamond, pyrolyzed photoresist films, and others known in the art.

Figure 3:
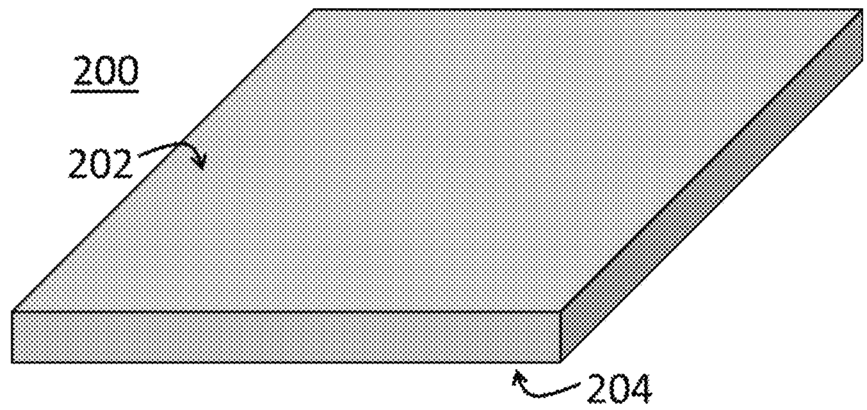
FIG. 3 is a schematic illustration of an example temperature control layer as disclosed herein according to one implementation.
Figure 4:
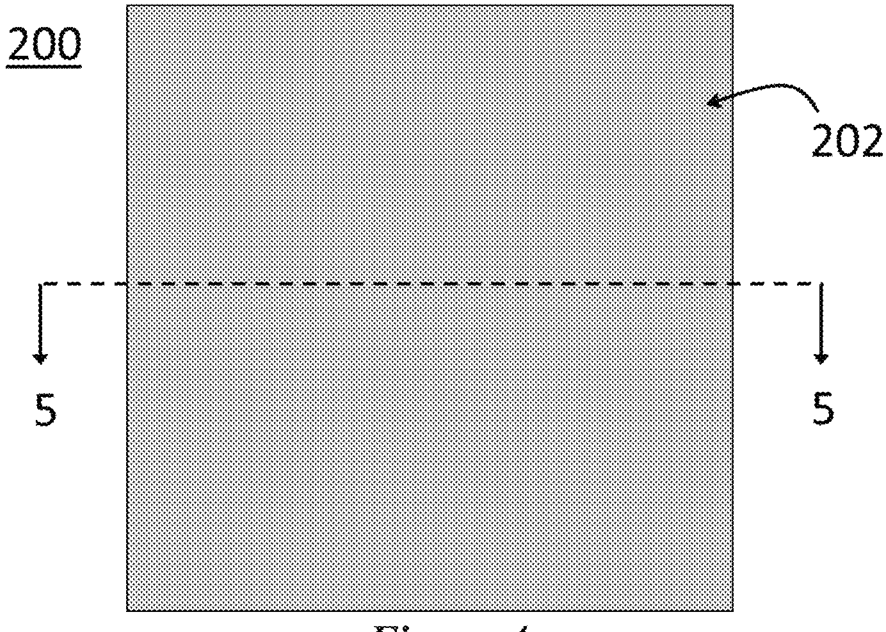
FIG. 4 is a schematic plan view of the example temperature control layer shown in FIG. 3.
Figure 5:
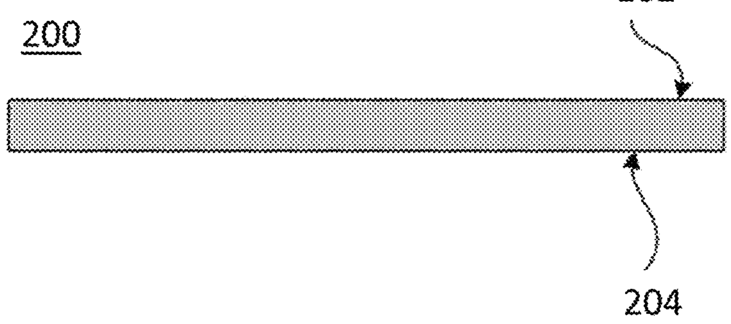
FIG. 5 is a cross-sectional plan view along 5-5 in FIG. 4 of the example temperature control layer shown in FIG. 3 and FIG. 4.

Referring now to FIG. 3-FIG. 5, the temperature control layer 200 has a top surface 202 and a bottom surface 204 opposite and spaced apart from the top surface 202. In some examples, the top surface 202 and the bottom surface 204 of the temperature control layer are substantially parallel to each other.

The temperature control layer 200 has an average thickness, the average thickness being the average dimension from the top surface 202 to the bottom surface 204. The average thickness of the temperature control layer 200 can, for example, be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the average thickness of the temperature control layer 200 can be 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average thickness of the temperature control layer 200 can range from any of the minimum values described above to any of the maximum values described above. For example, the average thickness of the temperature control layer 200 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 202 and the bottom surface 204 of the temperature control layer 200 can, independently, be any shape. In some examples, the top surface 202 and the bottom surface 204 of the temperature control layer 200 can, independently, be substantially circular, ovate, ovoid, elliptic, triangular, rectangular, polygonal, etc. In some examples, the top surface 202 and the bottom surface 204 of the temperature control layer 200 can be substantially the same shape. In some examples, the top surface 202 and the bottom surface 204 of the temperature control layer 200 can be substantially rectangular, as shown in FIG. 3-FIG. 5.

The temperature control layer 200 has an average lateral dimension (e.g., diameter when the temperature control layer 200 is circular; diagonal when the temperature control layer 200 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the temperature control layer 200 can be 300 millimeters (mm) or less (e.g., 250 mm or less, 200 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the temperature control layer 200 can range from any of the minimum values described above to any of the maximum values described above. For example, the average lateral dimension of the temperature control layer 200 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm).

In some examples, the devices 100 further comprise a means for controlling the temperature of the temperature control layer 200 (not shown). Examples of suitable means for controlling the temperature of the temperature control layer 200 are known in the art. For example, the means for controlling the temperature control layer 200 can include a resistive heating or cooling means, a thermoelectric heating or cooling means, an optical heating or cooling means (e.g., laser, UV, infrared, etc.), an induction heating or cooling means, a water heating or cooling means, a Peltier element, or a combination thereof. In some examples, the devices further comprise a power source connected to the temperature control layer, the power source being configured to control the temperature of the temperature control layer 200.

The gas detector devices 100 comprises a grounded electrode 300 disposed on the temperature control layer 200, wherein the grounded electrode 300 is thermally conductive and is in thermal contact with the temperature control layer 200. In some examples, the grounded electrode is deposited on the temperature control layer using techniques, such as, for example, electroplating, lithographic deposition, electron beam deposition, thermal deposition, spin coating, drop-casting, zone casting, dip coating, blade coating, spraying, vacuum filtration, chemical vapor deposition (CVD), atomic layer deposition (ALD), physical vapor deposition (PVD), sputtering, pulsed layer deposition, molecular beam epitaxy, evaporation, or combinations thereof.

In some examples, the grounded electrode 300 is bonded to the temperature control layer 200. For example, the grounded electrode 300 can be bonded to the temperature control layer 300 via adhesive bonding (e.g., via an appropriate glue or other adhesive, such as a thermal adhesive), anodic bonding, thermocompression bonding, fusion bonding, eutectic bonding, direct bonding, complex oxide bonding, metallic bonding, or a combination thereof.

The grounded electrode 300 can comprise any material consistent with the methods, devices, and systems disclosed herein. Examples of suitable electrode materials are known in the art. The grounded electrode 300 can comprise, for example, a transparent conducting oxide, a metal oxide, a conducting polymer, a carbon material, a metal, or a combination thereof. In some examples, the grounded electrode 300 can comprise a metal, carbon nanotubes, doped silicon, a conductive ink, or a combination thereof.

In some examples, the grounded electrode 300 can comprise a metal, such as a metal selected from the group consisting of Al, Ti, Ni, Cu, Ga, In, Ag, Ir, Pt, Au, Cr, Mo, Pd, Sn, W, and combinations thereof.

Examples of carbon materials include, but are not limited to, graphitic carbon and graphites, including pyrolytic graphite (e.g., highly ordered pyrolytic graphite (HOPG)) and isotropic graphite, amorphous carbon, carbon black, single- or multi-walled carbon nanotubes, buckminsterfullerene ($C_{60}$), graphene, glassy carbon, diamond-like carbon (DLC) or doped DLC, such as boron-doped diamond, pyrolyzed photoresist films, and others known in the art.

In some examples, the grounded electrode 300 can comprise a transparent conducting oxide or a graphene-based transparent conducting electrode. Examples of transparent conducting oxides include, but are not limited to, indium doped tin oxide (ITO), fluorine doped tin oxide (FTO), aluminum zinc oxide (AZO), tin doped indium oxide, and combinations thereof.

In some examples, the grounded electrode 300 can comprise a metal oxide. Examples of metal oxides include simple metal oxides (e.g., with a single metal element) and mixed metal oxides (e.g., with different metal elements). The metal oxide can, for example, comprise a metal selected from the group consisting of Cd, Cr, Cu, Ga, In, Ni, Sn, Ti, W, Zn, and combinations thereof. In some examples, the grounded electrode 300 can comprise $CdIn_2O_4$, $Cd_2SnO_4$, $Cr_2O_3$, $CuCrO_2$, $Cu_2O$, $Ga_2O_3$, $In_2O_3$, NiO, $SnO_2$, $TiO_2$, $ZnGa_2O_4$, ZnO, InZnO, InGaZnO, InGaO, ZnSnO, $Zn_2SnO_4$, CdSnO, $WO_3$, or combinations thereof.

In some examples, the grounded electrode 300 can comprise a conducting polymer such as polyacetylene, polyalanine, poly(3,4-ethylenedioxythiophene) polystyrene sulfonate, polypyrrole, derivatives thereof, or combinations thereof.

The grounded electrode 300 can be configured to remove charges from the bottom surface 404 of the pyroelectric crystal 400.

Figure 6:
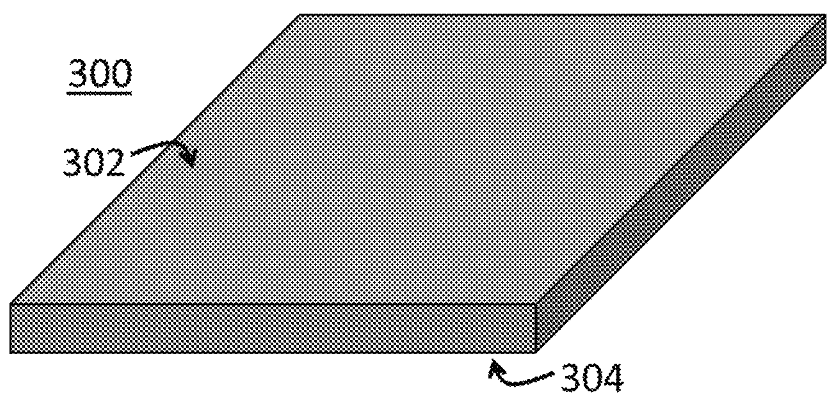
FIG. 6 is a schematic illustration of an example grounded electrode as disclosed herein according to one implementation.
Figure 7:
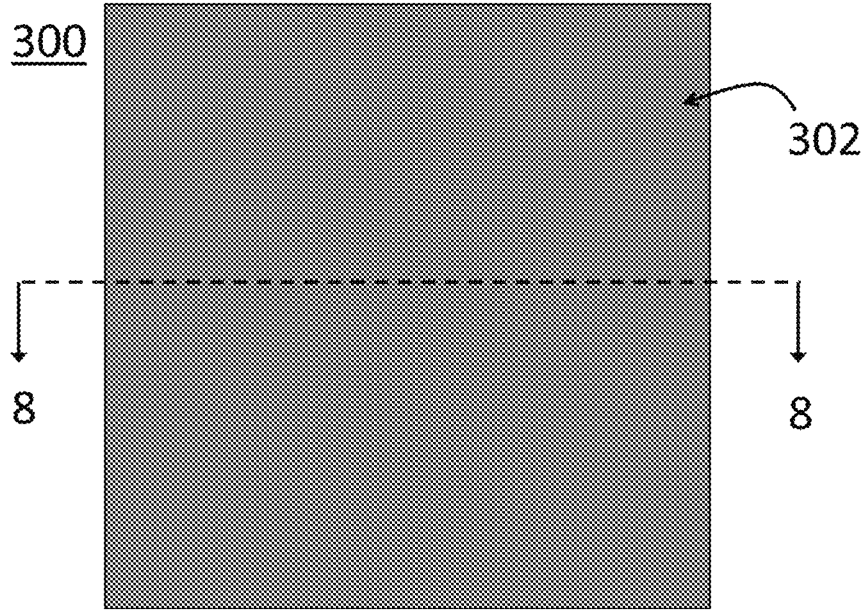
FIG. 7 is a schematic plan view of the example grounded electrode shown in FIG. 6.
Figure 8:
FIG. 8 is a cross-sectional plan view along 8-8 in FIG. 6 of the example grounded electrode shown in FIG. 7 and FIG. 8.

Referring now to FIG. 6-FIG. 8, the grounded electrode 300 has a top surface 302 and a bottom surface 304 opposite and spaced apart from the top surface 302. In some examples, the top surface 302 and the bottom surface 304 of the grounded electrode 300 are substantially parallel to each other. The grounded electrode 300 can, for example, be disposed on the temperature control layer 200 such that the bottom surface 304 of the grounded electrode 300 is disposed on the top surface 202 of the temperature control layer 200. In some examples, the bottom surface 304 of the grounded electrode 300 is bonded to the top surface 202 of the temperature control layer 200. In some examples, the top surface 302 and the bottom surface 304 of the grounded electrode 300 and the top surface 202 and the bottom surface 204 of the temperature control layer 200 are all substantially parallel to each other.

The grounded electrode 300 has an average thickness, the average thickness being the average dimension from the top surface 302 to the bottom surface 304. The average thickness of the grounded electrode 300 can, for example, be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, or 5 mm or more). In some examples, the average thickness of the grounded electrode 300 can be 10 millimeters (mm) or less (e.g., 9 mm or less, 8 mm or less, 7 mm or less, 6 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average thickness of the grounded electrode 300 can range from any of the minimum values described above to any of the maximum values described above. For example, the average thickness of the grounded electrode 300 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 302 and the bottom surface 304 of the grounded electrode 300 can, independently, be any shape. In some examples, the top surface 302 and the bottom surface 304 of the grounded electrode 300 can, independently, be substantially circular, ovate, ovoid, elliptic, triangular, rectangular, polygonal, etc. In some examples, the top surface 302 and the bottom surface 304 of the grounded electrode 300 can be substantially the same shape. In some examples, the top surface 302 and the bottom surface 304 of the grounded electrode 300 can be substantially rectangular, as shown in FIG. 6-FIG. 8.

The grounded electrode 300 has an average lateral dimension (e.g., diameter when the grounded electrode 300 is circular; diagonal when the grounded electrode 300 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the grounded electrode 300 can be 300 millimeters (mm) or less (e.g., 275 mm or less, 250 mm or less, 225 mm or less, 200 mm or less, 175 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the grounded electrode 300 can range from any of the minimum values described above to any of the maximum values described above. For example, the average lateral dimension of the grounded electrode 300 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm).

The gas detector devices 100 comprise a pyroelectric layer 400 comprising a pyroelectric material, wherein the pyroelectric layer 400 is disposed on the grounded electrode 300 such that the grounded electrode 300 is disposed between the temperature control layer 200 and the pyroelectric layer 400, and wherein the pyroelectric layer 400 is in thermal contact and electrical contact with the grounded electrode 300. In some examples, the pyroelectric layer 400 is bonded to the grounded electrode 300. For example, the pyroelectric layer 400 can be bonded to the grounded electrode 300 via adhesive bonding (e.g., via an appropriate thermally and electrically conductive glue or other adhesive), anodic bonding, thermocompression bonding, fusion bonding, eutectic bonding, direct bonding, complex oxide bonding, metallic bonding, or a combination thereof.

The pyroelectric layer 400 comprises a pyroelectric material. The pyroelectric material can be any material consistent with the methods, devices, and systems disclosed herein. Examples of suitable pyroelectric materials are known in the art. Examples of pyroelectric materials include, but are not limited to, lithium niobate ($LiNbO_3$), barium titanate ($BaTO_3$), lithium tantalate ($LiTaO_3$), lead zirconate titanate (PZT), rochelle salt ($KNaC_4H_4O_6$), cesium nitrate ($CsNO_3$), tourmaline, hemimorphite ($Zn_4Si_2O_7(OH)_2 \cdot H_2O$), $BiFeO_3$, $BiCoO_3$, $BiCrO_3BiMnO_3$, $BiNiO_3$, $BiTiO_3$, $CdTiO_3$, $CsGeCl_3$, $KTaO_3$, $KIO_3$, $KTiO_3$, $KNbO_3$, $NaNbO_3$, $PbTiO_3$, $PbFeO_3$, $PbZrO_3$, $PbVO_3$, $SrTiO_3$, $AgNbO_3$, $AgTaO_3$, $PbNb_2O_6$, $PbTa_2O_6$, $K_2BiNb_5O_{15}$, $Pb_2BiTaO_6$, $Pb_2BiNbO_6$, $Bi_2WO_6$, $SrBi_2Nb_2O_9$, $Bi_4Ti_3O_{12}$, $SrBi_4Ti_4O_{15}$, $BaMgF_4$, $BaNiF_4$, $KH_2PO_4$, $(NH_4)_2SO_4$, poly(vinylidene fluoride-trifluoroethylene)-based [P(VDF-TrFE)] polymer, P(VDF-TrFE-CFE) (CFE: chlorofluoroethylene) polymer, $PbZr_{0.2}Ti_{0.8}O_3$, $Ba_{0.67}Sr_{0.33}TiO_3$, $SrTiO_3$, GaN, aluminum nitride (AlN), scandium doped aluminum nitride (ScAlN), potassium-sodium niobate (KNN), derivatives thereof, and combinations thereof. In some examples, the pyroelectric material can comprise lithium niobate ($LiNbO_3$), barium titanate ($BaTO_3$), lithium tantalate ($LiTaO_3$), lead zirconate titanate (PZT), cesium nitrate ($CsNO_3$), tourmaline, aluminum nitride (AlN), scandium doped aluminum nitride (ScAlN), potassium-sodium niobate (KNN), derivatives thereof, and combinations thereof. In some examples, the pyroelectric material can comprise lithium niobate ($LiNbO_3$), such as z-cut lithium niobate.

Figure 9:
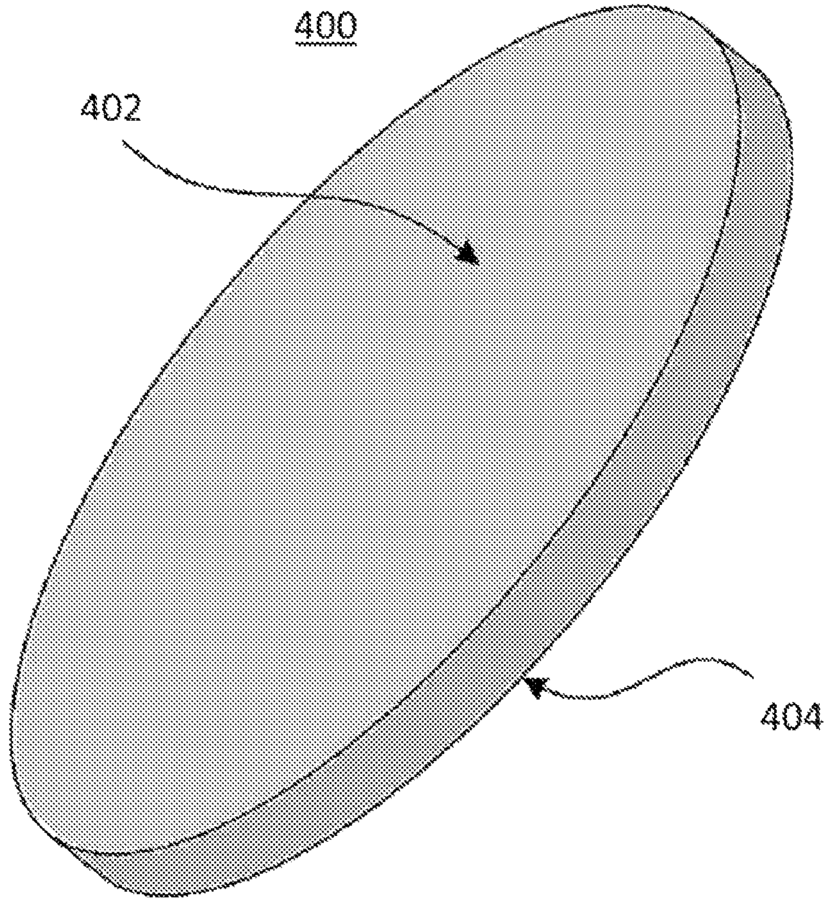
FIG. 9 is a schematic illustration of an example pyroelectric layer as disclosed herein according to one implementation.
Figure 10:
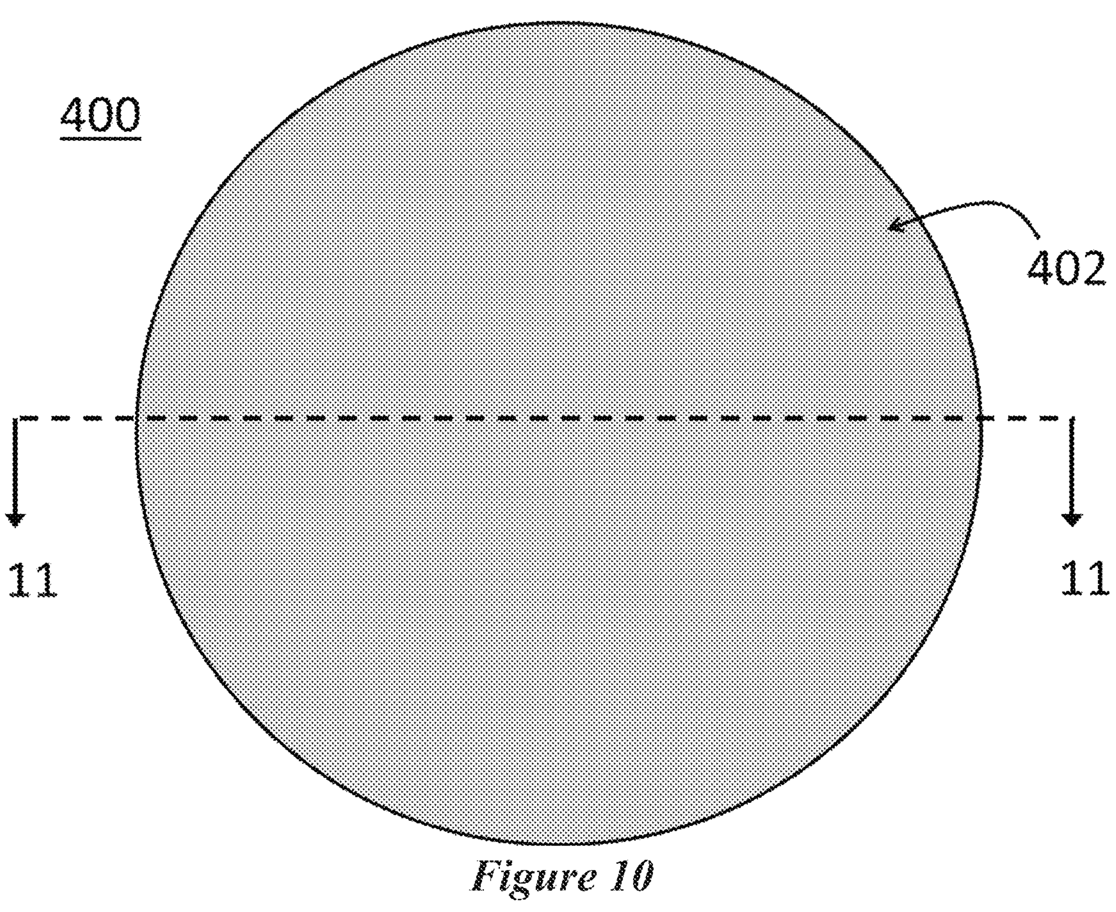
FIG. 10 is a schematic plan view of the example pyroelectric layer shown in FIG. 9.
Figure 11:
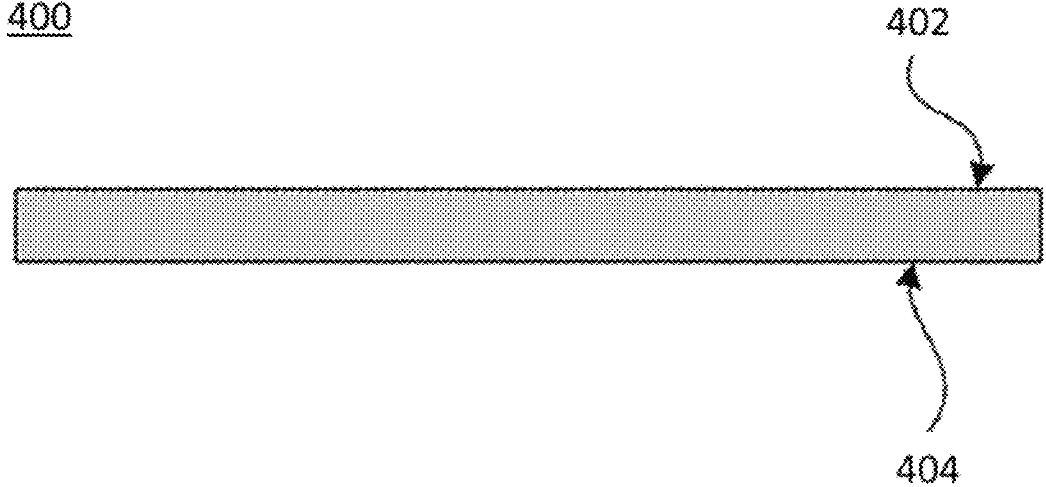
FIG. 11 is a cross-sectional plan view along 11-11 in FIG. 10 of the example pyroelectric layer shown in FIG. 9 and FIG. 10.

Referring now to FIG. 9-FIG. 11, the pyroelectric layer 400 has a top surface 402 and a bottom surface 404 opposite and spaced apart from the top surface 402. In some examples, the top surface 402 and the bottom surface 404 of the pyroelectric layer 400 are substantially parallel to each other. The pyroelectric layer 400 can, for example, be disposed on the grounded electrode 300 such that the bottom surface 404 of the pyroelectric layer 400 is disposed on the top surface 302 of the grounded electrode 300. In some examples, the bottom surface 404 of the pyroelectric layer 400 can be bonded to the top surface 302 of the grounded electrode 300. In some examples, the top surface 402 and the bottom surface 404 of the pyroelectric layer 400 and the top surface 302 and the bottom surface 304 of the grounded electrode 300 are all substantially parallel to each other. In some examples, the top surface 402 and the bottom surface 404 of the pyroelectric layer 400; the top surface 302 and the bottom surface 304 of the grounded electrode 300; and the top surface 202 and the bottom surface 204 of the temperature control layer 200 are all substantially parallel to each other.

The pyroelectric layer 400 has an average thickness, the average thickness being the average dimension from the top surface 402 to the bottom surface 404. The average thickness of the pyroelectric layer 400 can, for example, be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 6 mm or more, 7 mm or more, 8 mm or more, or 9 mm or more). In some examples, the average thickness of the pyroelectric layer 400 can be 10 millimeters (mm) or less (e.g., 9 mm or less, 8 mm or less, 7 mm or less, 6 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average thickness of the pyroelectric layer 400 can range from any of the minimum values described above to any of the maximum values described above. For example, the average thickness of the pyroelectric layer 400 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 402 and the bottom surface 404 of the pyroelectric layer 400 can, independently, be any shape. In some examples, the top surface 402 and the bottom surface 404 of the pyroelectric layer 400 can, independently, be substantially circular, ovate, ovoid, elliptic, triangular, rectangular, polygonal, etc. In some examples, the top surface 402 and the bottom surface 404 of the pyroelectric layer 400 can be substantially the same shape. In some examples, the top surface 402 and the bottom surface 404 of the pyroelectric layer 400 can be substantially circular, as shown in FIG. 9-FIG. 11.

The pyroelectric layer 400 has an average lateral dimension (e.g., diameter when the pyroelectric layer 400 is circular; diagonal when the pyroelectric layer 400 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the pyroelectric layer 400 can be 300 millimeters (mm) or less (e.g., 275 mm or less, 250 mm or less, 225 mm or less, 200 mm or less, 175 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the pyroelectric layer 400 can range from any of the minimum values described above to any of the maximum values described above. For example, the average lateral dimension of the pyroelectric layer 400 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm). In some examples, the average lateral dimension of the grounded electrode 300 is 75% or more (e.g., 80% or more, 90% or more, 100% or more, 110% or more, 125% or more, 150% or more) of the average lateral dimension of the pyroelectric layer 400. In some examples, the average lateral dimension of the grounded electrode is greater than or equal to the average lateral dimension of the pyroelectric layer 400.

In some examples, the top surface 402 of the pyroelectric layer 400 can be textured. For example, the pyroelectric layer 400 can comprise a set of protrusions 420 extending from the top surface 402, a set of particles 430 disposed on the top surface 402, or a combination thereof. In some examples, the textured top surface 402 of the pyroelectric layer 400 can be surface roughness.

In some examples, the pyroelectric layer 400 can comprise a set of protrusions 420 extending from the top surface 402. The set of protrusions 420 can be integrally formed with the pyroelectric layer 400.

As used herein, "a set of protrusions 420" and "the set of protrusions 420" are meant to include any number of protrusions 420 in any arrangement. Thus, for example, "a set of protrusions 420" includes one or more protrusions 420 (e.g., 2 or more; 3 or more; 4 or more; 5 or more; 10 or more; 15 or more; 20 or more; 25 or more; 30 or more; 40 or more; 50 or more; 75 or more; 100 or more; 150 or more; 200 or more; 250 or more; 300 or more; 400 or more; 500 or more; 750 or more; 1000 or more; 1500 or more; 2000 or more; 2500 or more; 3000 or more; 4000 or more; 5000 or more; 7500 or more; $1\times10^4$ or more; $2.5\times10^4$ or more; $5\times10^4$ or more; $7.5\times10^4$ or more; $1\times10^5$ or more; $2.5\times10^5$ or more; $5\times10^5$ or more; $7.5\times10^5$ or more; $1\times10^6$ or more; $5\times10^6$ or more; $1\times10^7$ or more; $5\times10^7$ or more; $1\times10^8$ or more; $5\times10^8$ or more; $1\times10^9$ or more; $5\times10^9$ or more; $1\times10^{10}$ or more; $1\times10^{11}$ or more; $1\times10^{12}$ or more; $1\times10^{13}$ or morel $1\times10^{14}$ or more; $1\times10^{15}$ or more; $1\times10^{16}$ or more; $1\times10^{17}$ or more; $1\times10^{18}$ or more; $1\times10^{19}$ or more; or $1\times10^{20}$ or more). In some examples, the set of protrusions 420 can comprise a plurality of protrusions 420. In some examples, the set of protrusions 420 comprises a plurality of protrusions 420 in an ordered array.

The set of protrusions 420 extending from the top surface 402 of the pyroelectric layer 400 can, independently, be any shape. For example, the set of protrusions 420 can, independently, be a polyhedron (e.g., a platonic solid, a prism, a pyramid), a cylinder, a hemicylinder, an elliptical cylinder, a hemi-elliptical cylinder, a sphere, a hemisphere, a cone, a semicone, etc.

Figure 12:
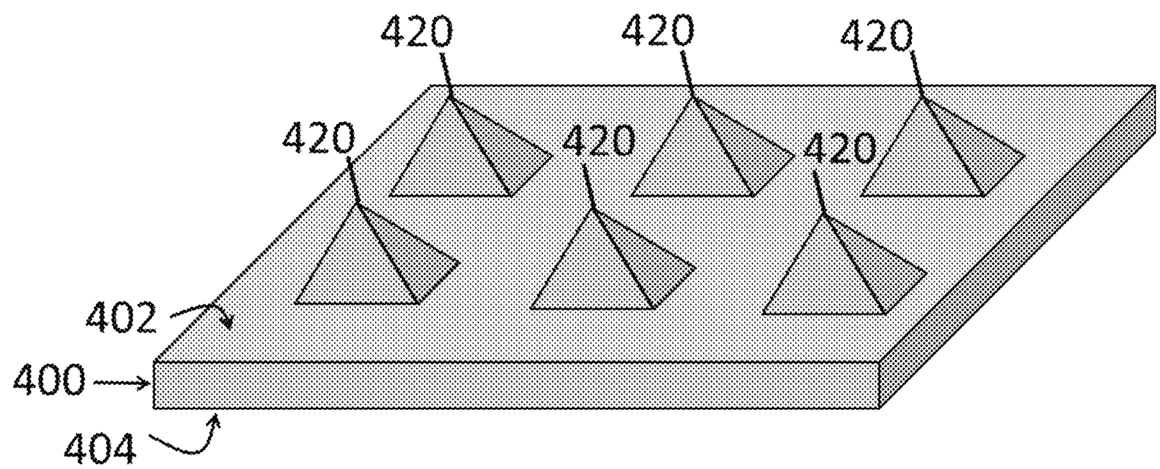
FIG. 12 is a schematic illustration of an example pyroelectric layer with a textured top surface as disclosed herein according to one implementation.

In some examples, the set of protrusions 420 can, independently, be a platonic solid, a pyramid, a sphere, a hemisphere, a cone, a semicone, etc. In some examples, the set of protrusions 420 can, independently, be spherical, hemispherical, ellipsoidal, triangular, pyramidal, tetrahedral, cylindrical, rectangular, cuboidal, cuboctahedral, etc. Referring now to FIG. 12, the set of protrusions 420 can, for example, be pyramidal. The set of protrusions 420 can have an average size. The term "size," as used herein, refers to the largest straight line distance spanning the protrusion 420 in the plane of the top surface 402 of the pyroelectric layer. "Average size" and "mean size" are used interchangeably herein, and generally refer to the statistical mean size of the protrusions in a population of protrusions. For example, for a set of protrusions 420 having a substantially circular shape in the plane of top surface of the pyroelectric layer, the average size can refer to the average diameter.

The set of protrusions 420 can, for example, have an average size of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of protrusions 420 can have an average size of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average size of the set of protrusions 420 can range from any of the minimum values described above to any of the maximum values described above. For example, the average size of the set of protrusions 420 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of protrusions 420 can comprise a plurality of protrusions wherein the average size of the plurality of protrusions 420 can be substantially monodisperse. "Monodisperse" and "homogeneous size distribution," as used herein, and generally describe a population of protrusions where all of the protrusions have the same or nearly the same average size. As used herein, a monodisperse distribution refers to distributions in which 80% of the distribution (e.g., 85% of the distribution, 90% of the distribution, or 95% of the distribution) lies within 25% of the average size (e.g., within 20% of the average size, within 15% of the average size, within 10% of the average size, or within 5% of the average size).

In some examples, each of the protrusions 420 can have a longitudinal axis, a first surface, and a second surface opposite and axially spaced apart from the first surface. The first surface and the second surface can, independently, be planar (e.g., flat) or non-planar (e.g., pyramidal, hemispherical, conical, etc.). In some examples, the longitudinal axis of each of the protrusions 420 are substantially parallel to each other.

The longitudinal axis of each of the protrusions 420 can have an average length, wherein the average length is 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, 9 mm or more, 10 mm or more, 15 mm or more, 20 mm or more, 25 mm or more, 30 mm or more, 35 mm or more, 40 mm or more, 45 mm or more, 50 mm or more, 60 mm or more, 70 mm or more, 80 mm or more, 90 mm or more, 100 mm or more, 125 mm or more, 150 mm or more, 175 mm or more, 200 mm or more, 225 mm or more, 250 mm or more, or 275 mm or more). In some examples, the average length of the longitudinal axis of the set of protrusions 420 can be 300 millimeters (mm) or less (e.g., 275 mm or less, 250 mm or less, 225 mm or less, 200 mm or less, 175 mm or less, 150 mm or less, 125 mm or less, 100 mm or less, 90 mm or less, 80 mm or less, 70 mm or less, 60 mm or less, 50 mm or less, 45 mm or less, 40 mm or less, 35 mm or less, 30 mm or less, 25 mm or less, 20 mm or less, 15 mm or less, 10 mm or less, 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average length of the longitudinal axis of the set of protrusions 420 can range from any of the minimum values described above to any of the maximum values described above. For example, the average length of the longitudinal axis of the set of protrusions 420 can be from 1 micrometer (nm) to 300 millimeters (mm) (e.g., from 1 nm to 1 μm, from 1 μm to 100 μm, from 100 μm to 10 mm, from 10 mm to 300 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 10 mm to 150 mm, from 150 mm to 300 mm, from 1 nm to 100 mm, from 10 nm to 300 mm, or from 10 nm to 100 mm).

In some examples, the set of protrusions 420 can comprise a plurality of protrusions wherein the average length of the longitudinal axis of the plurality of protrusions 420 can be substantially monodisperse. "Monodisperse" and "homogeneous length distribution," as used herein, and generally describe a population of protrusions where all of the protrusions have the same or nearly the same average longitudinal axis length. As used herein, a monodisperse distribution refers to distributions in which 80% of the distribution (e.g., 85% of the distribution, 90% of the distribution, or 95% of the distribution) lies within 25% of the average length (e.g., within 20% of the average length, within 15% of the average length, within 10% of the average length, or within 5% of the average length).

Each of the protrusions 420 can have a cross-sectional shape in a plane perpendicular to the longitudinal axis, wherein the cross-sectional shape can be any shape, such as a regular shape, an irregular shape, an isotropic shape, or an anisotropic shape. In some examples, the cross-sectional shape of each of the set of protrusions can be substantially circular, ovate, ovoid, elliptic, triangular, rectangular, polygonal, etc. In some examples, the cross-sectional shape of each of the set of protrusions 420 is substantially the same.

The set of protrusions 420 can have an average characteristic dimension. The term "characteristic dimension," as used herein refers to the largest straight line distance between two points in the plane of the cross-sectional shape of each of the protrusions. "Average characteristic dimension" and "mean characteristic dimension" are used interchangeably herein, and generally refer to the statistical mean characteristic dimension of the protrusions in a population of protrusions. For example, for a cylindrical set of second protrusions, the cross-sectional shape can be substantially circular and the average characteristic dimension can refer to the average diameter.

The set of protrusions 420 can, for example, have an average characteristic dimension of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of protrusions 420 can have an average characteristic dimension of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average characteristic dimension of the set of protrusions 420 can range from any of the minimum values described above to any of the maximum values described above. For example, the average characteristic dimension of the set of protrusions 420 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of protrusions 420 can comprise a plurality of protrusions wherein the average characteristic dimension of the plurality of protrusions 420 can be substantially monodisperse. "Monodisperse" and "homogeneous characteristic dimension distribution," as used herein, and generally describe a population of protrusions where all of the protrusions have the same or nearly the same average characteristic dimension. As used herein, a monodisperse distribution refers to distributions in which 80% of the distribution (e.g., 85% of the distribution, 90% of the distribution, or 95% of the distribution) lies within 25% of the average characteristic dimension (e.g., within 20% of the average characteristic dimension, within 15% of the average characteristic dimension, within 10% of the average characteristic dimension, or within 5% of the average characteristic dimension).

In some examples, the set of protrusions 420 can, independently, be a prism (e.g., a triangular prism, rectangular prism, polygonal prism), a cylinder, a hemicylinder, an elliptical cylinder, a hemi-elliptical cylinder, etc.

Figure 13:
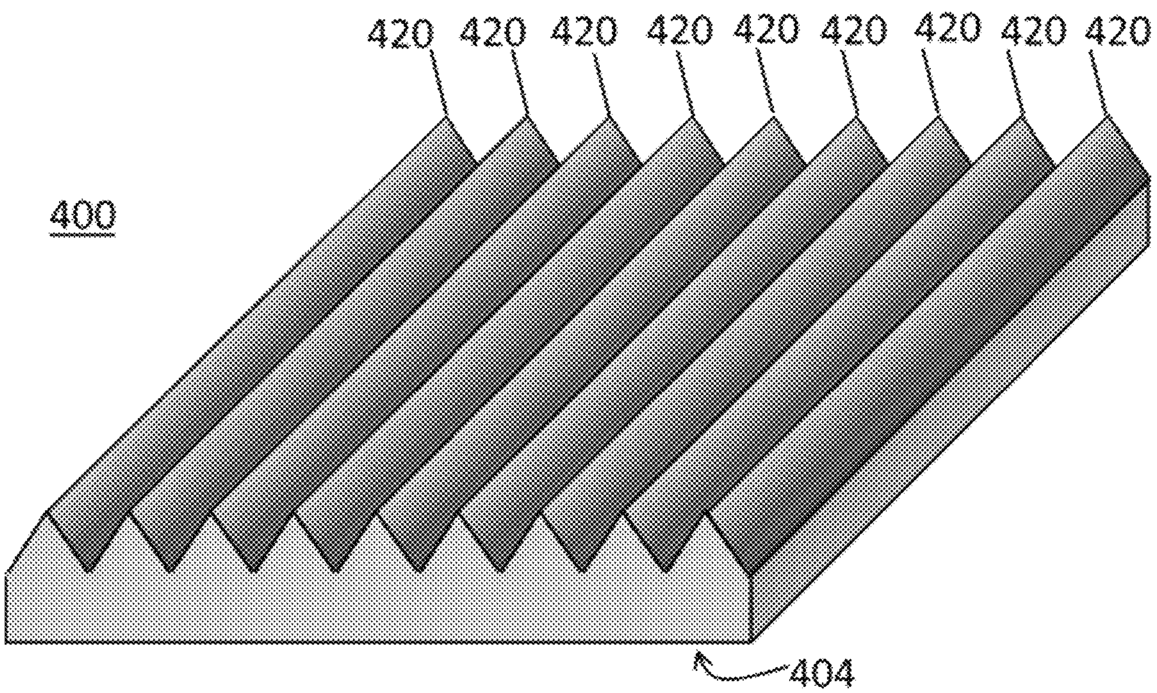
FIG. 13 is a schematic illustration of an example pyroelectric layer with a textured top surface as disclosed herein according to one implementation.
Figures 14, 15:
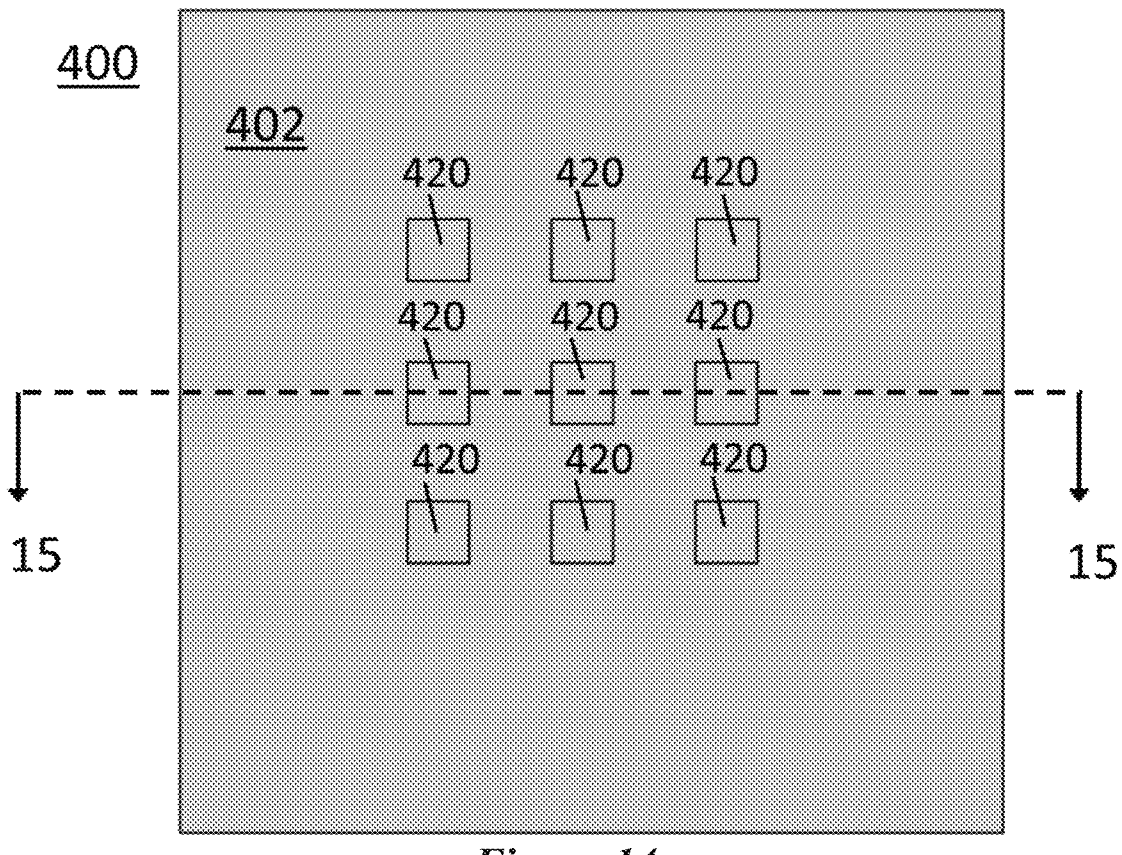
FIG. 14 is a schematic plan view of an example pyroelectric layer with a textured top surface as disclosed herein according to one implementation.
FIG. 15 is a cross-sectional plan view along 15-15 in FIG. 14 of the example pyroelectric layer with a textured top surface.
Figure 16:
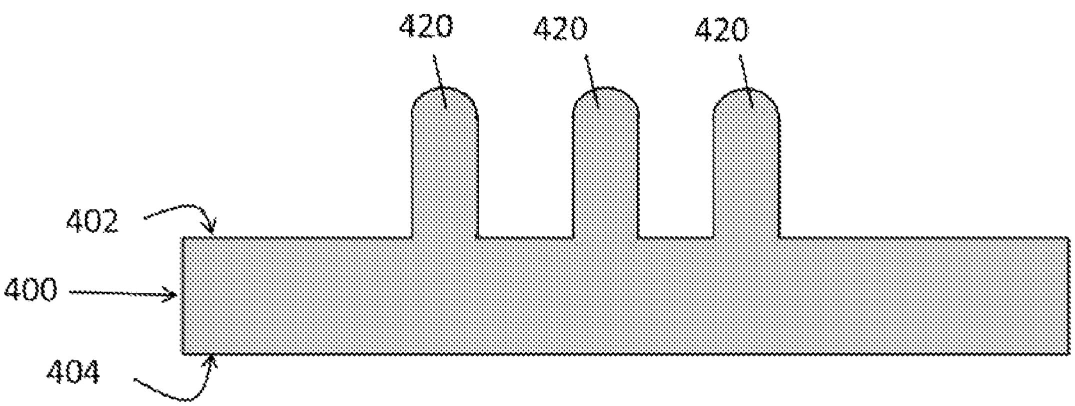
FIG. 16 is a cross-sectional plan view of an example pyroelectric layer with a textured top surface.

In some examples, the longitudinal axis of each of the protrusions 420 is substantially parallel to the top surface 402 of the pyroelectric layer 400. For example, the longitudinal axis of each of the protrusions 420 is substantially parallel to the top surface 402 of the pyroelectric layer 400 such that the top surface 402 of the pyroelectric layer is corrugated, grooved, ridged, etc. Referring now to FIG. 13, the set of protrusions 420 can, for example, be triangular prisms having a longitudinal axis substantially parallel to the top surface 402 of the pyroelectric layer 400.

Figure 17:
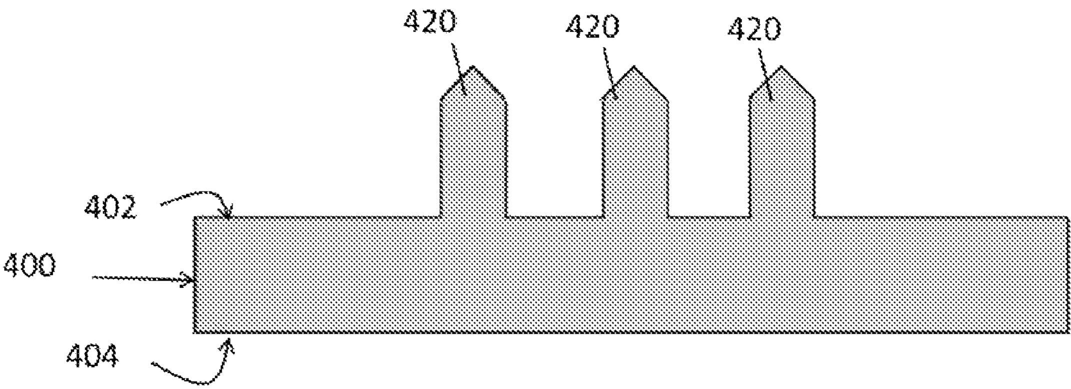
FIG. 17 is a cross-sectional plan view of an example pyroelectric layer with a textured top surface.

In some examples, the first surface of the protrusions 420 is planar and the longitudinal axis of each of the protrusions 420 is substantially perpendicular to the top surface 402 of the pyroelectric layer 400, such that the set of protrusions 420 extend from the first surface at the top surface 402 of the pyroelectric layer 400 along the longitudinal axis to the second surface. The second surface can be planar (e.g., flat) or non-planar (e.g., pyramidal, hemispherical, conical, etc.). Referring now to FIG. 14-FIG. 17, the protrusions 420 can, for example, be rectangular prisms having a planar second surface (FIG. 15), a hemispherical second surface (FIG. 16), and/or a pyramidal second surface (FIG. 17).

Figure 56:
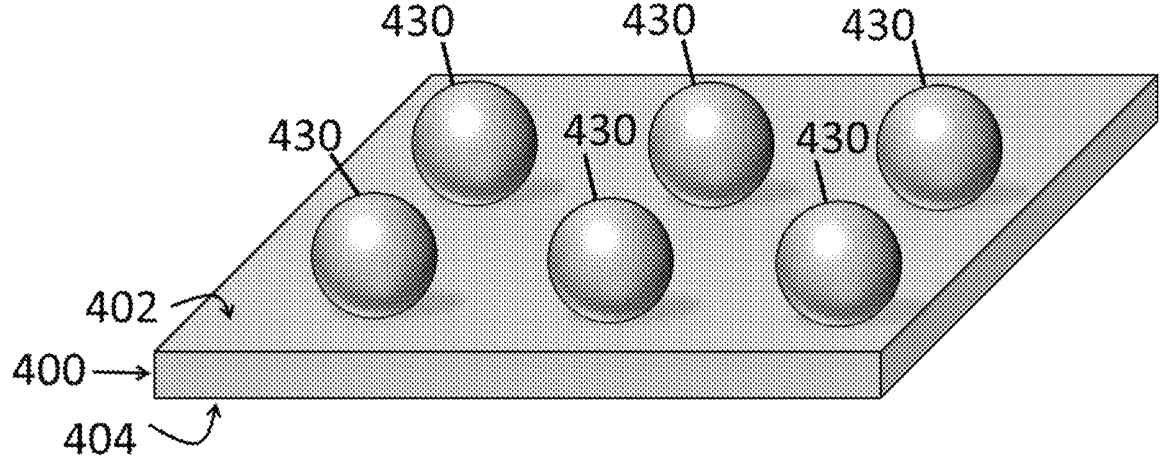
FIG. 56 is a schematic illustration of an example pyroelectric layer with a textured top surface as disclosed herein according to one implementation.

In some examples, the pyroelectric layer 400 can comprise a set of particles 430 disposed on the top surface 402 (FIG. 56). As used herein, "a set of particles 430" and "the set of particles 430" are meant to include any number of particles 430 in any arrangement. Thus, for example, "a set of particles 430" includes one or more particles 430 (e.g., 2 or more; 3 or more; 4 or more; 5 or more; 10 or more; 15 or more; 20 or more; 25 or more; 30 or more; 40 or more; 50 or more; 75 or more; 100 or more; 150 or more; 200 or more; 250 or more; 300 or more; 400 or more; 500 or more; 750 or more; 1000 or more; 1500 or more; 2000 or more; 2500 or more; 3000 or more; 4000 or more; 5000 or more; 7500 or more; $1\times10^4$ or more; $2.5\times10^4$ or more; $5\times10^4$ or more; $7.5\times10^4$ or more; $1\times10^5$ or more; $2.5\times10^5$ or more; $5\times10^5$ or more; $7.5\times10^5$ or more; $1\times10^6$ or more; $5\times10^6$ or more; $1\times10^7$ or more; $5\times10^7$ or more; $1\times10^8$ or more; $5\times10^8$ or more; $1\times10^9$ or more; $5\times10^9$ or more; $1\times10^{10}$ or more; $1\times10^{11}$ or more; $1\times10^{12}$ or more; $1\times10^{13}$ or morel $1\times10^{14}$ or more; $1\times10^{15}$ or more; $1\times10^{16}$ or more; $1\times10^{17}$ or more; $1\times10^{18}$ or more; $1\times10^{19}$ or more; or $1\times10^{20}$ or more). In some examples, the set of particles 430 can comprise a plurality of particles 430. In some examples, the set of particles 430 comprises a plurality of particles 430 in an ordered array.

The set of particles 430 can, for example, comprise a pyroelectric material. The pyroelectric material can be any material consistent with the methods, devices, and systems disclosed herein. Examples of suitable pyroelectric materials are known in the art. Examples of pyroelectric materials include, but are not limited to, lithium niobate ($LiNbO_3$), barium titanate ($BaTO_3$), lithium tantalate ($LiTaO_3$), lead zirconate titanate (PZT), rochelle salt ($KNaC_4H_4O_6$), cesium nitrate ($CsNO_3$), tourmaline, hemimorphite ($Zn_4Si_2O_7(OH)_2 \cdot H_2O$), $BiFeO_3$, $BiCoO_3$, $BiCrO_3BiMnO_3$, $BiNiO_3$, $BiTiO_3$, $CdTiO_3$, $CsGeCl_3$, $KTaO_3$, $KIO_3$, $KTiO_3$, $KNbO_3$, $NaNbO_3$, $PbTiO_3$, $PbFeO_3$, $PbZrO_3$, $PbVO_3$, $SrTiO_3$, $AgNbO_3$, $AgTaO_3$, $PbNb_2O_6$, $PbTa_2O_6$, $K_2BiNb_5O_{15}$, $Pb_2BiTaO_6$, $Pb_2BiNbO_6$, $Bi_2WO_6$, $SrBi_2Nb_2O_9$, $Bi_4Ti_3O_{12}$, $SrBi_4Ti_4O_{15}$, $BaMgF_4$, $BaNiF_4$, $KH_2PO_4$, $(NH_4)_2SO_4$, poly(vinylidene fluoride-trifluoroethylene)-based [P(VDF-TrFE)] polymer, P(VDF-TrFE-CFE) (CFE: chlorofluoroethylene) polymer, $PbZr_{0.2}Ti_{0.8}O_3$, $Ba_{0.67}Sr_{0.33}TiO_3$, $SrTiO_3$, GaN, aluminum nitride (AlN), scandium doped aluminum nitride (ScAlN), potassium-sodium niobate (KNN), derivatives thereof, and combinations thereof. In some examples, the pyroelectric material can comprise lithium niobate ($LiNbO_3$), barium titanate ($BaTO_3$), lithium tantalate ($LiTaO_3$), lead zirconate titanate (PZT), cesium nitrate ($CsNO_3$), tourmaline, aluminum nitride (AlN), scandium doped aluminum nitride (ScAlN), potassium-sodium niobate (KNN), derivatives thereof, and combinations thereof. In some examples, the pyroelectric material can comprise lithium niobate ($LiNbO_3$). The set of particles 430 can, for example a pyroelectric material that is the same as or different than the pyroelectric material of the pyroelectric layer 400. In some examples, the set of particles 430 and the pyroelectric layer 400 comprise the same pyroelectric material.

The set of particles 430 can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. As used herein, the size of a particle can refer to the largest linear distance between two points on the surface of the particle. For an anisotropic particle, the average particle size can refer to, for example, the average maximum dimension of the particle (e.g., the length of a rod shaped particle, the diagonal of a cube shape particle, the bisector of a triangular shaped particle, etc.). Mean particle size can be measured using methods known in the art, such as evaluation by electron microscopy.

The set of particles 430 can have an average particle size of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of particles 430 can have an average particle size of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average particle size of the set of particles 430 can range from any of the minimum values described above to any of the maximum values described above. For example, the average particle size of the set of particles 430 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of particles 430 can comprise a plurality of particles which can be substantially monodisperse. "Monodisperse" and "homogeneous size distribution," as used herein, and generally describe a population of particles where all of the particles have the same or nearly the average particle size. As used herein, a monodisperse distribution refers to particle distributions in which 80% of the distribution (e.g., 85% of the distribution, 90% of the distribution, or 95% of the distribution) lies within 25% of the average particle size (e.g., within 20% of the average particle size, within 15% of the average particle size, within 10% of the average particle size, or within 5% of the average particle size).

The set of particles 430 can be of any shape (e.g., a sphere, a rod, a quadrilateral, an ellipse, a triangle, a polygon, etc.). In some examples, the set of particles 430 can have an isotropic shape. In some examples, the set of particles 430 can have an anisotropic shape. The gas detector devices 100 comprise a detection electrode 500 opposite and spaced apart from the pyroelectric 400 layer by a distance 610, such that the detection electrode 500 and the pyroelectric layer 400 define an ionization zone 600 between the detection electrode 500 and the pyroelectric layer 400.

The detection electrode 500 can comprise any material consistent with the methods, devices, and systems disclosed herein. Examples of suitable electrode materials are known in the art. The detection electrode 500 can comprise, for example, a transparent conducting oxide, a metal oxide, a conducting polymer, a carbon material, a metal, printed circuit board (PCB), double sided PCB, or a combination thereof. In some examples, the detection electrode 500 can comprise a metal, carbon nanotubes, doped silicon, a conductive ink, or a combination thereof.

In some examples, the detection electrode 500 can comprise a metal, such as a metal selected from the group consisting of Al, Ti, Ni, Cu, Ga, In, Ag, Ir, Pt, Au, Cr, Mo, Pd, Sn, W, and combinations thereof.

Examples of carbon materials include, but are not limited to, graphitic carbon and graphites, including pyrolytic graphite (e.g., highly ordered pyrolytic graphite (HOPG)) and isotropic graphite, amorphous carbon, carbon black, single- or multi-walled carbon nanotubes, buckminsterfullerene ($C_{60}$), graphene, glassy carbon, diamond-like carbon (DLC) or doped DLC, such as boron-doped diamond, pyrolyzed photoresist films, and others known in the art.

In some examples, the detection electrode 500 can comprise a transparent conducting oxide or a graphene-based transparent conducting electrode. Examples of transparent conducting oxides include, but are not limited to, indium doped tin oxide (ITO), fluorine doped tin oxide (FTO), aluminum zinc oxide (AZO), tin doped indium oxide, and combinations thereof.

In some examples, the detection electrode 500 can comprise a metal oxide. Examples of metal oxides include simple metal oxides (e.g., with a single metal element) and mixed metal oxides (e.g., with different metal elements). The metal oxide can, for example, comprise a metal selected from the group consisting of Cd, Cr, Cu, Ga, In, Ni, Sn, Ti, W, Zn, and combinations thereof. In some examples, the detection electrode 500 can comprise $CdIn_2O_4$, $Cd_2SnO_4$, $Cr_2O_3$, $CuCrO_2$, $Cu_2O$, $Ga_2O_3$, $In_2O_3$, NiO, $SnO_2$, $TiO_2$, $ZnGa_2O_4$, ZnO, InZnO, InGaZnO, InGaO, ZnSnO, $Zn_2SnO_4$, CdSnO, $WO_3$, or combinations thereof.

In some examples, the detection electrode 500 can comprise a conducting polymer such as polyacetylene, polyalanine, poly(3,4-ethylenedioxythiophene) polystyrene sulfonate, polypyrrole, derivatives thereof, or combinations thereof.

Figure 18:
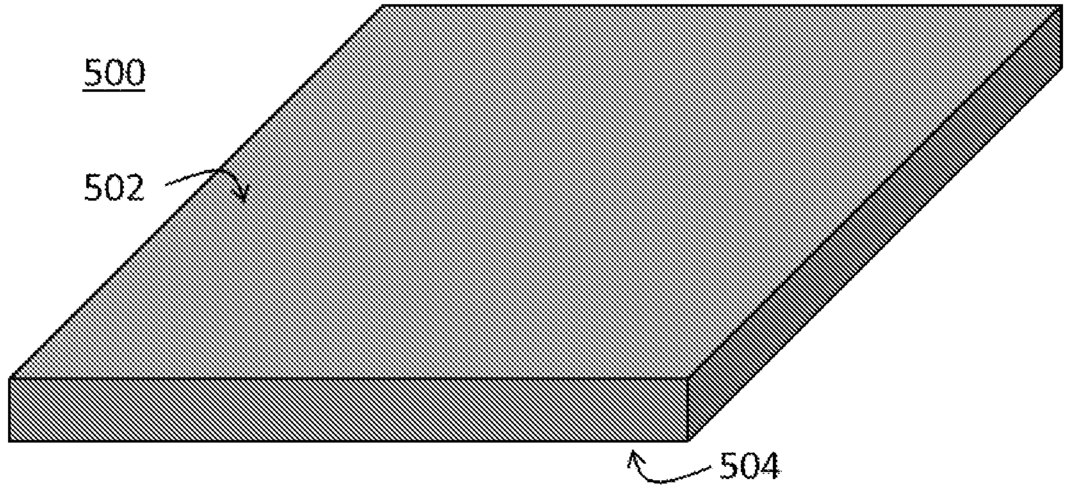
FIG. 18 is a schematic illustration of an example detection electrode as disclosed herein according to one implementation.
Figure 19:
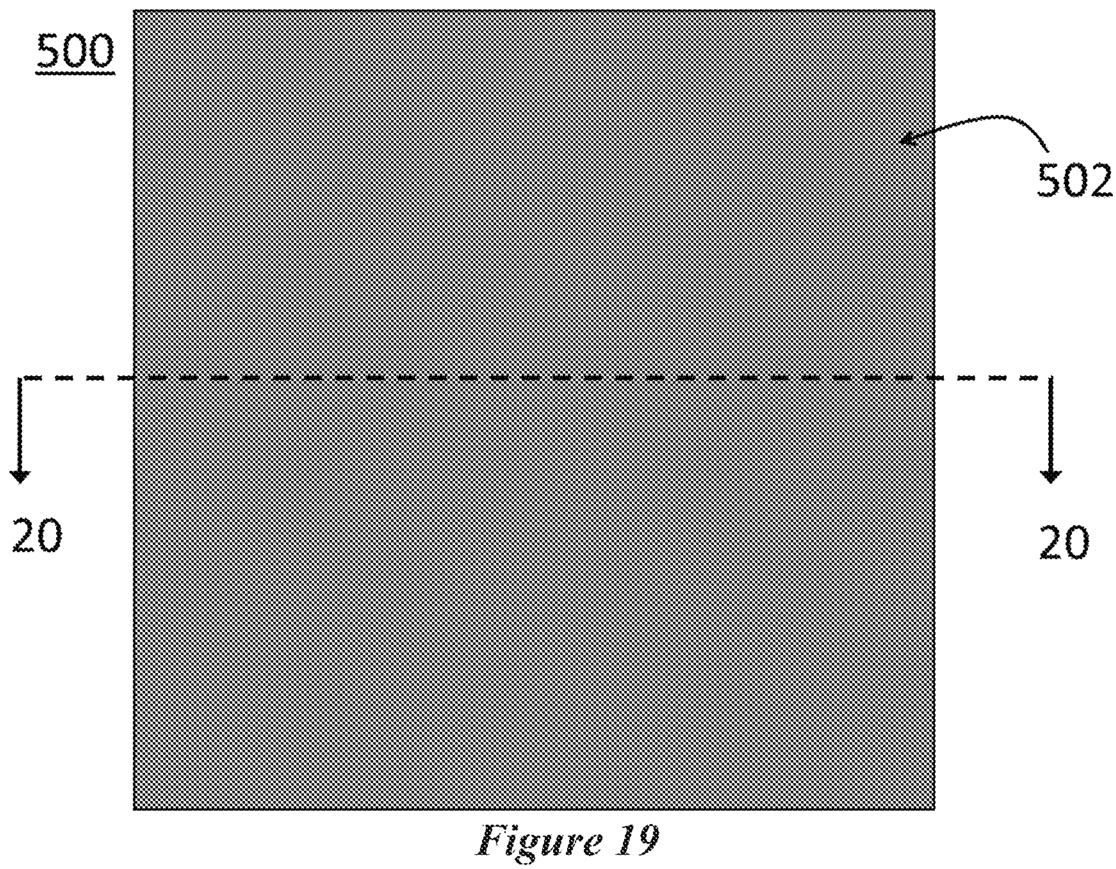
FIG. 19 is a schematic plan view of the example detection electrode shown in FIG. 18.
Figure 20:
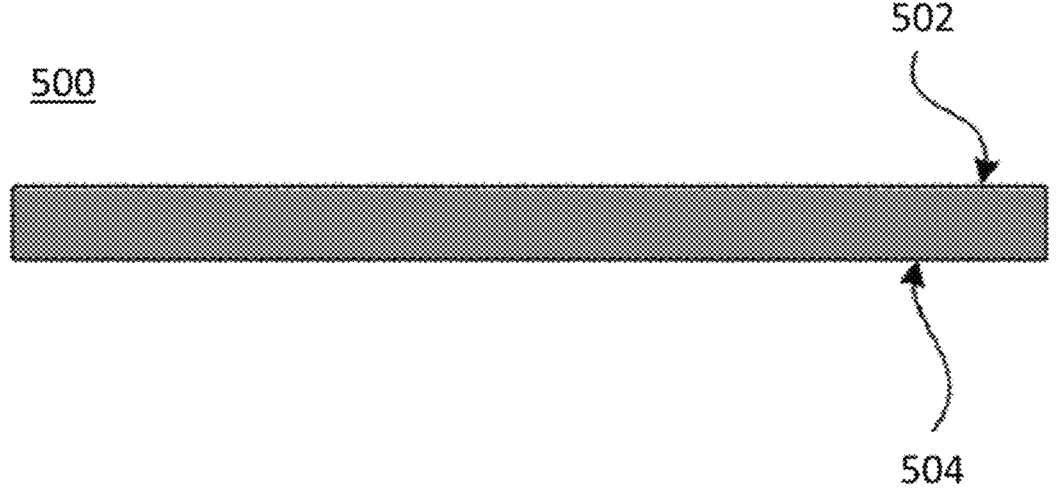
FIG. 20 is a cross-sectional plan view along 20-20 in FIG. 19 of the example detection electrode shown in FIG. 18 and FIG. 19.
Figure 21:
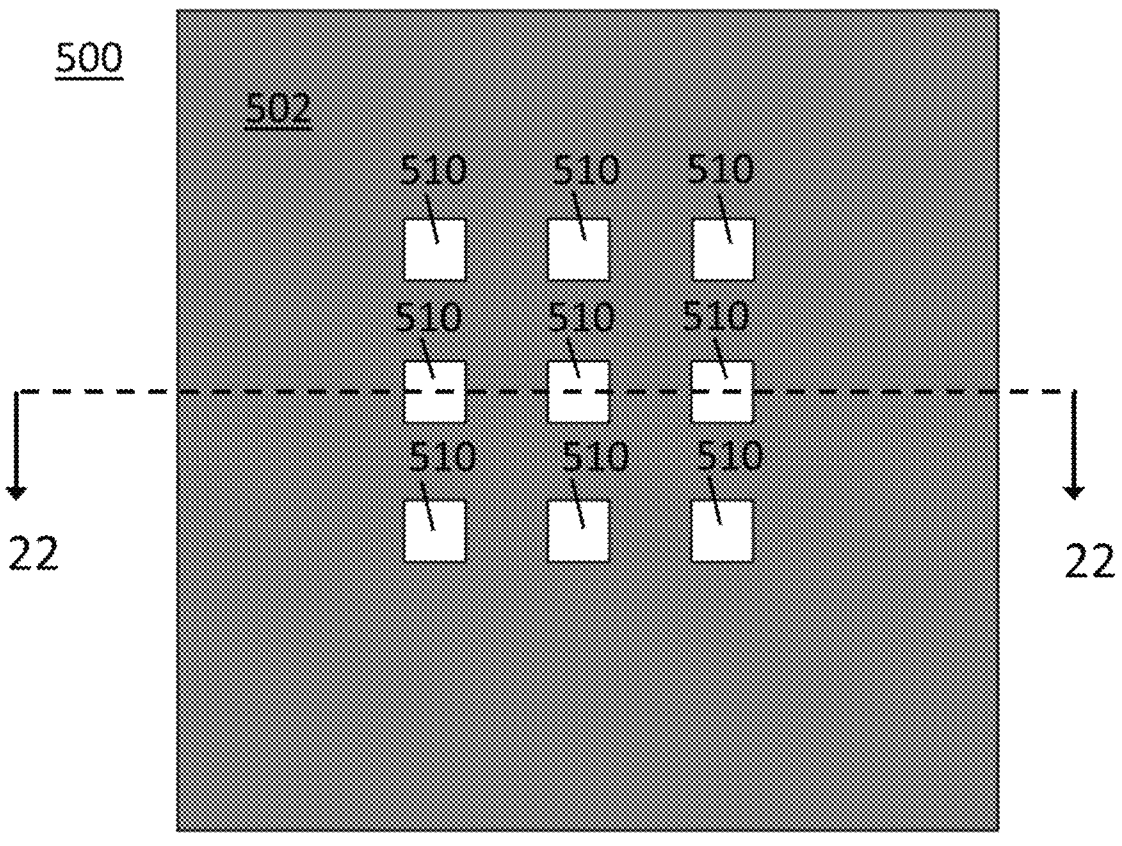
FIG. 21 is a schematic plan view of an example patterned detection electrode as disclosed herein according to one implementation.
Figure 22:
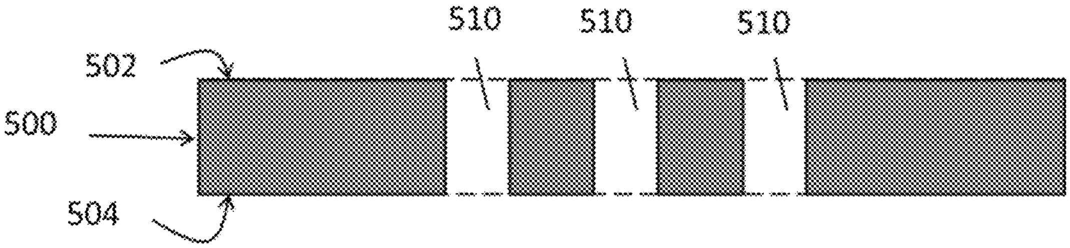
FIG. 22 is a cross-sectional plan view along 22-22 in FIG. 21 of the example patterned detection electrode.

Referring now to FIG. 18-FIG. 20, the detection electrode 500 has a top surface 502 and a bottom surface 504 opposite and spaced apart from the top surface 502. In some examples, the top surface 502 and the bottom surface 504 of the detection electrode 500 are substantially parallel to each other. The detection electrode 500 is disposed opposite and spaced apart from the pyroelectric layer 400 by a distance 610, such that the bottom surface 504 of the detection electrode 500 is disposed opposite and spaced apart from the top surface 402 of the pyroelectric layer 400 by the distance 610. In some examples, the top surface 502 and the bottom surface 504 of the detection electrode 500 and the top surface 402 and the bottom surface 404 of the pyroelectric layer 400 are all substantially parallel to each other. In some examples, the top surface 502 and the bottom surface 504 of the detection electrode 500; the top surface 402 and the bottom surface 404 of the pyroelectric layer 400; the top surface 302 and the bottom surface 304 of the grounded electrode 300; and the top surface 202 and the bottom surface 204 of the temperature control layer 200 are all substantially parallel to each other.

The detection electrode 500 has an average thickness, the average thickness being the average dimension from the top surface 502 to the bottom surface 504. The average thickness of the detection electrode 500 can, for example, be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the average thickness of the detection electrode 500 can be 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 20 μm or less, 15 μm or less, 10 μm or less, 5 μm or less, 4 μm or less, 3 μm or less, or 2 μm or less). The average thickness of the detection electrode 500 can range from any of the minimum values described above to any of the maximum values described above. For example, the average thickness of the detection electrode 500 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 502 and the bottom surface 504 of the detection electrode 500 can, independently, be any shape. In some examples, the top surface 502 and the bottom surface 504 of the detection electrode 500 can, independently, be substantially circular, ovate, ovoid, elliptic, triangular, rectangular, polygonal, etc. In some examples, the top surface 502 and the bottom surface 504 of the detection electrode 500 can be substantially the same shape. In some examples, the top surface 502 and the bottom surface 504 of the detection electrode 500 can be substantially rectangular, as shown in FIG. 18-FIG. 20.

The detection electrode 500 has an average lateral dimension (e.g., diameter when the detection electrode 500 is circular; diagonal when the detection electrode 500 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the detection electrode 500 can be 300 millimeters (mm) or less (e.g., 275 mm or less, 250 mm or less, 225 mm or less, 200 mm or less, 175 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the detection electrode 500 can range from any of the minimum values described above to any of the maximum values described above. For example, the average lateral dimension of the detection electrode 500 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm).

In some examples, the detection electrode 500 can be patterned. For example, the detection electrode 500 can comprise a patterned detection electrode 500 comprising a set of cavities 510, a set of protrusions 520, a set of particles 530, or a combination thereof. In some examples, the detection electrode 500 can comprise a patterned detection electrode 500, wherein the pattern can comprise surface roughness.

In some examples, the detection electrode 500 can be patterned via electroplating, lithographic deposition, electron beam deposition, thermal deposition, spin coating, drop-casting, zone casting, dip coating, blade coating, spraying, vacuum filtration, chemical vapor deposition (CVD), atomic layer deposition (ALD), physical vapor deposition (PVD), sputtering, pulsed layer deposition, molecular beam epitaxy, evaporation, or combinations thereof. In some examples, the methods can further comprise patterning the detection electrode 500, for example via electroplating, lithographic deposition, electron beam deposition, thermal deposition, spin coating, drop-casting, zone casting, dip coating, blade coating, spraying, vacuum filtration, chemical vapor deposition (CVD), atomic layer deposition (ALD), physical vapor deposition (PVD), sputtering, pulsed layer deposition, molecular beam epitaxy, evaporation, or combinations thereof.

In some examples, the patterned detection electrode 500 comprises a set of cavities 510, wherein each of the cavities 510 perforates the patterned detection electrode 500 from the top surface 502 to the bottom surface 504.

As used herein, "a set of cavities 510" and "the set of cavities 510" are meant to include any number of cavities 510 in any arrangement. Thus, for example, "a set of cavities 510" includes one or more cavities 510 (e.g., 2 or more; 3 or more; 4 or more; 5 or more; 10 or more; 15 or more; 20 or more; 25 or more; 30 or more; 40 or more; 50 or more; 75 or more; 100 or more; 150 or more; 200 or more; 250 or more; 300 or more; 400 or more; 500 or more; 750 or more; 1000 or more; 1500 or more; 2000 or more; 2500 or more; 3000 or more; 4000 or more; 5000 or more; 7500 or more; $1\times10^4$ or more; $2.5\times10^4$ or more; $5\times10^4$ or more; $7.5\times10^4$ or more; $1\times10^5$ or more; $2.5\times10^5$ or more; $5\times10^5$ or more; $7.5\times10^5$ or more; $1\times10^6$ or more; $5\times10^6$ or more; $1\times10^7$ or more; $5\times10^7$ or more; $1\times10^8$ or more; $5\times10^8$ or more; $1\times10^9$ or more; $5\times10^9$ or more; $1\times10^{10}$ or more; $1\times10^{11}$ or more; $1\times10^{12}$ or more; $1\times10^{13}$ or morel $1\times10^{14}$ or more; $1\times10^{15}$ or more; $1\times10^{16}$ or more; $1\times10^{17}$ or more; $1\times10^{18}$ or more; $1\times10^{19}$ or more; or $1\times10^{20}$ or more). In some examples, the set of cavities 510 can comprise a plurality of cavities 510. In some examples, the set of cavities 510 comprises a plurality of cavities 510 in an ordered array.

Each of the set of cavities 510 has a longitudinal axis and a cross-sectional shape in a plane perpendicular to the longitudinal axis of said cavity 510, wherein the cross-sectional shape can be any shape, such as a regular shape, an irregular shape, an isotropic shape, or an anisotropic shape. In some examples, the cross-sectional shape of each of the set of cavities 510 can be substantially circular, ovate, ovoid, elliptic, triangular, rectangular, polygonal, etc. In some examples, the cross-sectional shape of each of the set of cavities 510 is substantially the same. In some examples, the cross-sectional shape of the set of cavities 510 can be substantially circular. In some examples, the cross-sectional shape of the set of cavities 510 can be substantially rectangular, as shown in FIG. 21-FIG. 22 and FIG. 29-FIG. 30.

In some examples, the longitudinal axis of each of the set of cavities 510 are substantially parallel to each other. In some examples, the longitudinal axis of each of the set of cavities 510 is substantially perpendicular to the bottom surface 504 of the patterned detection electrode 500 (e.g., such that the cross-sectional shape is in a plane substantially parallel to the bottom surface 504 of the patterned detection electrode 500).

The set of cavities 510 can have an average characteristic dimension. The term "characteristic dimension," as used herein refers to the largest straight line distance between two points in the plane of the cross-sectional shape of each of the cavities 510 (e.g., the diameter of a circular cross-sectional shape, the diagonal of a rectangular cross-sectional shape, the bisector of a triangular cross-sectional shape, etc.). "Average characteristic dimension" and "mean characteristic dimension" are used interchangeably herein, and generally refer to the statistical mean characteristic dimension of the cavities in a population of cavities. For example, for a cylindrical set of cavities 510, the cross-sectional shape can be substantially circular and the average characteristic dimension can refer to the average diameter. In some examples, the average characteristic dimension of the set of cavities 510 can be substantially the same for the entire thickness. In some examples, the average characteristic dimension of the set of cavities 510 can vary with the thickness (e.g., tapered or stepped).

The set of cavities 510 can, for example, have an average characteristic dimension of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of cavities 510 can have an average characteristic dimension of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average characteristic dimension of the set of cavities 510 can range from any of the minimum values described above to any of the maximum values described above. For example, the average characteristic dimension of the set of cavities 510 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of cavities 510 can comprise a plurality of cavities 510, wherein the average characteristic dimension of the plurality of cavities 510 can be substantially monodisperse. "Monodisperse" and "homogeneous characteristic dimension distribution," as used herein, and generally describe a population of cavities where all of the cavities have the same or nearly the same characteristic dimension. As used herein, a monodisperse distribution refers to distributions in which 80% of the distribution (e.g., 85% of the distribution, 90% of the distribution, or 95% of the distribution) lies within 25% of the mean characteristic dimension (e.g., within 20% of the mean characteristic dimension, within 15% of the mean characteristic dimension, within 10% of the mean characteristic dimension, or within 5% of the mean characteristic dimension).

In some examples, the patterned detection electrode 500 can comprise a set of protrusions 520 extending from the bottom surface 504. The set of protrusions 520 can be integrally formed with the patterned detection electrode 500.

As used herein, "a set of protrusions 520" and "the set of protrusions 520" are meant to include any number of protrusions 520 in any arrangement. Thus, for example, "a set of protrusions 520" includes one or more protrusions 520 (e.g., 2 or more; 3 or more; 4 or more; 5 or more; 10 or more; 15 or more; 20 or more; 25 or more; 30 or more; 40 or more; 50 or more; 75 or more; 100 or more; 150 or more; 200 or more; 250 or more; 300 or more; 400 or more; 500 or more; 750 or more; 1000 or more; 1500 or more; 2000 or more; 2500 or more; 3000 or more; 4000 or more; 5000 or more; 7500 or more; $1\times10^4$ or more; $2.5\times10^4$ or more; $5\times10^4$ or more; $7.5\times10^4$ or more; $1\times10^5$ or more; $2.5\times10^5$ or more; $5\times10^5$ or more; $7.5\times10^5$ or more; $1\times10^6$ or more; $5\times10^6$ or more; $1\times10^7$ or more; $5\times10^7$ or more; $1\times10^8$ or more; $5\times10^8$ or more; $1\times10^9$ or more; $5\times10^9$ or more; $1\times10^{10}$ or more; $1\times10^{11}$ or more; $1\times10^{12}$ or more; $1\times10^{13}$ or morel $1\times10^{14}$ or more; $1\times10^{15}$ or more; $1\times10^{16}$ or more; $1\times10^{17}$ or more; $1\times10^{18}$ or more; $1\times10^{19}$ or more; or $1\times10^{20}$ or more). In some examples, the set of protrusions 520 can comprise a plurality of protrusions 520. In some examples, the set of protrusions 520 comprises a plurality of protrusions 520 in an ordered array.

The set of protrusions 520 extending from the bottom surface 504 of the patterned detection electrode 500 can, independently, be any shape. For example, the set of protrusions 520 can, independently, be a polyhedron (e.g., a platonic solid, a prism, a pyramid), a cylinder, a hemicylinder, an elliptical cylinder, a hemi-elliptical cylinder, a sphere, a hemisphere, a cone, a semicone, etc.

Figure 23:
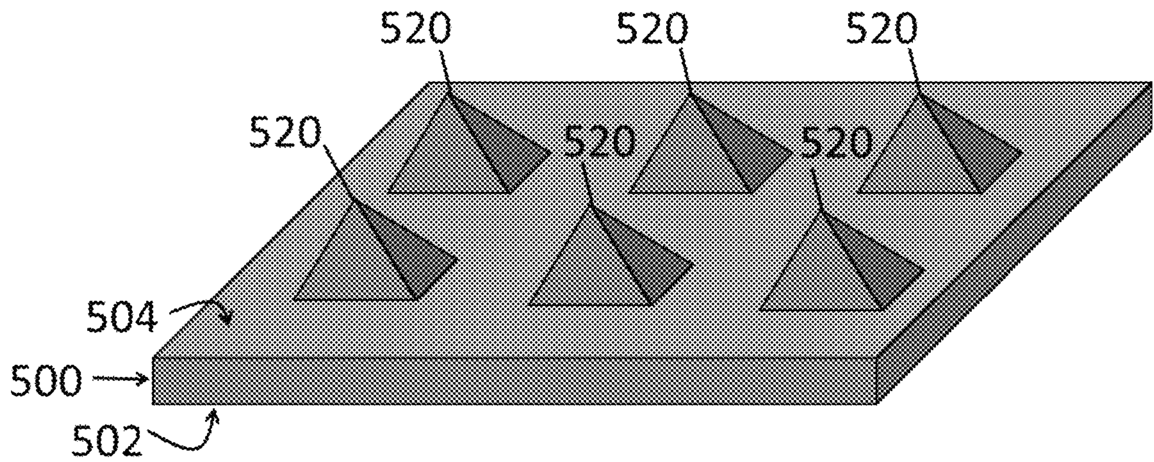
FIG. 23 is a schematic illustration of an example patterned detection electrode as disclosed herein according to one implementation.

In some examples, the set of protrusions 520 can, independently, be a platonic solid, a pyramid, a sphere, a hemisphere, a cone, a semicone, etc. In some examples, the set of protrusions 520 can, independently, be spherical, hemispherical, ellipsoidal, triangular, pyramidal, tetrahedral, cylindrical, rectangular, cuboidal, cuboctahedral, etc. Referring now to FIG. 23, the set of protrusions 520 can, for example, be pyramidal. The set of protrusions 520 can have an average size. The term "size," as used herein, refers to the largest straight line distance spanning the protrusion 520 in the plane of the bottom surface 504 of the patterned detection electrode 500. "Average size" and "mean size" are used interchangeably herein, and generally refer to the statistical mean size of the protrusions in a population of protrusions. For example, for a set of protrusions 520 having a substantially circular shape in the plane of bottom surface of the patterned detection electrode, the average size can refer to the average diameter.

The set of protrusions 520 can, for example, have an average size of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of protrusions 520 can have an average size of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average size of the set of protrusions 520 can range from any of the minimum values described above to any of the maximum values described above. For example, the average size of the set of protrusions 520 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of protrusions 520 can comprise a plurality of protrusions 520 wherein the average size of the plurality of protrusions 520 can be substantially monodisperse. "Monodisperse" and "homogeneous size distribution," as used herein, and generally describe a population of protrusions where all of the protrusions have the same or nearly the same average size. As used herein, a monodisperse distribution refers to distributions in which 80% of the distribution (e.g., 85% of the distribution, 90% of the distribution, or 95% of the distribution) lies within 25% of the average size (e.g., within 20% of the average size, within 15% of the average size, within 10% of the average size, or within 5% of the average size).

In some examples, each of the protrusions 520 can have a longitudinal axis, a first surface, and a second surface opposite and axially spaced apart from the first surface. The first surface and the second surface can, independently, be planar (e.g., flat) or non-planar (e.g., pyramidal, hemispherical, conical, etc.). In some examples, the longitudinal axis of each of the protrusions 520 are substantially parallel to each other.

The longitudinal axis of each of the protrusions 520 can have an average length, wherein the average length is 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, 9 mm or more, 10 mm or more, 15 mm or more, 20 mm or more, 25 mm or more, 30 mm or more, 35 mm or more, 40 mm or more, 45 mm or more, 50 mm or more, 60 mm or more, 70 mm or more, 80 mm or more, 90 mm or more, 100 mm or more, 125 mm or more, 150 mm or more, 175 mm or more, 200 mm or more, 225 mm or more, 250 mm or more, or 275 mm or more). In some examples, the average length of the longitudinal axis of the set of protrusions 520 can be 300 millimeters (mm) or less (e.g., 275 mm or less, 250 mm or less, 225 mm or less, 200 mm or less, 175 mm or less, 150 mm or less, 125 mm or less, 100 mm or less, 90 mm or less, 80 mm or less, 70 mm or less, 60 mm or less, 50 mm or less, 45 mm or less, 40 mm or less, 35 mm or less, 30 mm or less, 25 mm or less, 20 mm or less, 15 mm or less, 10 mm or less, 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average length of the longitudinal axis of the set of protrusions 520 can range from any of the minimum values described above to any of the maximum values described above. For example, the average length of the longitudinal axis of the set of protrusions 520 can be from 1 micrometer (nm) to 300 millimeters (mm) (e.g., from 1 nm to 1 μm, from 1 μm to 100 μm, from 100 μm to 10 mm, from 10 mm to 300 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 10 mm to 150 mm, from 150 mm to 300 mm, from 1 nm to 100 mm, from 10 nm to 300 mm, or from 10 nm to 100 mm).

In some examples, the set of protrusions 520 can comprise a plurality of protrusions wherein the average length of the longitudinal axis of the plurality of protrusions 520 can be substantially monodisperse. "Monodisperse" and "homogeneous length distribution," as used herein, and generally describe a population of protrusions where all of the protrusions have the same or nearly the same average longitudinal axis length. As used herein, a monodisperse distribution refers to distributions in which 80% of the distribution (e.g., 85% of the distribution, 90% of the distribution, or 95% of the distribution) lies within 25% of the average length (e.g., within 20% of the average length, within 15% of the average length, within 10% of the average length, or within 5% of the average length).

Each of the protrusions 520 can have a cross-sectional shape in a plane perpendicular to the longitudinal axis, wherein the cross-sectional shape can be any shape, such as a regular shape, an irregular shape, an isotropic shape, or an anisotropic shape. In some examples, the cross-sectional shape of each of the set of protrusions can be substantially circular, ovate, ovoid, elliptic, triangular, rectangular, polygonal, etc. In some examples, the cross-sectional shape of each of the set of protrusions 520 is substantially the same.

The set of protrusions 520 can have an average characteristic dimension. The term "characteristic dimension," as used herein refers to the largest straight line distance between two points in the plane of the cross-sectional shape of each of the protrusions. "Average characteristic dimension" and "mean characteristic dimension" are used interchangeably herein, and generally refer to the statistical mean characteristic dimension of the protrusions in a population of protrusions. For example, for a cylindrical set of second protrusions, the cross-sectional shape can be substantially circular and the average characteristic dimension can refer to the average diameter.

The set of protrusions 520 can, for example, have an average characteristic dimension of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of protrusions 520 can have an average characteristic dimension of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average characteristic dimension of the set of protrusions 520 can range from any of the minimum values described above to any of the maximum values described above. For example, the average characteristic dimension of the set of protrusions 520 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of protrusions 520 can comprise a plurality of protrusions wherein the average characteristic dimension of the plurality of protrusions 520 can be substantially monodisperse. "Monodisperse" and "homogeneous characteristic dimension distribution," as used herein, and generally describe a population of protrusions where all of the protrusions have the same or nearly the same average characteristic dimension. As used herein, a monodisperse distribution refers to distributions in which 80% of the distribution (e.g., 85% of the distribution, 90% of the distribution, or 95% of the distribution) lies within 25% of the average characteristic dimension (e.g., within 20% of the average characteristic, within 15% of the average characteristic dimension, within 10% of the average characteristic dimension, or within 5% of the average characteristic dimension).

In some examples, the set of protrusions 520 can, independently, be a prism (e.g., a triangular prism, rectangular prism, polygonal prism), a cylinder, a hemicylinder, an elliptical cylinder, a hemi-elliptical cylinder, etc.

Figure 24:
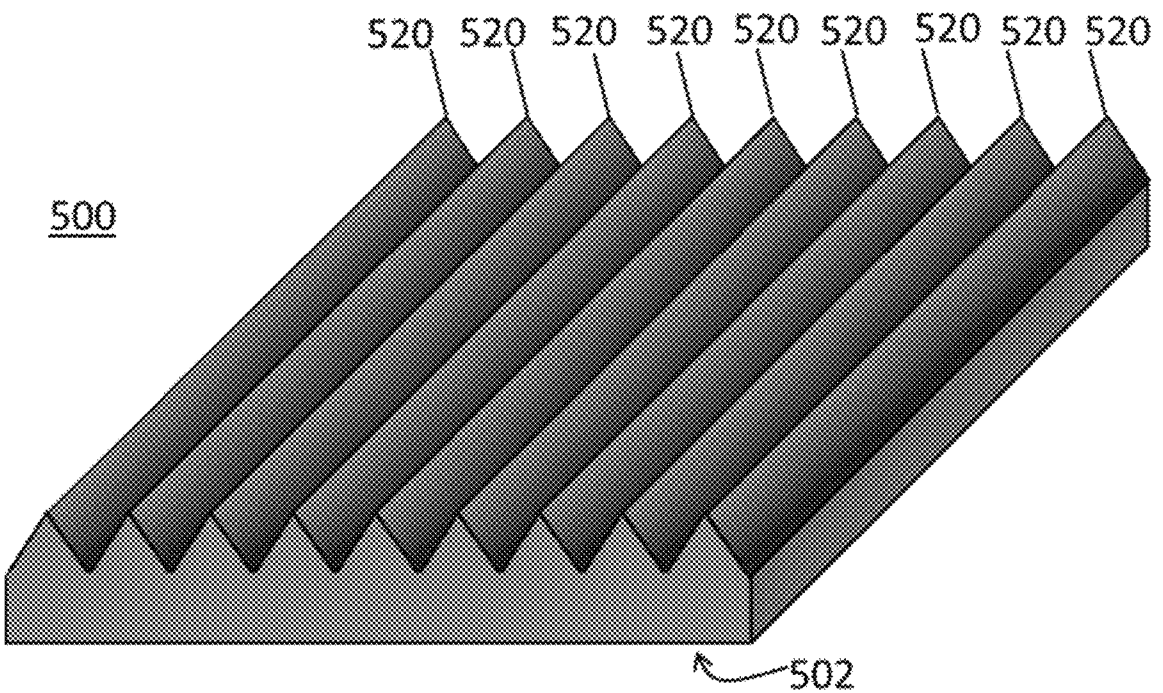
FIG. 24 is a schematic illustration of an example patterned detection electrode as disclosed herein according to one implementation.
Figure 25:
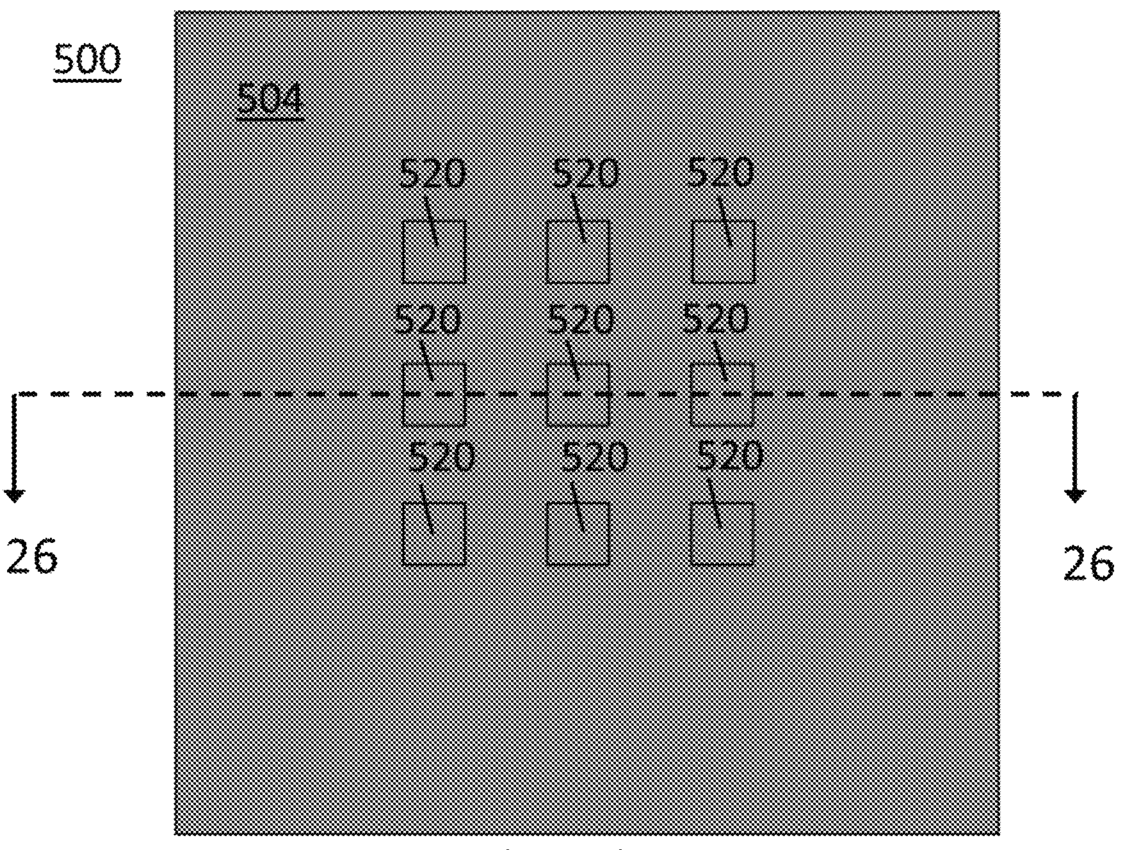
FIG. 25 is a schematic plan view of an example patterned detection electrode as disclosed herein according to one implementation.
Figure 26:
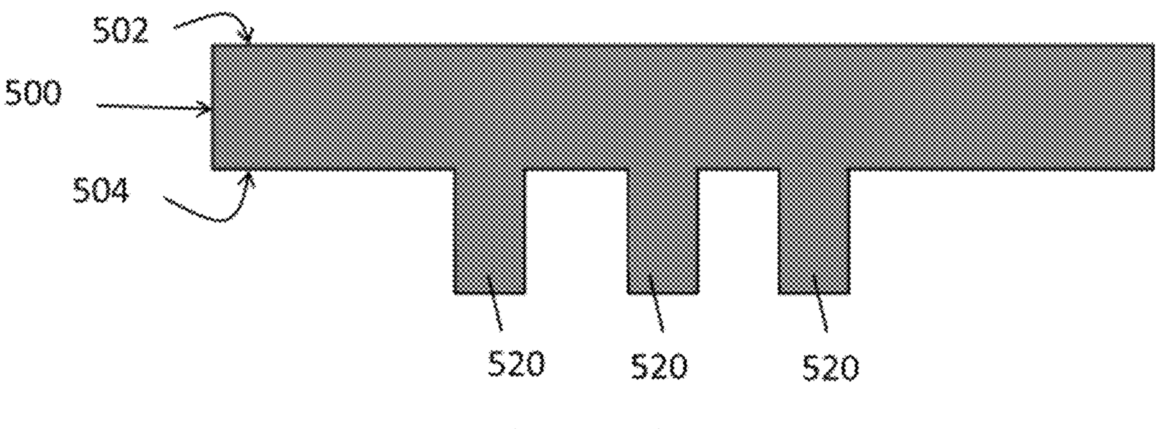
FIG. 26 is a cross-sectional plan view along 26-26 in FIG. 25 of the example patterned detection electrode.
Figure 27:
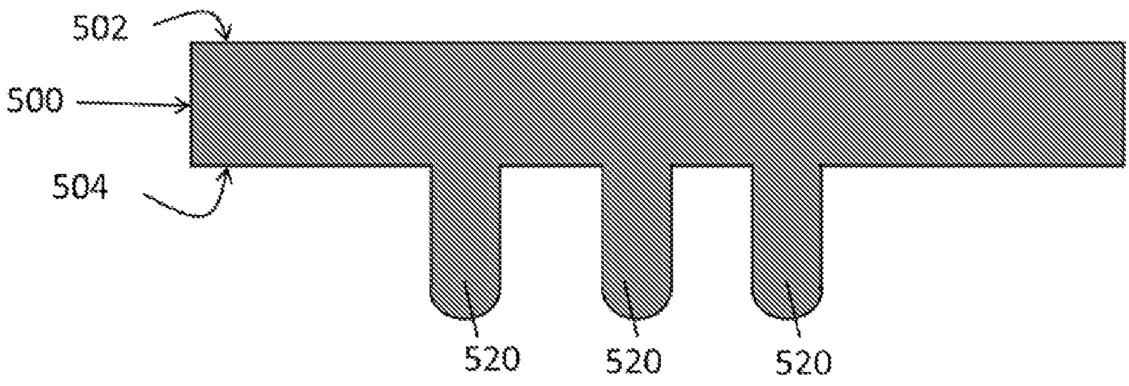
FIG. 27 is a cross-sectional plan view of an example patterned detection electrode.

In some examples, the longitudinal axis of each of the protrusions 520 is substantially parallel to the bottom surface 504 of the patterned detection electrode 500. For example, the longitudinal axis of each of the protrusions 520 is substantially parallel to the bottom surface 504 of the patterned detection electrode 500 such that the bottom surface 504 of the patterned detection electrode 500 is corrugated, grooved, ridged, etc. Referring now to FIG. 24, the set of protrusions 520 can, for example, be triangular prisms having a longitudinal axis substantially parallel to the bottom surface 504 of the patterned detection electrode 500.

Figure 28:
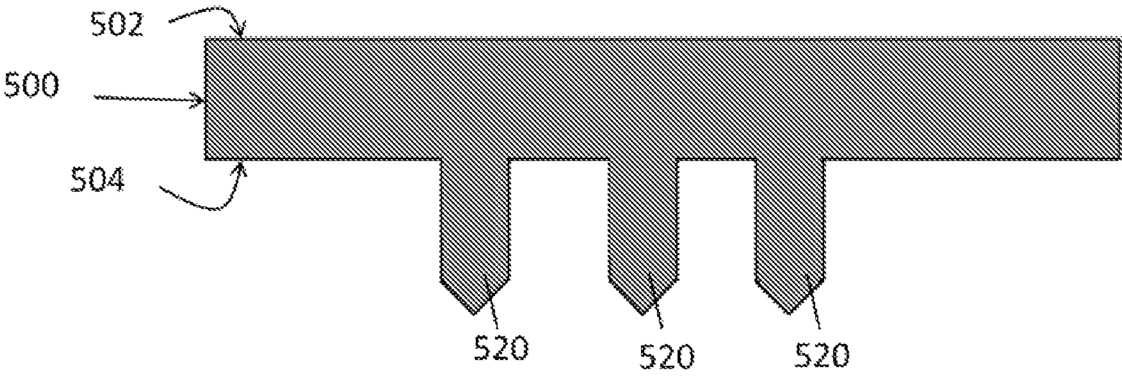
FIG. 28 is a cross-sectional plan view of an example patterned detection electrode.

In some examples, the first surface of the protrusions 520 is planar and the longitudinal axis of each of the protrusions 520 is substantially perpendicular to the bottom surface 504 of the patterned detection electrode 500, such that the set of protrusions 520 extend from the first surface at the bottom surface 504 of the patterned detection electrode 500 along the longitudinal axis to the second surface. The second surface can be planar (e.g., flat) or non-planar (e.g., pyramidal, hemispherical, conical, etc.). Referring now to FIG. 25-FIG. 30, the protrusions 520 can, for example, be rectangular prisms having a planar second surface (FIG. 26 and FIG. 30), a hemispherical second surface (FIG. 27), and/or a pyramidal second surface (FIG. 28).

Figure 29:
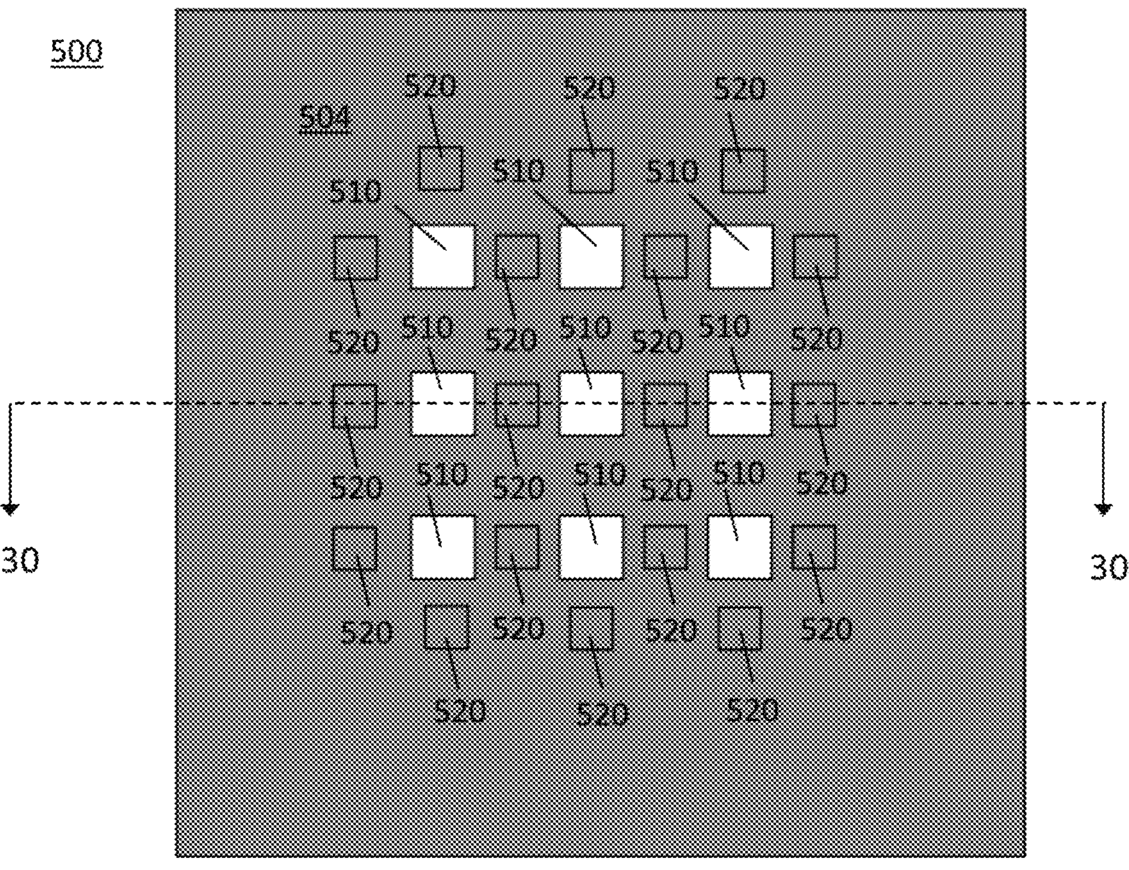
FIG. 29 is a schematic plan view of an example patterned detection electrode as disclosed herein according to one implementation.
Figure 30:
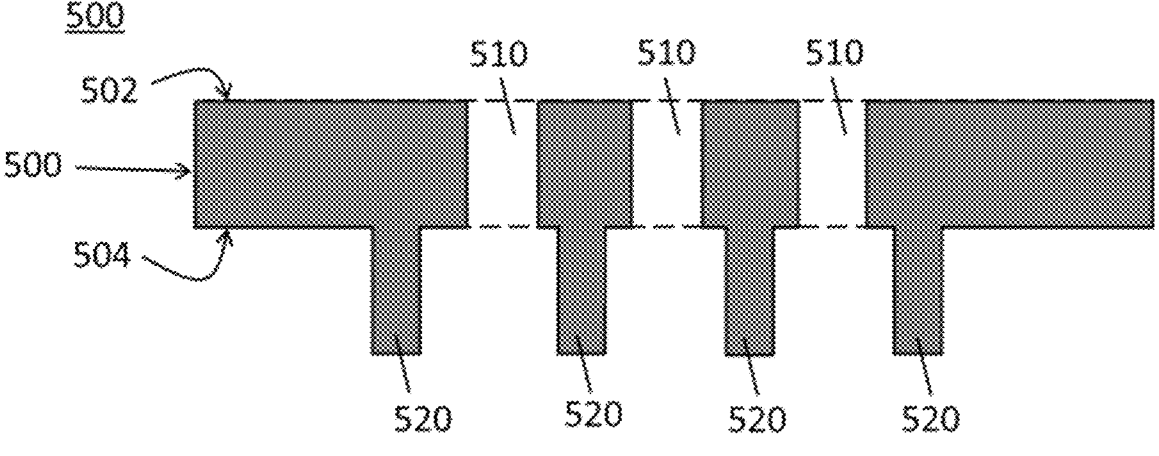
FIG. 30 is a cross-sectional plan view along 30-30 in FIG. 29 of the example patterned detection electrode.

In some examples, the patterned detection electrode 500 comprises a set of cavities 510 and a set of protrusions 520, wherein each of the cavities 510 perforates the patterned detection electrode 500 from the top surface 502 to the bottom surface 504, and wherein each protrusion extends from the bottom surface 504, for example as shown in FIG. 29-FIG. 30.

Figure 57:
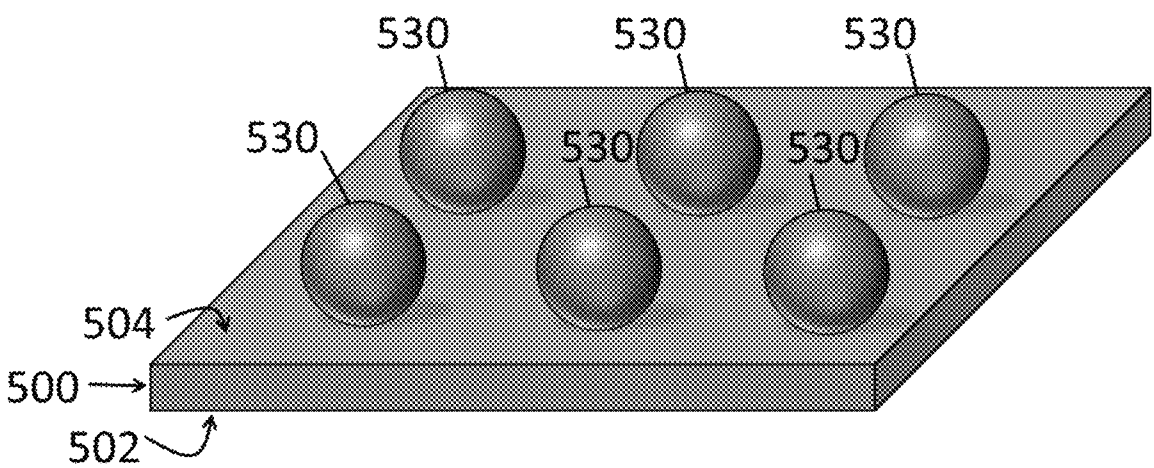
FIG. 57 is a schematic illustration of an example patterned detection electrode as disclosed herein according to one implementation.

In some examples, the patterned detection electrode 500 can comprise a set of particles 530 disposed on the bottom surface 504 (FIG. 57). As used herein, "a set of particles 530" and "the set of particles 530" are meant to include any number of particles 530 in any arrangement. Thus, for example, "a set of particles 530" includes one or more particles 530 (e.g., 2 or more; 3 or more; 4 or more; 5 or more; 10 or more; 15 or more; 20 or more; 25 or more; 30 or more; 40 or more; 50 or more; 75 or more; 100 or more; 150 or more; 200 or more; 250 or more; 300 or more; 400 or more; 500 or more; 750 or more; 1000 or more; 1500 or more; 2000 or more; 2500 or more; 3000 or more; 4000 or more; 5000 or more; 7500 or more; $1\times10^4$ or more; $2.5\times10^4$ or more; $5\times10^4$ or more; $7.5\times10^4$ or more; $1\times10^5$ or more; $2.5\times10^5$ or more; $5\times10^5$ or more; $7.5\times10^5$ or more; $1\times10^6$ or more; $5\times10^6$ or more; $1\times10^7$ or more; $5\times10^7$ or more; $1\times10^8$ or more; $5\times10^8$ or more; $1\times10^9$ or more; $5\times10^9$ or more; $1\times10^{10}$ or more; $1\times10^{11}$ or more; $1\times10^{12}$ or more; $1\times10^{13}$ or morel $1\times10^{14}$ or more; $1\times10^{15}$ or more; $1\times10^{16}$ or more; $1\times10^{17}$ or more; $1\times10^{18}$ or more; $1\times10^{19}$ or more; or $1\times10^{20}$ or more). In some examples, the set of particles 530 can comprise a plurality of particles 530. In some examples, the set of particles 530 comprises a plurality of particles 530 in an ordered array.

The set of particles 530 can, for example, comprise a transparent conducting oxide, a metal oxide, a conducting polymer, a carbon material, a metal, or a combination thereof. In some examples, the set of particles 530 can comprise a metal, carbon nanotubes, doped silicon, a conductive ink, or a combination thereof.

The set of particles 530 can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. As used herein, the size of a particle can refer to the largest linear distance between two points on the surface of the particle. For an anisotropic particle, the average particle size can refer to, for example, the average maximum dimension of the particle (e.g., the length of a rod shaped particle, the diagonal of a cube shape particle, the bisector of a triangular shaped particle, etc.). Mean particle size can be measured using methods known in the art, such as evaluation by electron microscopy.

The set of particles 530 can have an average particle size of 1 nanometer (nm) or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeter (mm) or more, 1.25 mm or more, 1.5 mm or more, 1.75 mm or more, 2 mm or more, 2.25 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the set of particles 530 can have an average particle size of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2.25 mm or less, 2 mm or less, 1.75 mm or less, 1.5 mm or less, 1.25 mm or less, 1 mm or less, 900 micrometer (μm) or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 900 nanometers (nm) or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average particle size of the set of particles 530 can range from any of the minimum values described above to any of the maximum values described above. For example, the average particle size of the set of particles 530 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

In some examples, the set of particles 530 can comprise a plurality of particles which can be substantially monodisperse. "Monodisperse" and "homogeneous size distribution," as used herein, and generally describe a population of particles where all of the particles have the same or nearly the average particle size. As used herein, a monodisperse distribution refers to particle distributions in which 80% of the distribution (e.g., 85% of the distribution, 90% of the distribution, or 95% of the distribution) lies within 25% of the average particle size (e.g., within 20% of the average particle size, within 15% of the average particle size, within 10% of the average particle size, or within 5% of the average particle size).

The set of particles 530 can be of any shape (e.g., a sphere, a rod, a quadrilateral, an ellipse, a triangle, a polygon, etc.). In some examples, the set of particles 530 can have an isotropic shape. In some examples, the set of particles 530 can have an anisotropic shape.

The detection electrode 500 is disposed opposite and spaced apart from the pyroelectric layer 400 by a distance 610. The distance 610 can, for example be 1 nanometer (nm) or more (e.g., 2 nm or more, 3 nm or more, 4 nm or more, 5 nm or more, 10 nm or more, 15 nm or more, 20 nm or more, 25 nm or more, 30 nm or more, 40 nm or more, 50 nm or more, 75 nm or more, 100 nm or more, 125 nm or more, 150 nm or more, 200 nm or more, 250 nm or more, 300 nm or more, 400 nm or more, 500 nm or more, 750 nm or more, 1 micrometer (micron, μm) or more, 1.25 μm or more, 1.5 μm or more, 2 μm or more, 2.5 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the distance 610 can be 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4.5 μm or less, 4 μm or less, 3.5 μm or less, 3 μm or less, 2.5 μm or less, 2 μm or less, 1.5 μm or less, 1 μm or less, 1.25 μm or less, 750 nanometers (nm) or less, 500 nm or less, 400 nm or less, 300 nm or less, 250 nm or less, 200 nm or less, 150 nm or less, 125 nm or less, 100 nm or less, 75 nm or less, 50 nm or less, 40 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The distance 610 can range from any of the minimum values described above to any of the maximum values described above. For example, the distance 610 can be from 1 nanometer (nm) to 10 millimeters (mm) (e.g., from 1 nm to 1 μm, from 1 μm to 100 μm, from 100 μm to 10 mm, from 1 nm to 10 nm, from 10 nm to 100 nm, from 100 nm to 1 μm, from 1 μm to 10 μm, from 10 μm to 100 μm, from 100 μm to 1 mm, from 1 mm to 10 mm, from 1 nm to 1 mm, from 10 nm to 10 mm, or from 10 nm to 1 mm).

Figure 31:
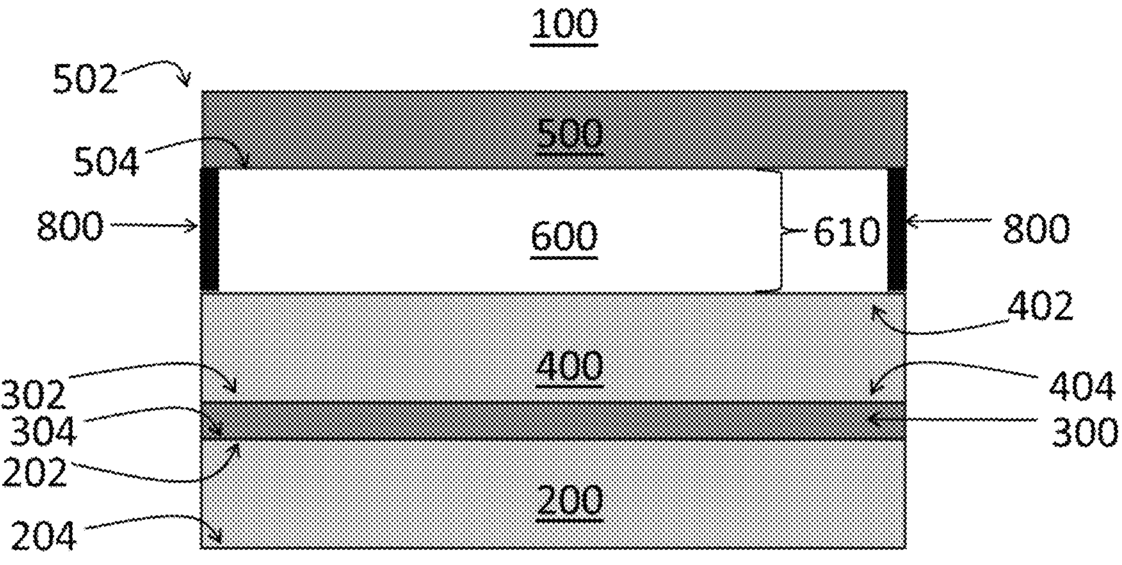
FIG. 31 is a schematic plan view of an example device as disclosed herein according to one implementation.

Referring now to FIG. 31, the devices 100, in some examples, can further comprise a means 800 for controlling and/or adjusting the distance 610. For example, the means 800 for controlling and/or adjusting the distance 610 can comprise a means for raising and/or lowering the detection electrode 500 relative to the pyroelectric layer 400 to thereby adjust and/or control the distance 610.

In some examples, the means 800 for controlling the distance 610 can comprise a spacer having a thickness, wherein the thickness of the spaced controls the distance 610. The spacer can comprise any material consistent with the methods, devices, and systems disclosed herein. In some examples, the spacer can comprise a dielectric, a semiconductor, a ceramic, a transparent conducing oxide, a polymer, a metal, or a combination thereof. In some examples, the spacer can comprise a metal. In some examples, the spacer can comprise a dielectric. The material of the spacer can be selected in view of a variety of factors, for example to achieve a desired result.

Figure 32:
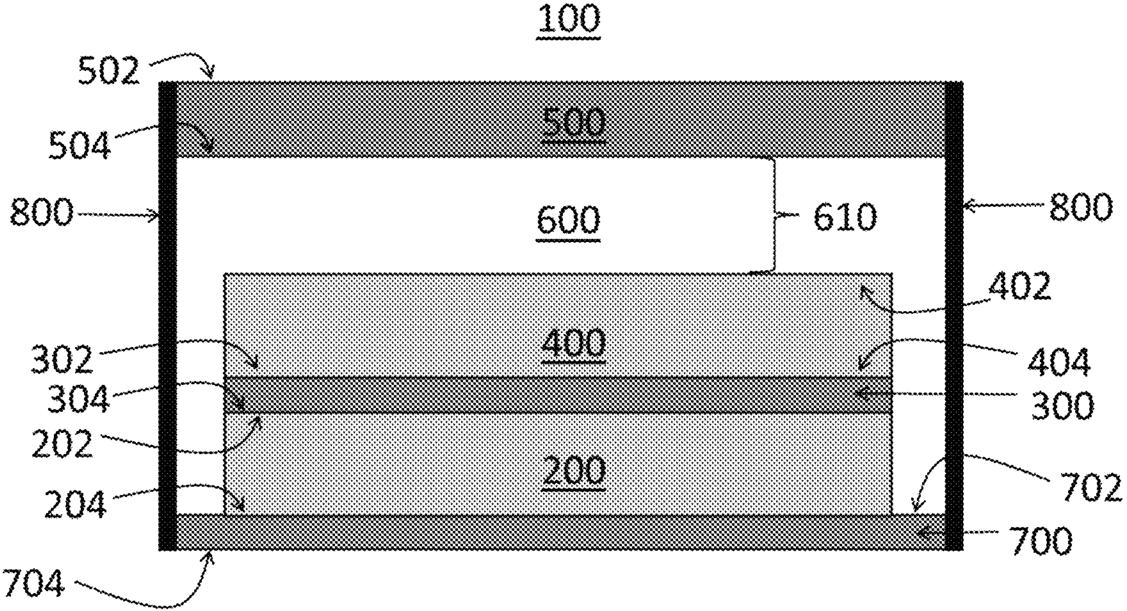
FIG. 32 is a schematic plan view of an example device as disclosed herein according to one implementation.

Referring now to FIG. 32, the devices 100, in some examples, can further comprise a first substrate 700, wherein the temperature control layer 200 is disposed on the first substrate 700. In some examples, the temperature control layer 200 is bonded to the first substrate 700. For example, temperature control layer 200 can be bonded to the first substrate 700 via adhesive bonding (e.g., via an appropriate glue or other adhesive, such as a thermal adhesive), anodic bonding, thermocompression bonding, fusion bonding, eutectic bonding, direct bonding, complex oxide bonding, metallic bonding, or a combination thereof. In some examples, the means 800 for adjusting the distance 610 can be coupled to the first substrate 700 and the detection electrode 500.

The first substrate 700 has a top surface 702 and a bottom surface 704 opposite and spaced apart from the top surface 702. In some examples, the top surface 702 and the bottom surface 704 of the first substrate are substantially parallel to each other. The temperature control layer 200 is, for example, disposed on the first substrate 700 such that the bottom surface 204 of the temperature control layer 200 is disposed on the top surface 702 of the first substrate 700. In some examples, the bottom surface 204 of the temperature control layer 200 can be bonded to the top surface 702 of the first substrate 700. In some examples, the top surface 702 and the bottom surface 704 of the first substrate 700 and the top surface 202 and the bottom surface 204 of the temperature control layer 200 are all substantially parallel to each other. In some examples, the top surface 702 and the bottom surface 704 of the first substrate 700; the top surface 502 and the bottom surface 504 of the detection electrode 500; the top surface 402 and the bottom surface 404 of the pyroelectric layer 400; the top surface 302 and the bottom surface 304 of the grounded electrode 300; and the top surface 202 and the bottom surface 204 of the temperature control layer 200 are all substantially parallel to each other.

The first substrate 700 can comprise any material consistent with the methods, devices, and systems disclosed herein. In some examples, the first substrate 700 can comprise a dielectric, a semiconductor, a ceramic, a transparent conducing oxide, a polymer, a metal, or a combination thereof. In some examples, the first substrate 700 is thermally conductive and the temperature control layer 200 is in thermal contact with the first substrate 700.

The first substrate 700 has an average thickness, the average thickness being the average dimension from the top surface 702 to the bottom surface 704. The average thickness of the first substrate 700 can, for example, be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the average thickness of the first substrate 700 can be 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average thickness of the first substrate 700 can range from any of the minimum values described above to any of the maximum values described above. For example, the average thickness of the first substrate 700 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 702 and the bottom surface 704 of the first substrate 700 can, independently, be any shape. In some examples, the top surface 702 and the bottom surface 704 of the first substrate 700 can, independently, be substantially circular, ovate, ovoid, elliptic, triangular, rectangular, polygonal, etc. In some examples, the top surface 702 and the bottom surface 704 of the first substrate 700 can be substantially the same shape.

The first substrate 700 has average lateral dimension (e.g., diameter when the first substrate 700 is circular; diagonal when the first substrate 700 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the first substrate 700 can be 300 millimeters (mm) or less (e.g., 275 mm or less, 250 mm or less, 225 mm or less, 200 mm or less, 175 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the first substrate 700 can range from any of the minimum values described above to any of the maximum values described above. For example, the average lateral dimension of the first substrate 700 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm).

Figure 33:
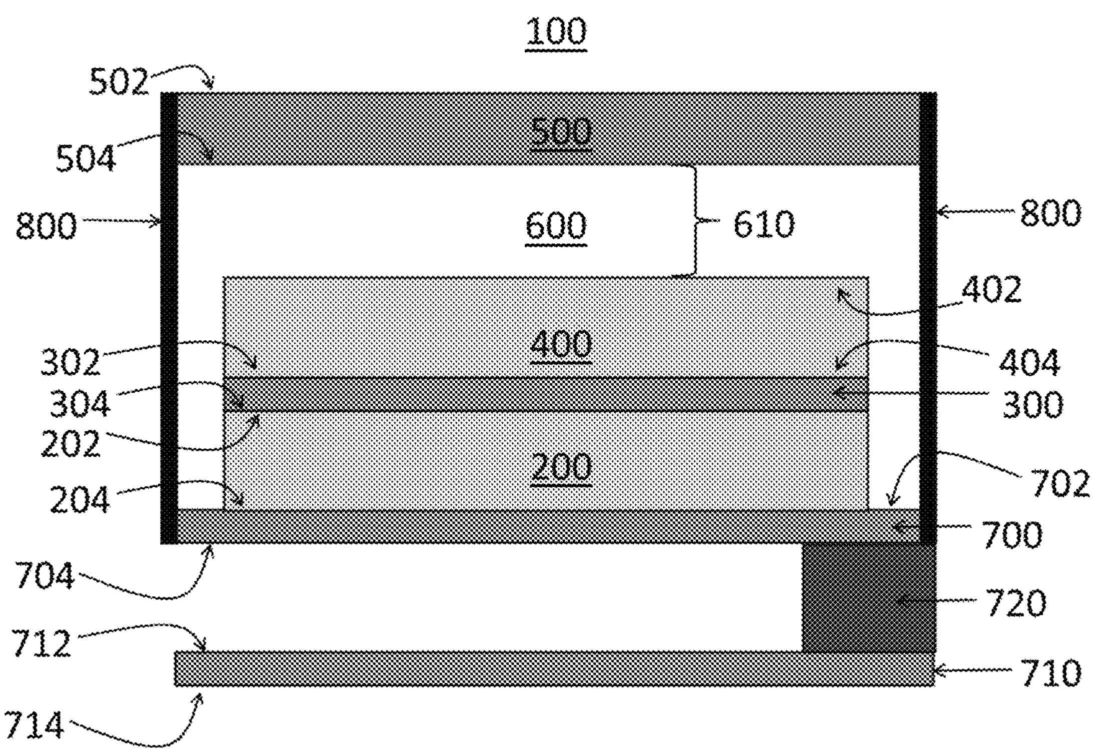
FIG. 33 is a schematic plan view of an example device as disclosed herein according to one implementation.

Referring now to FIG. 33, the device 100 can, in some examples, further comprises a second substrate 710 and a fluid flow control device 720, wherein the second substrate 710 is disposed opposite and spaced apart from the first substrate 700 and the fluid flow control device 720 is disposed between the first substrate 700 and the second substrate 710, such that the fluid flow control device 720 is sandwiched by the first substrate 700 and the second substrate 710. The fluid flow control device 720 can control the flow of a fluid (e.g., a gas, such as air, or a liquid, such as water) to thereby adjust and/or control dissipation of heat from temperature control layer 200.

In some examples, the fluid flow control device 720 can comprise an air flow control device, such as a fan, a blower, etc. In some examples, the fluid flow control device 720 can comprise a channel or tubing through which the fluid can flow, such as a microfluidic channel. In some examples, the fluid flow control device 720 can further comprise a pump or syringe fluidly connected to the channel or tubing to control the flow of the fluid through the tubing.

The second substrate 710 has a top surface 712 and a bottom surface 714 opposite and spaced apart from the top surface 712. In some examples, the top surface 712 and the bottom surface 714 of the second substrate 710 are substantially parallel to each other. In some examples, the top surface 712 and the bottom surface 714 of the second substrate 710 and the top surface 702 and the bottom surface 704 of the first substrate 700 are all substantially parallel to each other. In some examples, the top surface 712 and the bottom surface 714 of the second substrate; the top surface 702 and the bottom surface 704 of the first substrate 700; the top surface 502 and the bottom surface 504 of the detection electrode 500; the top surface 402 and the bottom surface 404 of the pyroelectric layer 400; the top surface 302 and the bottom surface 304 of the grounded electrode 300; and the top surface 202 and the bottom surface 204 of the temperature control layer 200 are all substantially parallel to each other.

The second substrate 710 can comprise any material consistent with the methods, devices, and systems disclosed herein. In some examples, the second substrate 710 can comprise a dielectric, a semiconductor, a ceramic, a transparent conducing oxide, a polymer, a metal, or a combination thereof.

The second substrate 710 has an average thickness, the average thickness being the average dimension from the top surface 712 to the bottom surface 714. The average thickness of the second substrate 710 can, for example be 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the average thickness of the second substrate 710 can be 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average thickness of the second substrate 710 can range from any of the minimum values described above to any of the maximum values described above. For example, the average thickness of the second substrate 710 can be from 1 micrometer (micron, μm) to 10 millimeters (mm) (e.g., from 1 μm to 100 μm, from 100 μm to 10 mm, from 1 μm to 10 μm, from 10 μm to 100 μm, from 100 μm to 1 mm, from 1 mm to 10 mm, from 1 μm to 1 mm, from 10 μm to 10 mm, or from 10 μm to 1 mm).

The top surface 712 and the bottom surface 714 of the second substrate 710 can, independently, be any shape. In some examples, the top surface 712 and the bottom surface 714 of the second substrate 710 can, independently, be substantially circular, ovate, ovoid, elliptic, triangular, rectangular, polygonal, etc. In some examples, the top surface 712 and the bottom surface 714 of the second substrate 710 can be substantially the same shape.

The second substrate 710 has average lateral dimension (e.g., diameter when the second substrate 710 is circular;

diagonal when the second substrate 710 is substantially rectangular, etc.) of 1 micrometer (micron, μm) or more (e.g., 2 μm or more, 3 μm or more, 4 μm or more, 5 μm or more, 10 μm or more, 15 μm or more, 20 μm or more, 25 μm or more, 30 μm or more, 40 μm or more, 50 μm or more, 75 μm or more, 100 μm or more, 125 μm or more, 150 μm or more, 200 μm or more, 250 μm or more, 300 μm or more, 400 μm or more, 500 μm or more, 750 μm or more, 1 millimeter (mm) or more, 1.25 mm or more, 1.5 mm or more, 2 mm or more, 2.5 mm or more, 3 mm or more, 4 mm or more, 5 mm or more, 10 mm or more, 15 mm or more, 20 mm or more, 25 mm or more, 30 mm or more, 40 mm or more, 50 mm or more, 75 mm or more, 100 mm or more, 125 mm or more, 150 mm or more, 200 mm or more, or 250 mm or more). In some examples, the average lateral dimension of the second substrate 710 can be 300 millimeters (mm) or less (e.g., 275 mm or less, 250 mm or less, 225 mm or less, 200 mm or less, 175 mm or less, 150 mm or less, 125 mm or less, 100 mm or less, 75 mm or less, 50 mm or less, 40 mm or less, 30 mm or less, 25 mm or less, 20 mm or less, 15 mm or less, 10 mm or less, 5 mm or less, 4 mm or less, 3 mm or less, 2.5 mm or less, 2 mm or less, 1.5 mm or less, 1.25 mm or less, 1 mm or less, 750 micrometer (μm) or less, 500 μm or less, 400 μm or less, 300 μm or less, 250 μm or less, 200 μm or less, 150 μm or less, 125 μm or less, 100 μm or less, 75 μm or less, 50 μm or less, 40 μm or less, 30 μm or less, 25 μm or less, 20 μm or less, 15 μm or less, 10 μm or less, 5 μm or less, 4 μm or less, 3 μm or less, or 2 μm or less). The average lateral dimension of the second substrate 710 can range from any of the minimum values described above to any of the maximum values described above. For example, the average lateral dimension of the second substrate 710 can be from 1 micrometer (μm) to 300 millimeters (mm) (e.g., from 1 μm to 100 μm, from 100 μm to 10 mm, from 10 mm to 300 mm, from 1 μm to 10 μm, from 10 μm to 100 μm, from 100 μm to 1 mm, from 1 mm to 10 mm, from 10 mm to 150 mm, from 150 mm to 300 mm, from 1 μm to 100 mm, from 1 μm to 50 mm, from 1 μm to 10 mm, from 10 μm to 300 mm, from 100 μm to 300 mm, from 1 mm to 300 mm, from 25 mm to 300 mm, or from 10 μm to 100 mm).

In some examples, the devices can further comprise a housing encasing the device, wherein the housing has an inlet and an outlet, such that a gas can be introduced into the ionization zone via the inlet. The housing can comprise any material consistent with the methods, devices, and systems disclosed herein. In some examples, the housing can comprise a dielectric, a polymer, or a combination thereof. In some examples, the detection electrode 500 can be disposed on the housing or integrally formed with the housing.

In some examples, the devices can further comprise an amplifier coupled to the detection electrode. The amplifier can be configured to amplify an electromagnetic or electrical signal detected by the detection electrode. Examples of amplifiers include, but are not limited to, transimpedance amplifiers (TIA), precision switched integrator transimpedance amplifiers, operational amplifiers, instrumentation amplifiers, low pass filters, high pass filters, bandpass filters, and combinations thereof.

In some examples, the devices can further comprise a temperature sensor, wherein the temperature sensor can be configured to measure the temperature of the pyroelectric layer.

In some examples, the devices can further comprise a pressure sensor, wherein the pressure sensor can be configured to measure the pressure (e.g., the air or vapor pressure) in the ionization region.

In some examples, the devices can further comprise a humidity sensor, wherein the humidity sensor can be configured to measure the humidity level in the ionization region.

In some examples, the devices can further comprise a computing device 1040. The computing device can, for example, be configured to: receive and process electromagnetic signals from the detection electrode; control the temperature of the temperature control layer; or a combination thereof.

Figure 34:
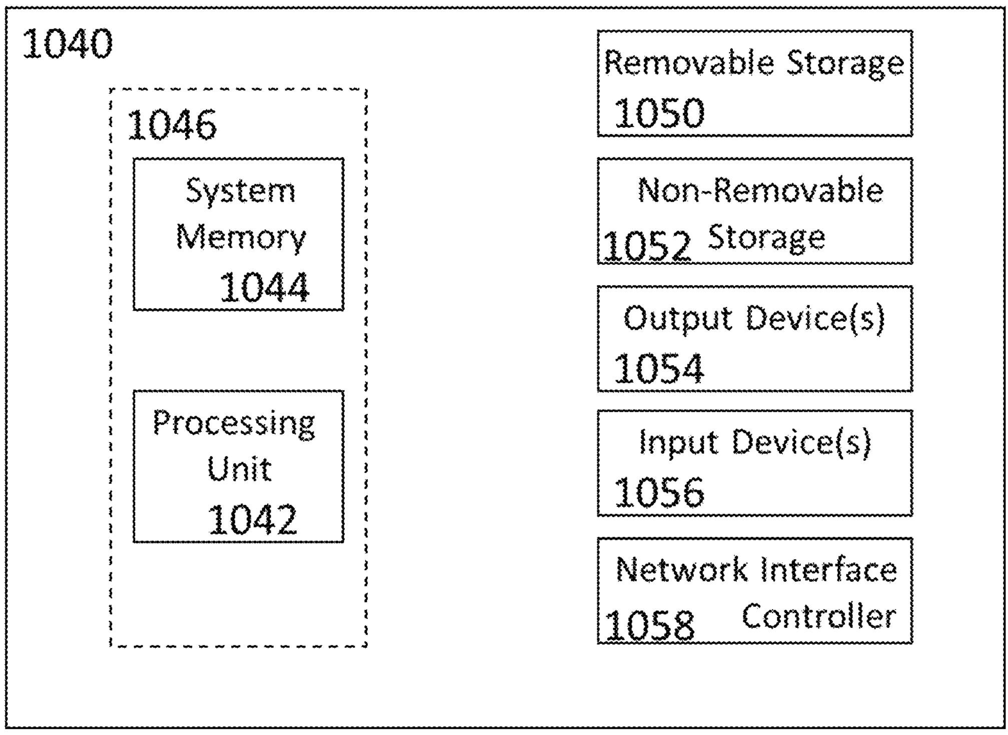
FIG. 34 is a schematic illustration of an example computing device.

FIG. 34 illustrates an example computing device 1040 upon which examples disclosed herein may be implemented. The computing device 1040 can include a bus or other communication mechanism for communicating information among various components of the computing device 1040. In its most basic configuration, computing device 1040 typically includes at least one processing unit 1042 (a processor) and system memory 1044. Depending on the exact configuration and type of computing device, system memory 1044 may be volatile (such as random access memory (RAM)), non-volatile (such as read-only memory (ROM), flash memory, etc.), or some combination of the two. This most basic configuration is illustrated in FIG. 34 by a dashed line 1046. The processing unit 1042 may be a standard programmable processor that performs arithmetic and logic operations necessary for operation of the computing device 1040.

The computing device 1040 can have additional features/functionality. For example, computing device 1040 may include additional storage such as removable storage 1050 and non-removable storage 1052 including, but not limited to, magnetic or optical disks or tapes. The computing device 1040 can also contain network connection(s) 1058 that allow the device to communicate with other devices. The computing device 1040 can also have input device(s) 1056 such as a keyboard, mouse, touch screen, antenna or other systems configured to communicate with the camera in the system described above, etc. Output device(s) 1054 such as a display, speakers, printer, etc. may also be included. The additional devices can be connected to the bus in order to facilitate communication of data among the components of the computing device 1040.

The processing unit 1042 can be configured to execute program code encoded in tangible, computer-readable media. Computer-readable media refers to any media that is capable of providing data that causes the computing device 1040 (i.e., a machine) to operate in a particular fashion. Various computer-readable media can be utilized to provide instructions to the processing unit 1042 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media, and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1042 can execute program code stored in the system memory 1044. For example, the bus can carry data to the system memory 1044, from which the processing unit 1042 receives and executes instructions. The data received by the system memory 1044 can optionally be stored on the removable storage 1050 or the non-removable storage 1052 before or after execution by the processing unit 1042.

The computing device 1040 typically includes a variety of computer-readable media. Computer-readable media can be any available media that can be accessed by device 1040 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1044, removable storage 1050, and non-removable storage 1052 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1040. Any such computer storage media can be part of computing device 1040.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, the device 100 comprises a computing device 1040 comprising a processor 1042 and a memory 1044 operably coupled to the processor 1042, the memory 1044 having further computer-executable instructions stored thereon that, when executed by the processor 1042, cause the processor 1042 to: receive an electromagnetic signal captured by the detection electrode; process the electromagnetic signal to determine a property; and output the property. The electromagnetic signal captured by the detection electrode can, for example, comprise the ionization current, amplified voltage, or a combination thereof.

In certain examples, the device 100 comprises a computing device 1040 comprising a processor 1042 and a memory 1044 operably coupled to the processor 1042, the memory 1044 having further computer-executable instructions stored thereon that, when executed by the processor 1042, cause the processor 1042 to: send an electromagnetic signal to the power source to thereby heat or cool the temperature control layer to a temperature at a rate, which induces a potential in the pyroelectric layer via the pyroelectric effect.

In certain examples, the device 100 comprises a computing device 1040 comprising a processor 1042 and a memory 1044 operably coupled to the processor 1042, the memory 1044 having further computer-executable instructions stored thereon that, when executed by the processor 1042, cause the processor 1042 to: receive an electromagnetic signal from the pressure sensor (when present), humidity sensor (when present), amplifier (when present), or a combination thereof; optionally, store the received electromagnetic signal; optionally, process the received electromagnetic signal to determine a property; and optionally, output the received signal, the property, or a combination thereof. The electromagnetic signal captured by the amplifier can, for example, comprise the ionization current, amplified voltage, or a combination thereof.

In certain examples, the device 100 comprises a computing device 1040 comprising a processor 1042 and a memory 1044 operably coupled to the processor 1042, the memory 1044 having further computer-executable instructions stored thereon that, when executed by the processor 1042, cause the processor 1042 to: receive an electromagnetic signal captured by the detection electrode; process the electromagnetic signal to determine a property; and send an electromagnetic signal to the power source based on the property, to thereby heat or cool the temperature control layer to a desired temperature at a desired rate based on the property, which induces a desired potential in the pyroelectric layer via the pyroelectric effect.

The analysis of signals captured by the detection electrode can be carried out in whole or in part on one or more computing device. For example, the devices may comprise one or more additional computing device.

Also disclosed herein are methods of making the devices disclosed herein.

The methods can comprise, for example, disposing the grounded electrode 300 on the temperature control layer 200. In some examples, the methods can further comprise making the grounded electrode. In some examples, the grounded electrode can be deposited on the temperature control layer using techniques, such as, for example, electroplating, lithographic deposition, electron beam deposition, thermal deposition, spin coating, drop-casting, zone casting, dip coating, blade coating, spraying, vacuum filtration, chemical vapor deposition (CVD), atomic layer deposition (ALD), physical vapor deposition (PVD), sputtering, pulsed layer deposition, molecular beam epitaxy, evaporation, or combinations thereof.

The methods can, for example, further comprise disposing the pyroelectric layer 400 on the grounded electrode 300. In some examples, the methods can further comprise making the pyroelectric layer 400. The pyroelectric layer 400 can, for example, be made via chemical vapor deposition (CVD), atomic layer deposition (ALD), physical vapor deposition (PVD), sputtering, pulsed layer deposition, molecular beam epitaxy, evaporation, or combinations thereof.

In some examples, the top surface 402 of the pyroelectric layer 400 is textured, and the methods can further comprise texturing the top surface 402 of the pyroelectric layer 400. In some examples, the methods can further comprise making the pyroelectric layer 400 having a textured top surface 402, for example via chemical vapor deposition (CVD), atomic layer deposition (ALD), physical vapor deposition (PVD), sputtering, pulsed layer deposition, molecular beam epitaxy, evaporation, lithographic patterning, etching, micromachining, deep reactive ion etching, direct laser ablation, or a combination thereof. In some examples, the methods can further comprise making the pyroelectric layer 400 having a textured top surface 402, for example via use of an abrasive (e.g., sandpaper).

In some examples, the top surface 402 of the pyroelectric layer 400 can be textured, wherein the pyroelectric layer 400 can comprise a set of protrusions 420 extending from the top surface 402. The set of protrusions 420 can be integrally formed with the pyroelectric layer 400. The top surface 402 of the pyroelectric layer 400 can be textured using standard techniques known in the art, such as lithographic patterning, etching, micromachining, deep reactive ion etching, direct laser ablation, and the like.

In some examples, the pyroelectric layer 400 can comprise a set of particles 430 disposed on the top surface 402 and the methods can further comprise depositing the set of particles 430 on the top surface of the pyroelectric layer 400. Depositing the set of particles 430 can, for example, comprise printing, lithographic deposition, electron beam deposition, thermal deposition, spin coating, drop-casting, zone casting, dip coating, blade coating, spraying, vacuum filtration, or combinations thereof. In some examples, the methods can further comprise making the set of particles 430.

The methods can, for examples, further comprise disposing the detection electrode 500 opposite and spaced apart from the pyroelectric 400 layer by a distance 610, thereby defining the ionization zone 600 between the detection electrode 500 and the pyroelectric layer 400.

In some examples, the methods can further comprise patterning the set of cavities 510, the set of protrusions 520, the set of particles 530, or a combination thereof in/on the patterned detection electrode 500. The set of cavities 510, the set of protrusions 520, the set of particles 530, or a combination thereof can be patterned in/on the patterned detection electrode 500 using standard techniques known in the art, such as lithographic patterning, etching, micromachining, deep reactive ion etching, direct laser ablation, and the like.

In some examples, the patterned detection electrode 500 comprises a set of particles 530 disposed on the bottom surface 504 of the patterned detection electrode 500 and the methods can further comprise making the patterned detection electrode 500.

For example, the methods can comprise depositing the set of particles 530 on the bottom surface 504 of the patterned detection electrode 500. Depositing the set of particles 530 can, for example, comprise printing, lithographic deposition, electron beam deposition, thermal deposition, spin coating, drop-casting, zone casting, dip coating, blade coating, spraying, vacuum filtration, or combinations thereof. In some examples, the methods can further comprise making the set of particles 530.

In some examples, the set of particles 530 can comprise a metal and the methods can comprise making the patterned detection electrode 500 by thermally annealing a film of the metal deposited on the bottom surface 504 of the detection electrode 500, thereby forming the set of particles 530. In some examples, the methods can further comprise depositing the film of the metal. The film of metal can be deposited, for example, by thin film processing techniques, such as sputtering, pulsed layer deposition, molecular beam epitaxy, evaporation, atomic layer deposition, or combinations thereof.

In some examples, the methods can further comprise making the patterned detection electrode 500, for example via use of an abrasive (e.g., sandpaper).

Figures 35, 36:
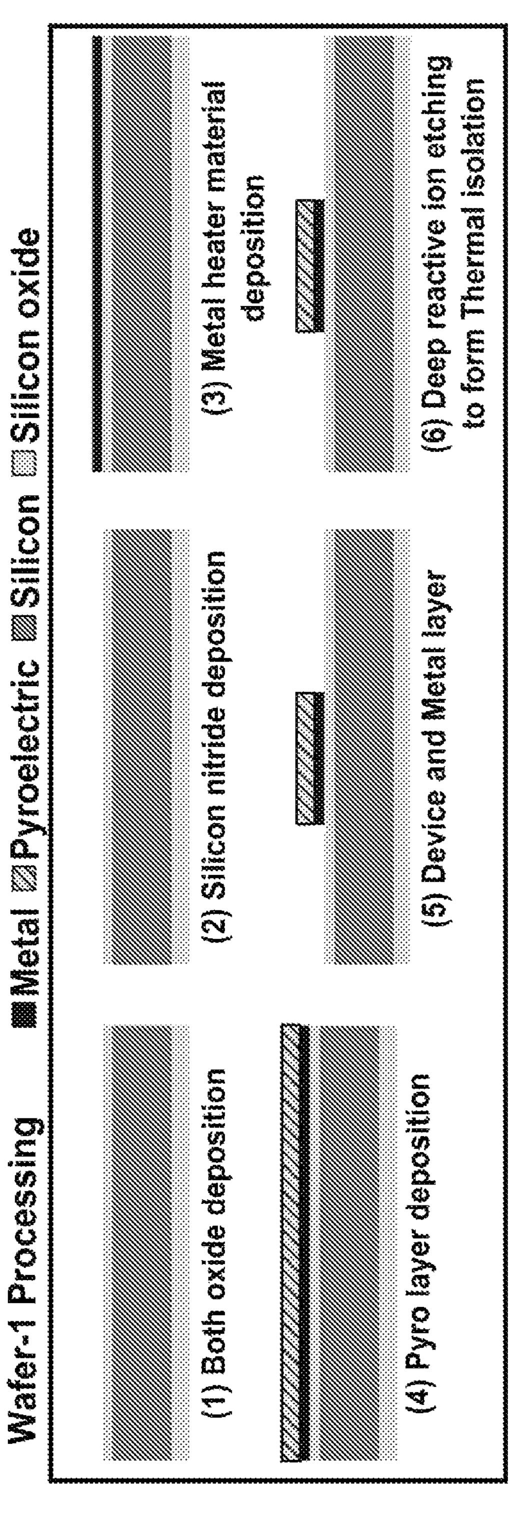
FIG. 35 is a schematic illustration of an example method of making a first portion of a device according to one implementation.
FIG. 36 is a schematic illustration of an example method of making a second portion of a device according to one implementation.
Figure 37:
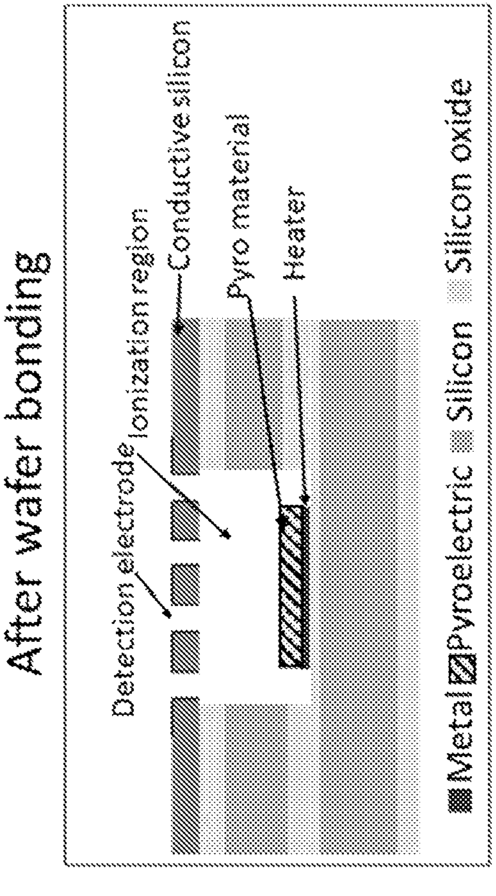
FIG. 37 is a schematic illustration of an example method for making a device according to one implementation.
Figure 37:
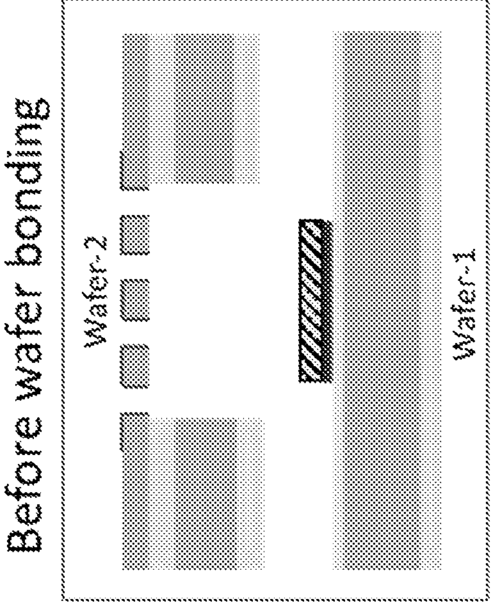

In some examples, the methods of making the devices can comprise fabricating a first portion of the device, as shown in FIG. 35, fabricating a second portion of the device, as shown in FIG. 36, and disposing the first portion of the device relative to the second portion of the device, as shown in FIG. 37, thereby forming the device. For example, fabricating the first portion of the device can comprise making and disposing the grounded electrode on the temperature control layer and subsequently making and disposing the pyroelectric layer on the grounded electrode. In some examples, fabricating the second portion of the device can comprise making the detection electrode. In some examples, disposing the first portion of the device relative to the second portion of the device can comprise disposing the detection electrode opposite and spaced apart from the pyroelectric layer by a distance, and optionally bonding the first portion of the device to the second portion of the device.

Also disclosed herein are gas detection methods for distinguishing a first gas component and a second gas component, the method comprising: introducing a gas into an ionization zone of a gas detector device, the gas detector device comprising: a temperature control layer; a grounded electrode disposed on the temperature control layer, wherein the grounded electrode is thermally conductive and is in thermal contact with the temperature control layer; a pyroelectric layer comprising a pyroelectric material, wherein the pyroelectric layer is disposed on the grounded electrode such that the grounded electrode is disposed between the temperature control layer and the pyroelectric layer, and wherein the pyroelectric layer is in thermal contact and electrical contact with the grounded electrode; and a detection electrode opposite and spaced apart from the pyroelectric layer by a distance, such that the detection electrode and the pyroelectric layer define an ionization zone between the detection electrode and the pyroelectric layer. The gas comprises a first gas component and a second gas component. In some examples, the detection electrode can comprise a patterned detection electrode comprising a set of cavities, a set of protrusions, or a combination thereof.

Also disclosed herein are gas detection method for distinguishing a first gas component and a second gas component, the method comprising: introducing a gas into the ionization zone of any of the gas detection devices 100 disclosed herein, wherein the gas comprises the first gas component and the second gas component.

The gas detection methods for distinguishing a first gas component and a second gas component comprise: introducing a gas into the ionization zone of the gas detection device while heating or cooling the temperature control layer to a first temperature at a first rate, which induces a first potential in the pyroelectric layer via the pyroelectric effect; wherein the gas comprises the first gas component and the second gas component; wherein the first gas component has a first ionization potential and the second gas component has a second ionization potential; wherein the second ionization potential is greater than the first ionization potential; wherein the first potential is greater than or equal to the first ionization potential and less than the second ionization potential; thereby ionizing the first gas component to produce a first ion; and electrically detecting the first ion via the detection electrode; subsequently, heating or cooling the temperature control layer to a second temperature at a second rate, which induces a second potential in the pyroelectric layer via the pyroelectric effect; wherein the second potential is greater than or equal to the second ionization potential; thereby ionizing the first gas component to produce the first ion and ionizing the second gas component to produce a second ion; and electrically detecting the first ion and the second ion via the detection electrode.

In some examples, the gas can further comprise a third gas component; wherein the third gas component has a third ionization potential; wherein the third ionization potential is greater than the second ionization potential; and the methods can further comprise distinguishing the third gas component. For example, the methods can further comprise subsequently heating or cooling the temperature control layer to a third temperature at a third rate, which induces a third potential in the pyroelectric layer via the pyroelectric effect; wherein the third potential is greater than or equal to the third ionization potential; thereby ionizing the first gas component to produce the first ion, ionizing the second gas component to produce the second ion, and ionizing the third gas component to produce a third ion; and electrically detecting the first ion, the second ion, and the third ion via the detection electrode.

For example, the methods can comprise introducing a gas into the ionization zone of the gas detection device while heating or cooling the temperature control layer to a first temperature at a first rate, which induces a first potential in the pyroelectric layer via the pyroelectric effect; wherein the gas comprises a first gas component, a second gas component, and a third gas component; wherein the first gas component has a first ionization potential, the second gas component has a second ionization potential, and the third gas component has a third ionization potential; wherein the second ionization potential is greater than the first ionization potential; wherein the third ionization potential is greater than the second ionization potential; wherein the first potential is greater than or equal to the first ionization potential and less than the second ionization potential; thereby ionizing the first gas component to produce a first ion; and electrically detecting the first ion via the detection electrode; subsequently, heating or cooling the temperature control layer to a second temperature at a second rate, which induces a second potential in the pyroelectric layer via the pyroelectric effect; wherein the second potential is greater than or equal to the second ionization potential and less than the third ionization potential; thereby ionizing the first gas component to produce the first ion and ionizing the second gas component to produce a second ion; electrically detecting the first ion and the second ion via the detection electrode; subsequently, heating or cooling the temperature control layer to a third temperature at a third rate, which induces a third potential in the pyroelectric layer via the pyroelectric effect; wherein the third potential is greater than or equal to the third ionization potential; thereby ionizing the first gas component to produce the first ion, ionizing the second gas component to produce the second ion, and ionizing the third gas component to produce a third ion; and electrically detecting the first ion, the second ion, and the third ion via the detection electrode.

In some examples, introducing the gas into the ionization zone of the gas detection device can be passive or active. In some examples, introducing the gas into the ionization zone of the gas detection device can comprise flowing the gas through the ionization zone of the gas detection device. Flowing the gas through the ionization zone can, for example, be controlled using a fluid flow control device, such as a fan, a blower, etc.

The first gas component, the second gas component, the third gas component (when present), or a combination thereof can independently comprise, for example, a volatile organic compound, a semi-volatile organic compound, an inorganic gas, or a combination thereof.

In some examples, the first gas component, the second gas component, and the third gas component (when present) can be selected from the group consisting of styrene, toluene, benzene, acetone, isopropyl alcohol, ammonia, formaldehyde, acetylene, nitric acid, ethanol, oxygen, water vapor, methane, nitrous oxide, carbon dioxide, carbon monoxide, hydrogen, nitrogen, and argon.

In some examples, the first gas component, the second gas component, the third gas component (when present), or a combination thereof can comprise a biomarker (i.e., a molecular indicator associated with a particular pathological or physiological state).

For example, the systems, devices, and methods described herein can be used in clinical and healthcare settings to detect and/or quantify biomarkers or metabolites to identify risk for, diagnosis of, or progression of a pathological or physiological process in a subject. Examples of biomarkers include proteins, peptides, polypeptides, hormones, prohormones, lipids, glycoproteins, carbohydrates, DNA, RNA, and combinations thereof.

In some examples, the gas can comprise a gaseous or aerosolized bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningeal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples. In some examples, the bodily fluid comprises exhaled breath.

In some examples, the first gas component, the second gas component, the third gas component (when present), or a combination thereof can comprise a pathogen (e.g., bacteria, virus, fungi, parasite, or protozoa), a biomarker indicative of a pathogen, or a combination thereof. In some examples, the first gas component, the second gas component, the third gas component (when present), or a combination thereof can comprise a toxin, a contaminant, a warfare agent (e.g., an explosive residue, a chemical warfare agent, a biological warfare agent, etc.), or a combination thereof. Examples of chemical warfare agents include, but are not limited to, nerve agents (e.g., sarin, soman, cyclosarin, tabun, Ethyl ({2-[bis(propan-2-yl)amino]ethyl}sulfanyl)(methyl)phosphinate (VX), O-pinacolylmethylphosphonofluoridate), vesicating or blistering agents (e.g., mustards, lewisite), respiratory agents (e.g., chlorine, phosgene, diphosgene), cyanides, antimiscarinic agents (e.g., anticholinergic compounds), opioid agents, lachrymatory agents (e.g., a-cholorotoluene, benzyl bromide, boromoacetone (BA), boromobenzylcyanide (CA), capsaicin (OC), chloracetophenone (MACE), chlormethyl choloroformate, dibenoxazepine (CR), ethyl iodoacetate, ortho-chlorobenzlidene malonitrile (CS), trichloromethyl chloroformate, xylyl bromide), and vomiting agents (e.g., adamsite (DM), diphenylchloroarsine (DA), diphenylcanoarsine (DC)). Biological warfare agents include, but are not limited to bacteria (e.g., *Bacillus anthracis, Bacillus abortus, Brucella suis, Vibrio cholerae, Corynebacterium diptheriae, Shigella dysenteriae, Escherichia coli, Burkholderia mallei, Listeria monocytogenes, Burkholderia pseudomallei, Yersinia pestis, Francisella tularensis, Chlamydophila psittaci, Coxiella burnetii, Rickettsia, Rickettsia prowazekii, Rickettsia typhi*), viruses (e.g., Eastern equine encephalitis virus, Venezuelan equine encephalitis virus, Western equine encephalitis virus, Japanese encephalitis virus, Rift Valley fever virus, Variola virus, Yellow Fever virus, Ebola virus, Marburg virus), protozoa, parasites, fungi (*Coccidioides immitis*), pathogens, toxins, and biotoxins (Abrin, Botulinum toxin, Ricin, Saxitoxin, Staphylococcal enterotoxin B, tetrodotoxin, trichothecene mycotoxins).

The first ionization potential can, for example, be 1 electronvolts (eV) or more (e.g., 2 eV or more, 3 eV or more, 4 eV or more, 5 eV or more, 6 eV or more, 7 eV or more, 8 eV or more, 9 eV or more, 10 eV or more, 11 eV or more, 12 eV or more, 13 eV or more, 14 eV or more, 15 eV or more, 16 eV or more, 17 eV or more, 18 eV or more, 19 eV or more, 20 eV or more, 21 eV or more, 22 eV or more, 23 eV or more, 24 eV or more, 25 eV or more, 26 eV or more, 27 eV or more, 28 eV or more, or 29 eV or more). In some examples, the first ionization potential can be 30 eV or less (e.g., 29 eV or less, 28 eV or less, 27 eV or less, 26 eV or less, 25 eV or less, 24 eV or less, 23 eV or less, 22 eV or less, 21 eV or less, 20 eV or less, 19 eV or less, 18 eV or less, 17 eV or less, 16 eV or less, 15 eV or less, 14 eV or less, 13 eV or less, 12 eV or less, 11 eV or less, 10 eV or less, 9 eV or less, 8 eV or less, 7 eV or less, 6 eV or less, 5 eV or less, 4 eV or less, 3 eV or less, or 2 eV or less). The first ionization potential can range from any of the minimum values described above to any of the maximum values described above. For example, the first ionization potential can be from 1 eV to 30 eV (e.g., from 1 eV to 15 eV, from 15 eV to 30 eV, from 1 eV to 10 eV, from 10 eV to 20 eV, from 20 eV to 30 eV, from 1 eV to 28 eV, from 3 eV to 30 eV, from 3 eV to 28 eV, or from 7 eV to 26 eV).

The second ionization potential can, for example, be 1 electronvolts (eV) or more (e.g., 2 eV or more, 3 eV or more, 4 eV or more, 5 eV or more, 6 eV or more, 7 eV or more, 8 eV or more, 9 eV or more, 10 eV or more, 11 eV or more, 12 eV or more, 13 eV or more, 14 eV or more, 15 eV or more, 16 eV or more, 17 eV or more, 18 eV or more, 19 eV or more, 20 eV or more, 21 eV or more, 22 eV or more, 23 eV or more, 24 eV or more, 25 eV or more, 26 eV or more, 27 eV or more, 28 eV or more, or 29 eV or more). In some examples, the second ionization potential can be 30 eV or less (e.g., 29 eV or less, 28 eV or less, 27 eV or less, 26 eV or less, 25 eV or less, 24 eV or less, 23 eV or less, 22 eV or less, 21 eV or less, 20 eV or less, 19 eV or less, 18 eV or less, 17 eV or less, 16 eV or less, 15 eV or less, 14 eV or less, 13 eV or less, 12 eV or less, 11 eV or less, 10 eV or less, 9 eV or less, 8 eV or less, 7 eV or less, 6 eV or less, 5 eV or less, 4 eV or less, 3 eV or less, or 2 eV or less). The second ionization potential can range from any of the minimum values described above to any of the maximum values described above. For example, the second ionization potential can be from 1 eV to 30 eV (e.g., from 1 eV to 15 eV, from 15 eV to 30 eV, from 1 eV to 10 eV, from 10 eV to 20 eV, from 20 eV to 30 eV, from 1 eV to 28 eV, from 3 eV to 30 eV, from 3 eV to 28 eV, or from 7 eV to 26 eV).

The third ionization potential (when the third gas component is present) can, for example, be 1 electronvolts (eV) or more (e.g., 2 eV or more, 3 eV or more, 4 eV or more, 5 eV or more, 6 eV or more, 7 eV or more, 8 eV or more, 9 eV or more, 10 eV or more, 11 eV or more, 12 eV or more, 13 eV or more, 14 eV or more, 15 eV or more, 16 eV or more, 17 eV or more, 18 eV or more, 19 eV or more, 20 eV or more, 21 eV or more, 22 eV or more, 23 eV or more, 24 eV or more, 25 eV or more, 26 eV or more, 27 eV or more, 28 eV or more, or 29 eV or more). In some examples, the third ionization potential can be 30 eV or less (e.g., 29 eV or less, 28 eV or less, 27 eV or less, 26 eV or less, 25 eV or less, 24 eV or less, 23 eV or less, 22 eV or less, 21 eV or less, 20 eV or less, 19 eV or less, 18 eV or less, 17 eV or less, 16 eV or less, 15 eV or less, 14 eV or less, 13 eV or less, 12 eV or less, 11 eV or less, 10 eV or less, 9 eV or less, 8 eV or less, 7 eV or less, 6 eV or less, 5 eV or less, 4 eV or less, 3 eV or less, or 2 eV or less). The third ionization potential can range from any of the minimum values described above to any of the maximum values described above. For example, the third ionization potential can be from 1 eV to 30 eV (e.g., from 1 eV to 15 eV, from 15 eV to 30 eV, from 1 eV to 10 eV, from 10 eV to 20 eV, from 20 eV to 30 eV, from 1 eV to 28 eV, from 3 eV to 30 eV, from 3 eV to 28 eV, or from 7 eV to 26 eV).

The first temperature can, for example, be −200° C. or more (e.g., −175° C. or more, −150° C. or more, −125° C. or more, −100° C. or more, −75° C. or more, −50° C. or more, −25° C. or more, 0° C. or more, 25° C. or more, 50° C. or more, 75° C. or more, 100° C. or more, 125° C. or more, 150° C. or more, 175° C. or more, 200° C. or more, 225° C. or more, 250° C. or more, 275° C. or more, 300° C. or more, 325° C. or more, 350° C. or more, 375° C. or more, 400° C. or more, 425° C. or more, 450° C. or more, or 475° C. or more). In some examples, the first temperature can be 500° C. or less (e.g., 475° C. or less, 450° C. or less, 425° C. or less, 400° C. or less, 375° C. or less, 350° C. or less, 325° C. or less, 300° C. or less, 275° C. or less, 250° C. or less, 225° C. or less, 200° C. or less, 175° C. or less, 150° C. or less, 125° C. or less, 100° C. or less, 75° C. or less, 50° C. or less, 25° C. or less, 0° C. or less, −25° C. or less, −50° C. or less, −75° C. or less, −100° C. or less, −125° C. or less, −150° C. or less, or −175° C. or less). The first temperature can range from any of the minimum values described above to any of the maximum values described above. For example, the first temperature can be from −200° C. to 500° C. (e.g., from −200° C. to 150° C., from 150° C. to 500° C., from −200° C. to 0° C., from 0° C. to 250° C., from 250° C. to 500° C., from −150° C. to 500° C., from −200° C. to 450° C., from −150° C. to 450° C., from 0° C. to 500° C., or from 30° C. to 500° C.).

The second temperature can, for example, be −200° C. or more (e.g., −175° C. or more, −150° C. or more, −125° C. or more, −100° C. or more, −75° C. or more, −50° C. or more, −25° C. or more, 0° C. or more, 25° C. or more, 50° C. or more, 75° C. or more, 100° C. or more, 125° C. or more, 150° C. or more, 175° C. or more, 200° C. or more, 225° C. or more, 250° C. or more, 275° C. or more, 300° C. or more, 325° C. or more, 350° C. or more, 375° C. or more, 400° C. or more, 425° C. or more, 450° C. or more, or 475° C. or more). In some examples, the second temperature can be 500° C. or less (e.g., 475° C. or less, 450° C. or less, 425° C. or less, 400° C. or less, 375° C. or less, 350° C. or less, 325° C. or less, 300° C. or less, 275° C. or less, 250° C. or less, 225° C. or less, 200° C. or less, 175° C. or less, 150°

C. or less, 125° C. or less, 100° C. or less, 75° C. or less, 50° C. or less, 25° C. or less, 0° C. or less, −25° C. or less, −50° C. or less, −75° C. or less, −100° C. or less, −125° C. or less, −150° C. or less, or −175° C. or less). The second temperature can range from any of the minimum values described above to any of the maximum values described above. For example, the second temperature can be from −200° C. to 500° C. (e.g., from −200° C. to 150° C., from 150° C. to 500° C., from −200° C. to 0° C., from 0° C. to 250° C., from 250° C. to 500° C., from −150° C. to 500° C., from −200° C. to 450° C., from −150° C. to 450° C., from 0° C. to 500° C., or from 30° C. to 500° C.).

The third temperature (when the third gas component is present) can, for example, be −200° C. or more (e.g., −175° C. or more, −150° C. or more, −125° C. or more, −100° C. or more, −75° C. or more, −50° C. or more, −25° C. or more, 0° C. or more, 25° C. or more, 50° C. or more, 75° C. or more, 100° C. or more, 125° C. or more, 150° C. or more, 175° C. or more, 200° C. or more, 225° C. or more, 250° C. or more, 275° C. or more, 300° C. or more, 325° C. or more, 350° C. or more, 375° C. or more, 400° C. or more, 425° C. or more, 450° C. or more, or 475° C. or more). In some examples, the third temperature can be 500° C. or less (e.g., 475° C. or less, 450° C. or less, 425° C. or less, 400° C. or less, 375° C. or less, 350° C. or less, 325° C. or less, 300° C. or less, 275° C. or less, 250° C. or less, 225° C. or less, 200° C. or less, 175° C. or less, 150° C. or less, 125° C. or less, 100° C. or less, 75° C. or less, 50° C. or less, 25° C. or less, 0° C. or less, −25° C. or less, −50° C. or less, −75° C. or less, −100° C. or less, −125° C. or less, −150° C. or less, or −175° C. or less). The third temperature can range from any of the minimum values described above to any of the maximum values described above. For example, the third temperature can be from −200° C. to 500° C. (e.g., from −200° C. to 150° C., from 150° C. to 500° C., from −200° C. to 0° C., from 0° C. to 250° C., from 250° C. to 500° C., from −150° C. to 500° C., from −200° C. to 450° C., from −150° C. to 450° C., from 0° C. to 500° C., or from 30° C. to 500° C.).

The first rate at which the pyroelectric layer is heated or cooled can, for example, be 0.01° C./second or more (e.g., 0.05° C./second or more, 0.1° C./second or more, 0.5° C./second or more, 1° C./second or more, 2° C./second or more, 3° C./second or more, 4° C./second or more, 5° C./second or more, 10° C./second or more, 15° C./second or more, 20° C./second or more, 25° C./second or more, 30° C./second or more, 35° C./second or more, 40° C./second or more, 45° C./second or more, 50° C./second or more, 60° C./second or more, 70° C./second or more, 80° C./second or more, or 90° C./second or more). In some examples, the first rate at which the pyroelectric layer is heated or cooled can be 100° C./second or less (e.g., 90° C./second or less, 80° C./second or less, 70° C./second or less, 60° C./second or less, 50° C./second or less, 45° C./second or less, 40° C./second or less, 35° C./second or less, 30° C./second or less, 25° C./second or less, 20° C./second or less, 15° C./second or less, 10° C./second or less, 5° C./second or less, 4° C./second or less, 3° C./second or less, 2° C./second or less, 1° C./second or less, 0.5° C./second or less, 0.1° C./second or less, or 0.05° C./second or less). The first rate at which the pyroelectric layer is heated or cooled can range from any of the minimum values described above to any of the maximum values described above. For example, the first rate at which the pyroelectric layer is heated or cooled can be from 0.01° C./second to 100° C./second (e.g., from 0.01° C./second to 1° C./second, from 1° C./second to 100° C./second, from 0.01° C./second to 0.1° C./second, from 0.1° C./second to 1° C./second, from 1° C./second to 10° C./second, from 10° C./second to 100° C./second, from 0.1° C./second to 100° C./second, from 0.01° C./second to 90° C./second, from 0.1° C./second to 90° C./second, or from 0.1° C./second to 50° C./second).

The second rate at which the pyroelectric layer is heated or cooled can, for example, be 0.01° C./second or more (e.g., 0.05° C./second or more, 0.1° C./second or more, 0.5° C./second or more, 1° C./second or more, 2° C./second or more, 3° C./second or more, 4° C./second or more, 5° C./second or more, 10° C./second or more, 15° C./second or more, 20° C./second or more, 25° C./second or more, 30° C./second or more, 35° C./second or more, 40° C./second or more, 45° C./second or more, 50° C./second or more, 60° C./second or more, 70° C./second or more, 80° C./second or more, or 90° C./second or more). In some examples, the second rate at which the pyroelectric layer is heated or cooled can be 100° C./second or less (e.g., 90° C./second or less, 80° C./second or less, 70° C./second or less, 60° C./second or less, 50° C./second or less, 45° C./second or less, 40° C./second or less, 35° C./second or less, 30° C./second or less, 25° C./second or less, 20° C./second or less, 15° C./second or less, 10° C./second or less, 5° C./second or less, 4° C./second or less, 3° C./second or less, 2° C./second or less, 1° C./second or less, 0.5° C./second or less, 0.1° C./second or less, or 0.05° C./second or less). The second rate at which the pyroelectric layer is heated or cooled can range from any of the minimum values described above to any of the maximum values described above. For example, the second rate at which the pyroelectric layer is heated or cooled can be from 0.01° C./second to 100° C./second (e.g., from 0.01° C./second to 1° C./second, from 1° C./second to 100° C./second, from 0.01° C./second to 0.1° C./second, from 0.1° C./second to 1° C./second, from 1° C./second to 10° C./second, from 10° C./second to 100° C./second, from 0.1° C./second to 100° C./second, from 0.01° C./second to 90° C./second, from 0.1° C./second to 90° C./second, or from 0.1° C./second to 50° C./second).

The third rate at which the pyroelectric layer is heated or cooled (when the third gas component is present) can, for example, be 0.01° C./second or more (e.g., 0.05° C./second or more, 0.1° C./second or more, 0.5° C./second or more, 1° C./second or more, 2° C./second or more, 3° C./second or more, 4° C./second or more, 5° C./second or more, 10° C./second or more, 15° C./second or more, 20° C./second or more, 25° C./second or more, 30° C./second or more, 35° C./second or more, 40° C./second or more, 45° C./second or more, 50° C./second or more, 60° C./second or more, 70° C./second or more, 80° C./second or more, or 90° C./second or more). In some examples, the third rate at which the pyroelectric layer is heated or cooled can be 100° C./second or less (e.g., 90° C./second or less, 80° C./second or less, 70° C./second or less, 60° C./second or less, 50° C./second or less, 45° C./second or less, 40° C./second or less, 35° C./second or less, 30° C./second or less, 25° C./second or less, 20° C./second or less, 15° C./second or less, 10° C./second or less, 5° C./second or less, 4° C./second or less, 3° C./second or less, 2° C./second or less, 1° C./second or less, 0.5° C./second or less, 0.1° C./second or less, or 0.05° C./second or less). The third rate at which the pyroelectric layer is heated or cooled can range from any of the minimum values described above to any of the maximum values described above. For example, the third rate at which the pyroelectric layer is heated or cooled can be from 0.01° C./second to 100° C./second (e.g., from 0.01° C./second to 1° C./second, from 1° C./second to 100° C./second, from 0.01° C./second to 0.1° C./second, from 0.1° C./second to 1°

C./second, from 1° C./second to 10° C./second, from 10° C./second to 100° C./second, from 0.1° C./second to 100° C./second, from 0.01° C./second to 90° C./second, from 0.1° C./second to 90° C./second, or from 0.1° C./second to 50° C./second).

In the methods can further comprise processing the electromagnetic signals (e.g., electrical signals) from the detection electrode to determine a property. The electromagnetic signal captured by the detection electrode can, for example, comprise an electrical signal, such as a current or voltage signal in direct current (DC) or alternating current (AC) with variable frequencies. The electromagnetic signal captured by the detection electrode can, for example, comprise the ionization current, amplified voltage, or a combination thereof. The property can, for example, comprise the presence of the first gas component, the second gas component, the third gas component, or a combination thereof; the identity of the first gas component, the second gas component, the third gas component (when present), or a combination thereof; the relative amount of the first gas component, the second gas component, the third gas component (when present), or a combination thereof in the gas; or a combination thereof. In some examples, processing the electrical signal from the detection electrode comprises integrating the electrical signal from the detection electrode and the property comprises the total number of ions detected by the detection electrode.

In some examples, the methods can comprise collecting an electromagnetic signal from the detection electrode for the duration of the time that the temperature control layer is being heated or cooled. The methods can, for example, further comprise integrating the collected electromagnetic signal over the duration of the heating or cooling time to determine a property, wherein the property comprises the total concentration of ions detected over the duration of the heating or cooling time.

Figure 38:
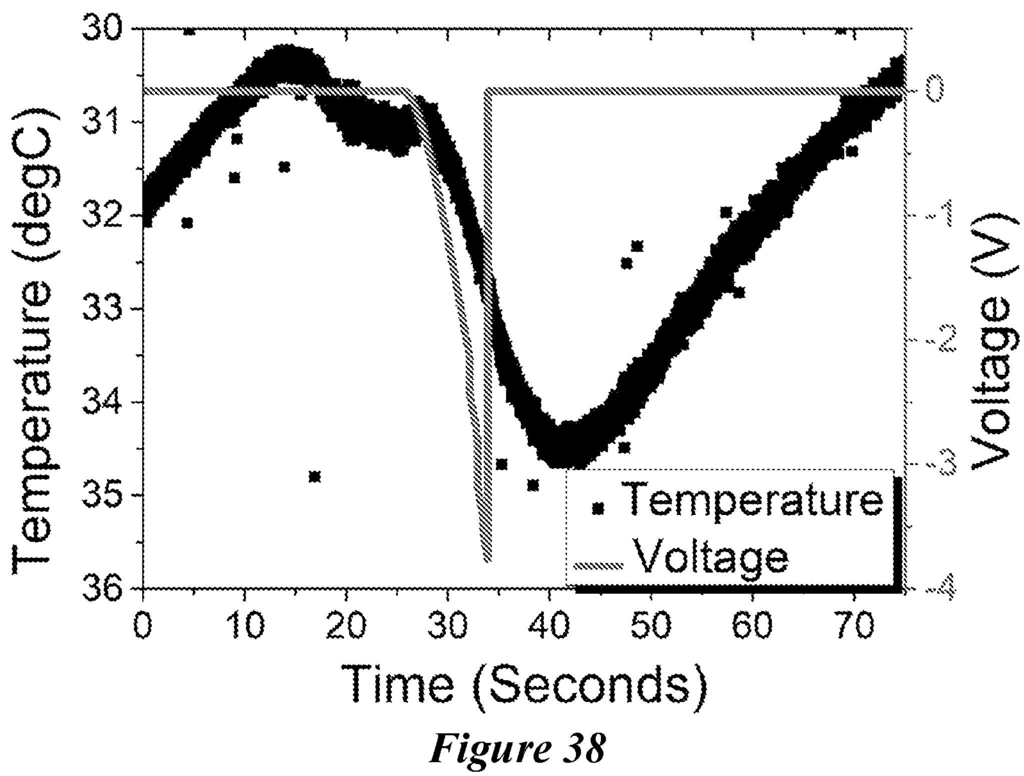
FIG. 38: Ionization events during the temperature ramp can be integrated and converted into one single peak current.

For example, ionization events during the temperature ramp can be integrated and converted into one single peak current. In some examples, a precision switched integrator transimpedance amplifier can be used to integrate the generated ionization events during the temperature ramp and convert it into one single peak current (FIG. 38). This can simplify data analysis and gas differentiation. For this approach, an increase in the peak voltage can correspond to an increase in thermal rate. For different gas mixtures, the change in voltage behavior can be calibrated.

In some examples, processing the electromagnetic signals (e.g., electrical signals) from the detection electrode can be carried out in whole or in part on one or more computing devices. For example, a computing device comprising a processor and a memory operably coupled to the processor, the memory having further computer-executable instructions stored thereon that, when executed by the processor, cause the processor to: receive an electromagnetic signal captured by the detection electrode; process the electromagnetic signal to determine a property; and output the property. For example, the computing device comprising a processor and a memory operably coupled to the processor, the memory having further computer-executable instructions stored thereon that, when executed by the processor, cause the processor to: receive an electromagnetic signal captured by the detection electrode; process the electromagnetic signal to determine a property of the first ion, the second ion, or a combination thereof; and output the property.

In some examples, the methods can comprise sending a first electromagnetic signal to a power source coupled to the temperature control layer, to thereby heat or cool the temperature control layer to the first temperature at the first rate, which induces the first potential in the pyroelectric layer via the pyroelectric effect. In some examples, the methods can comprise sending a second electromagnetic signal to the power source coupled to the temperature control layer, to thereby heat or cool the temperature control layer to the second temperature at the second rate, which induces the second potential in the pyroelectric layer via the pyroelectric effect. In some examples, the methods can further comprise sending a third electromagnetic signal to the power source coupled to the temperature control layer, to thereby heat or cool the temperature control layer to the third temperature at the third rate, which induces the third potential in the pyroelectric layer via the pyroelectric effect. In some examples, the first electromagnetic signal, the second electromagnetic signal, the third electromagnet signal, or a combination thereof can be sent from a computing device comprising a processor and a memory operably coupled to the processor, the memory having further computer-executable instructions stored thereon that, when executed by the processor, cause the processor to send the second electromagnetic signal, the third electromagnetic signal, or a combination thereof.

In some examples, the methods can further comprise sending and/or receiving electromagnetic signals (e.g., electrical signals) to/from the pressure sensor (when present), humidity sensor (when present), amplifier (when present), or a combination thereof. In some examples, the methods can further comprise processing electromagnetic signals (e.g., electrical signals) from the pressure sensor (when present), humidity sensor (when present), amplifier (when present), or a combination thereof. In some examples, processing the electromagnetic signals (e.g., electrical signals) from the pressure sensor (when present), humidity sensor (when present), amplifier (when present), or a combination thereof can be carried out in whole or in part on one or more computing devices. For example, a computing device comprising a processor and a memory operably coupled to the processor, the memory having further computer-executable instructions stored thereon that, when executed by the processor, cause the processor to: receive an electromagnetic signal (e.g., electrical signal) from the pressure sensor (when present), humidity sensor (when present), amplifier (when present), or a combination thereof; optionally, store the received electromagnetic signal; optionally, process the received electromagnetic signal to determine a property; and optionally, output the received signal, the property, or a combination thereof. The electromagnetic signal captured by the amplifier can, for example, comprise the ionization current, amplified voltage, or a combination thereof.

In some examples, the methods can comprise processing an electromagnetic signal captured by the detection electrode to determine a property; and subsequently sending an electromagnetic signal to the power source based on the property, to thereby heat or cool the temperature control layer to a desired temperature at a desired rate based on the property, which induces a desired potential in the pyroelectric layer via the pyroelectric effect.

Also described herein are methods of use of any of the devices described herein. For example, the gas detector devices can be used for air quality monitoring (e.g., indoor air, outdoor air), environmental monitoring, toxic gas detection, exhaled breath analysis, or a combination thereof. In some examples, the gas detector devices described herein can be incorporated into a consumer product, such as a mobile device (e.g. cell phone, wearable, etc.). In some examples, the gas detector devices can be used as distributed sensors for Internet of Things (IOT) and the Industrial Internet of Things (IIOT) applications. In some examples, the gas detector devices can be used for chemical process monitoring, monitoring of gases in pipes, monitoring inside reactors, monitoring inside fridge/oven/and other consumer appliances, monitoring inside a subject's body (e.g., wherein the gas detector device is encapsulated in a delivery device that can be inserted inside the body of a subject, for example by swallowing).

Also described herein are methods of use of any of the devices described herein to diagnose and/or monitor a disease in a subject by determining the property of the gas. The property can, for example, comprise the presence of the first gas component, the second gas component, the third gas component, or a combination thereof; the identity of the first gas component, the second gas component, the third gas component (when present), or a combination thereof; the relative amount of the first gas component, the second gas component, the third gas component (when present), or a combination thereof in the gas; or a combination thereof.

In some examples, the first gas component, the second gas component, the third gas component (when present), or a combination thereof can be, for example, a biomarker (i.e., a molecular indicator associated with a particular pathological or physiological state) present in a gaseous or aerosolized bodily fluid (e.g., the gas) that can be assayed to identify risk for, diagnosis of, or progression of a pathological or physiological process in a subject. Examples of diseases include, but are not limited to neurodegenerative diseases, infectious diseases (e.g., infection with a pathogen such as a virus, bacteria, fungi, protozoa, or parasite), rheumatologic diseases, genetic diseases, acute and chronic respiratory diseases, gastrointestinal diseases, liver diseases, dermatologic diseases, and combinations thereof. In some examples, the methods can further comprise selecting a course of therapy for the subject based on the property of the gas.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Ionization Potential Tunable Pyroelectric Ambient Pressure Multi-Gas Detection Platform

Abstract

Figure 51:
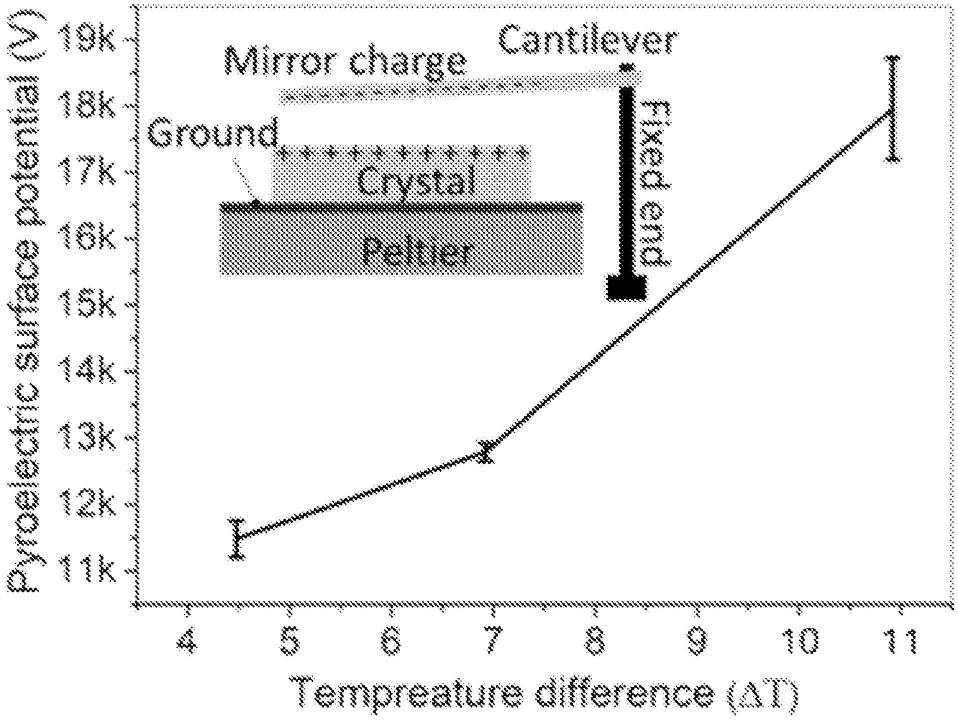
FIG. 51: Measured pyroelectric surface potential for different temperature differences. Inset shows the electrostatic cantilever approach used to measure the surface potential. Initial temperature used is 30° C.

An ionization potential tunable gas detection platform is described herein. Tuning the ionization potential allows for gradual ionization of different gases, therefore potentially enabling gas identification. The ionization potential tunable gas detection platform described herein opens up opportunities for developing miniature sensors for applications in air quality, environmental monitoring, toxic gas detection, and consumer-related products. The tunable ionization potential is produced using a lithium niobate pyroelectric crystal by controlling its heating temperature rate. The ionization potential generated from pyroelectrically emitted electrons can be tuned with the heating rate and gap between the detection electrode and pyroelectrically charged surface. A lithium niobate pyroelectric ionization source was established by integrating a Peltier-based heating system and a fabricated ionization detection electrode. Thermal distribution on the crystal surface was studied using Multiphysics COMSOL simulation and compared with experimentally measured values. Pyroelectrically generated surface potential was measured for different temperature rates using an electrostatic cantilever approach (FIG. 51). Ionization of vapors of acetone, isopropyl alcohol, ethanol, and ambient air was carried out at different temperature rates and at different electrode gaps to demonstrate the ionization potential tunability. The obtained results showed a clear distinction between the ionization of volatile organic compounds (VOCs) and ambient air.

Introduction

The World Health Organization (WHO) estimates that air pollution kills ~7 million people each year-equivalent to 13 deaths every minute-more than the combined total of war, murder, tuberculosis, HIV, AIDS, and malaria (World Health Organization, "WHO|Air pollution," 2019). Apart from physical health, a recent report shows air pollution can affect mental illness—a strong link was indicated between air pollution and bipolar disorder, depression, personality disorder, and schizophrenia (Khan et al. *PLOS Biol*., vol. 17, no. 8, 2019). The first step towards controlling air quality is measuring and understanding the chemical components present at multiple locations. Performance, size, and cost of gas sensors play a key role in enabling air quality and toxic gas monitoring. Currently available small and portable/distributed technologies include: (a) Portable gas chromatography-mass spectrometry (GC-MS) systems based on micromachined silicon, which offer good sensitivity and selectivity, but are expensive to fabricate and assemble. (b) Metal oxide semiconductor sensors (MOS) are compact and low-cost but suffer from sensitivity to humidity, non-linear response, and long-term drift. (c) Photoionization detectors (PID) produce instantaneous readings, operate continuously, and are commonly used as detectors for gas chromatography or as hand-held instruments. Photoionization detectors can measure low parts per billion (ppb), however photoionization detectors can only indicate the presence of a volatile organic compound without ability to identify the gas molecules (Pham et al. *Advanced Science*. 2020, 7(21), 2001294; Day et al. *ACS Omega,* 2020, 5(29), 18073-18079; Parmar et al. *Sensors Actuators, B Chem.,* 2011, 158 (1), 229-234; Syms et al. *Journal of Micromechanics and Microengineering,* 2016, 26(2), 023001; Park et al. *Sensors Actuators, B Chem.,* 2018, 273, 1556-1563). Attempts to make efficient, low-cost, miniature gas sensor for multi-gas detection are still evolving; microfabrication is key for applications in Internet of Things (IOT) and the Industrial Internet of Things (IIOT).

Pyroelectric materials are traditionally well known in the area of radiation detection. Changes in temperature causes electric charge generation on the surfaces of the pyroelectric crystal (Putley. *Semicond. Semimetals,* 1970, 5, 259-285). Electron emission from pyroelectrics has been studied and demonstrated (Rosenman et al. *J. Appl. Phys.,* 2000, 88(11), 6109). Generation of a self-focused electron beam from pyroelectric lithium niobate has been also demonstrated during the process of heating/cooling (Brownridge et al. *Appl. Phys. Lett.,* 2001, 79(20), 3364). Based on that, pyroelectric crystals have been used as an ionization sources for mass spectrometers (Neidholdt et al. *Anal. Chem.,* 2007, 79(10), 3945-3948; Neidholdt et al. *J. Am. Soc. Mass Spectrom.,* 2009, 20(11), 2093-2099; Vinayakumar et al. IEEE Sensors, 2016, pp. 1-3, doi: 10.1109/ICSENS.2016.7808451; Modi et al. *Nature,* 2003, 424, 171-174). Ionization potential sweeping/tuning has been previously demonstrated using conventional transistors and vertical carbon nanotubes (Modi et al. *Nature,* 2003, 424, 171-174; Ou et al. 2019 *IEEE 4th International Future Energy Electronics Conference* (*IFEEC*). IEEE, 2019, pp. 1-4, doi: 10.1109/IFEEC47410.2019.9014980). These ionization approaches normally require a variable high voltage power supply and complicated electronics with required safety measures and electrical isolation. Hence, the conventional approach is not practical for miniature distributed sensor applications with respect to power requirement, size, cost, and microfabrication capabilities.

Although the ionization of gas molecules from pyroelectric crystals has been demonstrated (Neidholdt et al. *Anal. Chem.,* 2007, 79(10), 3945-3948; Neidholdt et al. *J. Am. Soc. Mass Spectrom.,* 2009, 20(11), 2093-2099; Vinayakumar et al. IEEE Sensors, 2016, pp. 1-3, doi: 10.1109/ICSENS.2016.7808451), there have been no studies on the sweeping capability of the pyroelectric ionization potential. The results herein using a pyroelectric crystal with ionization potential tuning capability demonstrate a promising ability to ionize different gases, as well as the potential for development of a low-cost multi-gas detection platform that does not require high-voltage, high-temperature, vacuum pump, or chemical functionalization. Hence, there is huge potential for use of the devices described herein as distributed sensors for IOT and IIOT applications.

Working Principle

Figure 39:
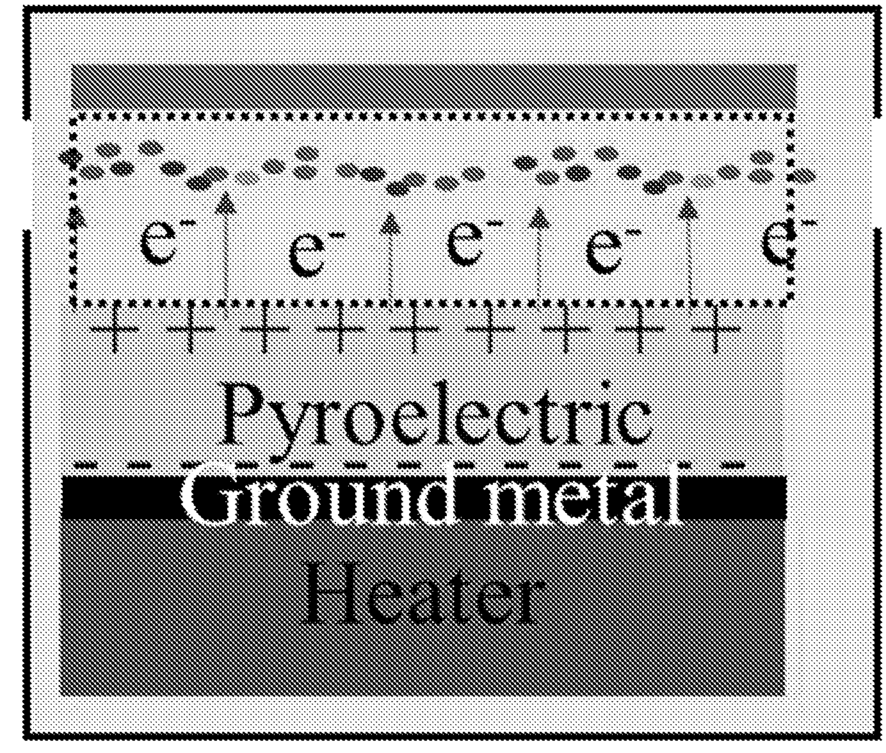
FIG. 39. Schematic showing the working methodology of the pyroelectric ionization-based gas sensor.
Figure 40:
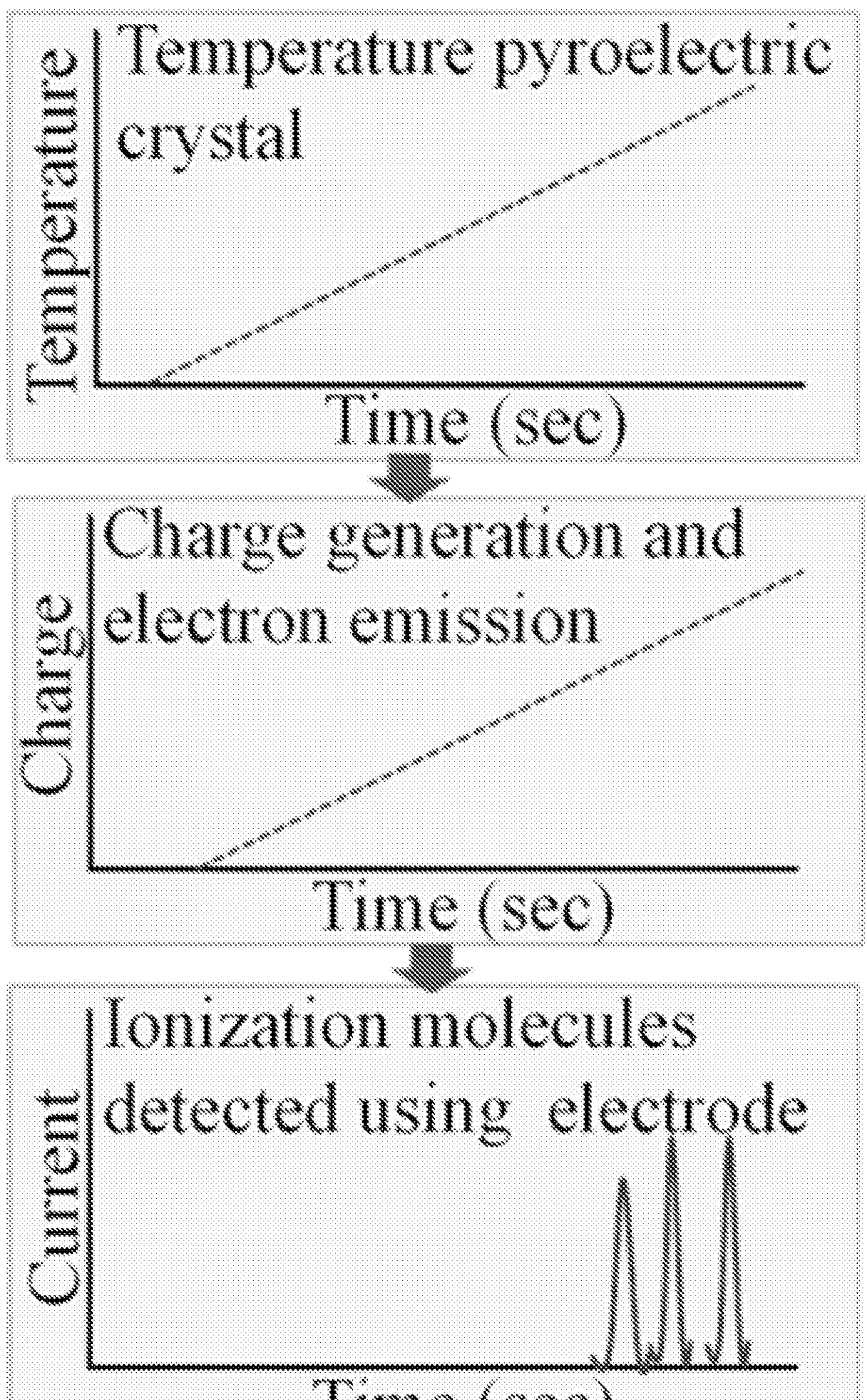
FIG. 40. Schematic showing that the increasing pyroelectric temperature (top panel) will result in charge generation on the polarized surface (middle panel) of the crystal and subsequent ionization of surrounding molecules (bottom panel).

During the process of pyroelectric crystal heating/cooling, the net dipole moment of the crystal changes, producing a change in the surface charge density on the polarized faces of the crystal. The resulting potential on the polarized surface causes electron emission (Rosenman et al. *J. Appl. Phys.,* 2000, 88(11), 6109; Brownridge et al. *Appl. Phys. Lett.,* 2001, 79(20), 3364). In the gas sensor platform discussed herein, gas flows across the polarized surface of the pyroelectric crystal where the gas molecules are ionized and then measured by an electrode (FIG. 39-FIG. 40).

Figures 41A, 41B:
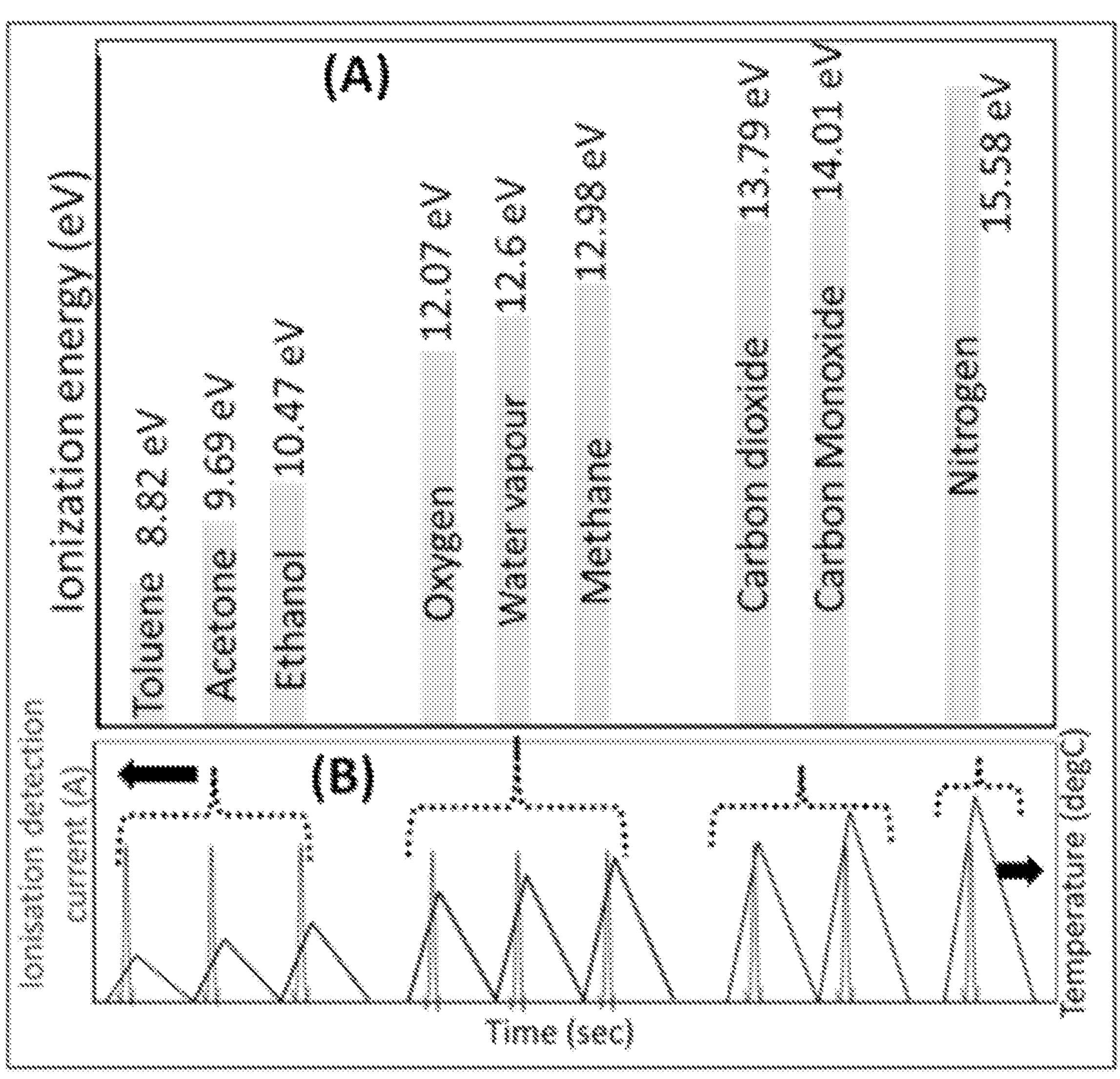
FIG. 41A-FIG. 41B.

The ionization potential tunable source and detector device described herein is based on the concept of ionization energy modulation. This relies on the fact that different gas molecules are ionized at different times as the ionization energy is modulated during a few seconds of the measurement. Photoionization energies of common gases are shown in FIG. 41A. For example, aromatic molecules have a lower energy of ionization compared to other volatile organic compounds and compared to inorganic gases (Modi et al. *Nature,* 2003, 424, 171-174). The pyroelectrically emitted electron energy (eV) depends on the rate of change of temperature, the thickness of the crystal, distance from the ionizing molecules, and the pyroelectric surface area (Equation-1):

$$V_p = \frac{\varphi t}{\varepsilon_{cr}} \frac{dT}{dt} \tag{1}$$

Where $V_p$ is the pyroelectric voltage, t is the thickness of the crystal (5 mm) in the polarized direction, φ is the pyroelectric coefficient (70 μC/m$^2$K), dT/dt is the temperature rate and Ecr is the dielectric constant of the material (30).

Further, the detection of ionized molecules is carried out sequentially and compared with the previously ionized molecules at different temperature rate to identify the unknown gaseous molecules (FIG. 41B).

Experimental

Two different experiments were conducted to understand the pyroelectric ionization and demonstrate detection of various compounds. Components used included: a z-cut pyroelectric lithium niobate (5 mm thick, 25 mm diameter), Peltier element to thermally cycle the pyroelectric crystal, an electrode to detect the ionized molecules, a metallic cantilever to measure pyroelectric surface potential (0.1 mm thick, 27 mm long, surface area of 22 by 25 mm), a transimpedance amplifier (TIA) to amplify the detected current due to generated ions/electrons, a temperature sensor to measure the crystal temperature, and a microcontroller to drive Peltier with PID (proportional-integral-derivative) controller using temperature sensor feedback. For cooling the crystal, negative Peltier power and a fan are used and data acquisition to record the temperature readings and ionization current data from the transimpedance amplifier.

Figure 42:
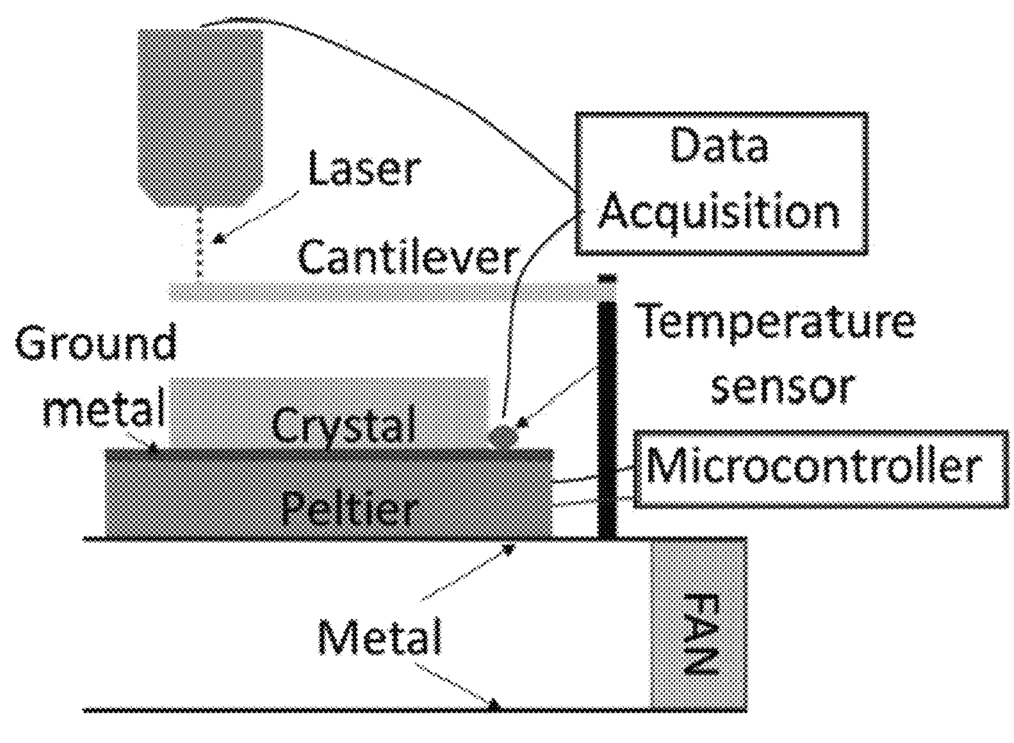
FIG. 42: Schematic of experimental setup to measure generate high voltage on the lithium niobate pyroelectric crystal surface during temperature cycling.
Figure 43:
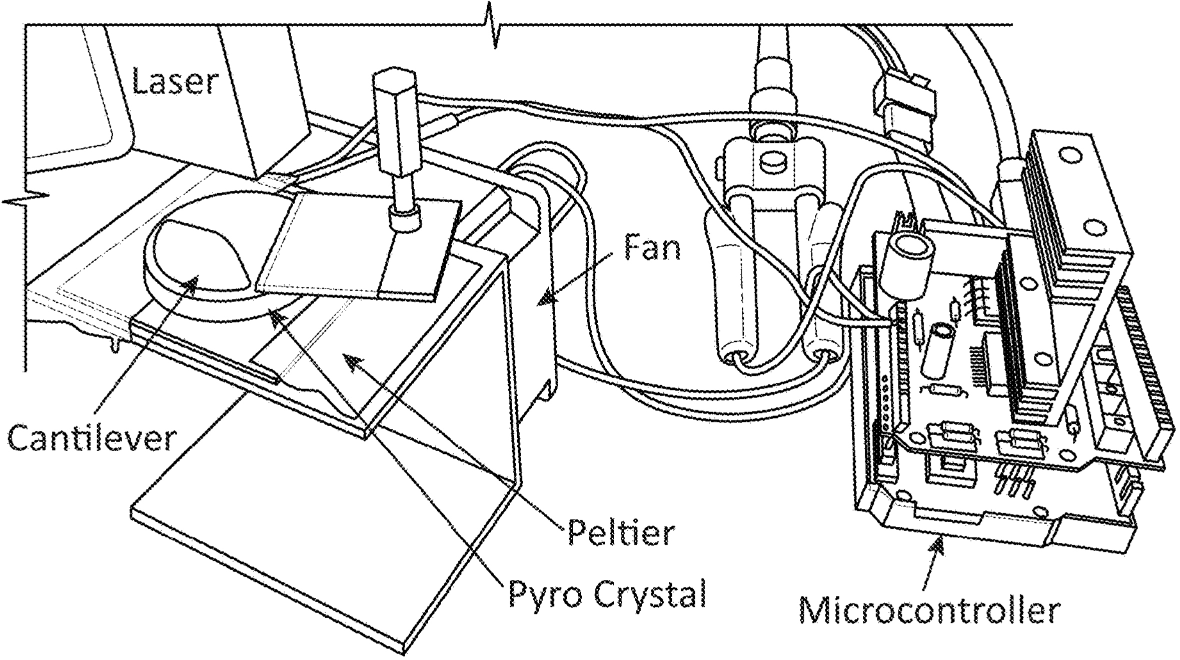
FIG. 43: Photograph of experimental setup to measure generate high voltage on the lithium niobate pyroelectric crystal surface during temperature cycling.

In the first experiment, pyroelectrically produced voltage was measured using the electrostatic cantilever (FIG. 42 and FIG. 43). A parallel plate configuration was used to measure the generated high voltage on the pyroelectric surface (Frank Horton. *Proc. Phys. Soc. London,* 1923, 36, 1). The cantilever displacement due to electrostatic attraction during thermal cycling was measured using a laser sensor (Waycon LAS-TM). The below equation was used to calculate the electrostatic voltage due to attraction between the charged surfaces.

$$V^2 = \frac{2(d_0 - z)^2 kz}{\varepsilon_0 A} \tag{2}$$

where V is the electrostatic voltage, do is the initial distance between the charged plats, k is the spring constant of the cantilever (rectangular cantilever), z is the change in the distance, A is the surface area of the charged cantilever, and $\varepsilon_0$ is the dielectric permittivity.

Figure 44:
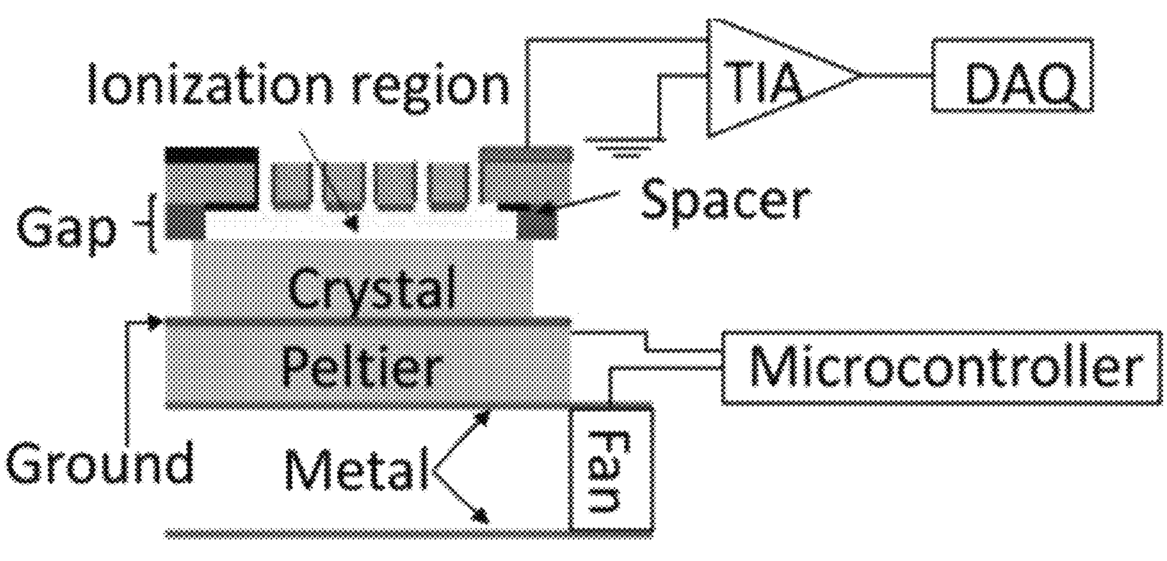
FIG. 44: Schematic of experimental setup used for the ionization of different volatile organic compounds vapor and air to measure generated high voltage on the lithium niobate pyroelectric crystal surface during temperature cycling.
Figure 45:
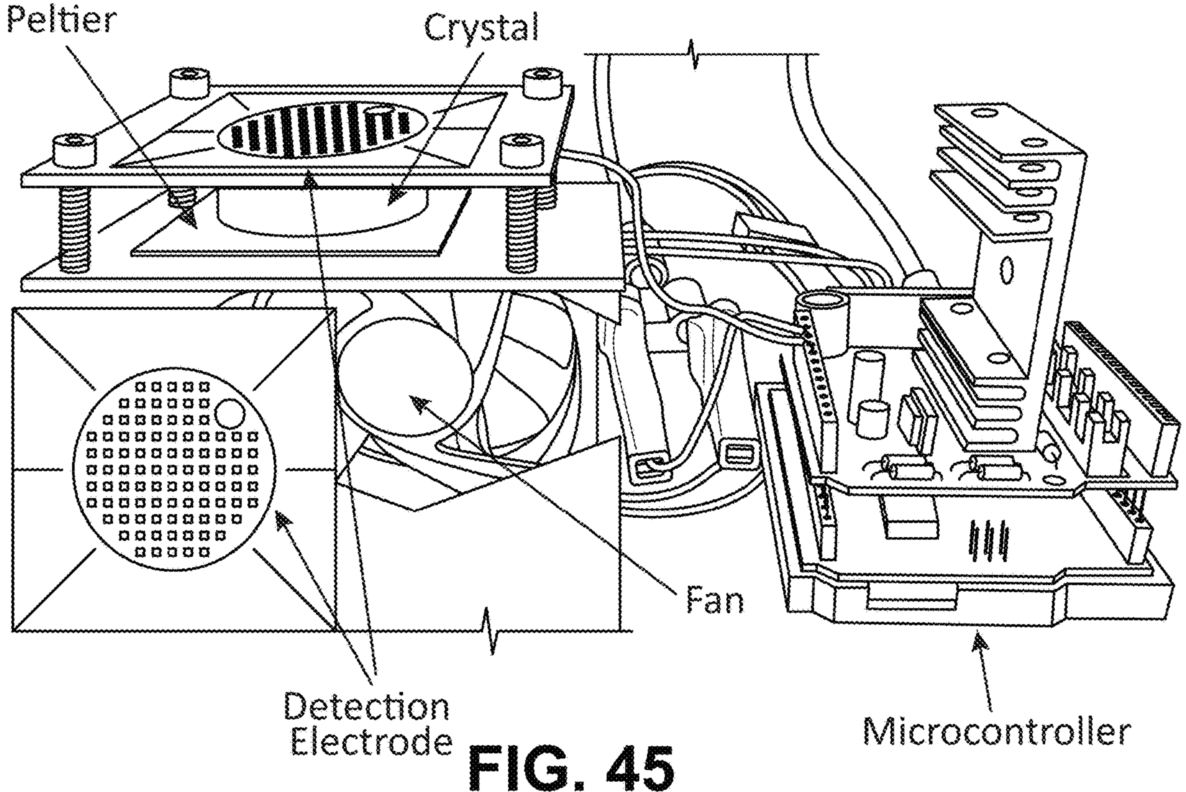
FIG. 45: Photograph of experimental setup used for the ionization of different volatile organic compounds vapor and air to measure generated high voltage on the lithium niobate pyroelectric crystal surface during temperature cycling. Inset is a schematic of the detection electrode.

In the second experiment, ionization of ambient air and different volatile organic compounds was measured for different electrode gaps and different temperature rates (FIG. 44 and FIG. 45).

In all the experiments, a thermal epoxy was used between all the thermally conductive paths for better thermal conduction. To acquire most ionization events, the transimpedance amplifier was used with a sampling rate of 50 kHz with a gain of 107 and data acquisition was sampled at a frequency of 100 kHz. The detection electrode was fabricated using a standard printed circuit board (PCB) fabrication process, the metal-filled vias (1000 μm diameter) were fabricated on the PCB with an outer circular metal ring with the positive bias (FIG. 45 inset (red color represents metal traces)).

Results and Discussion

Figure 46:
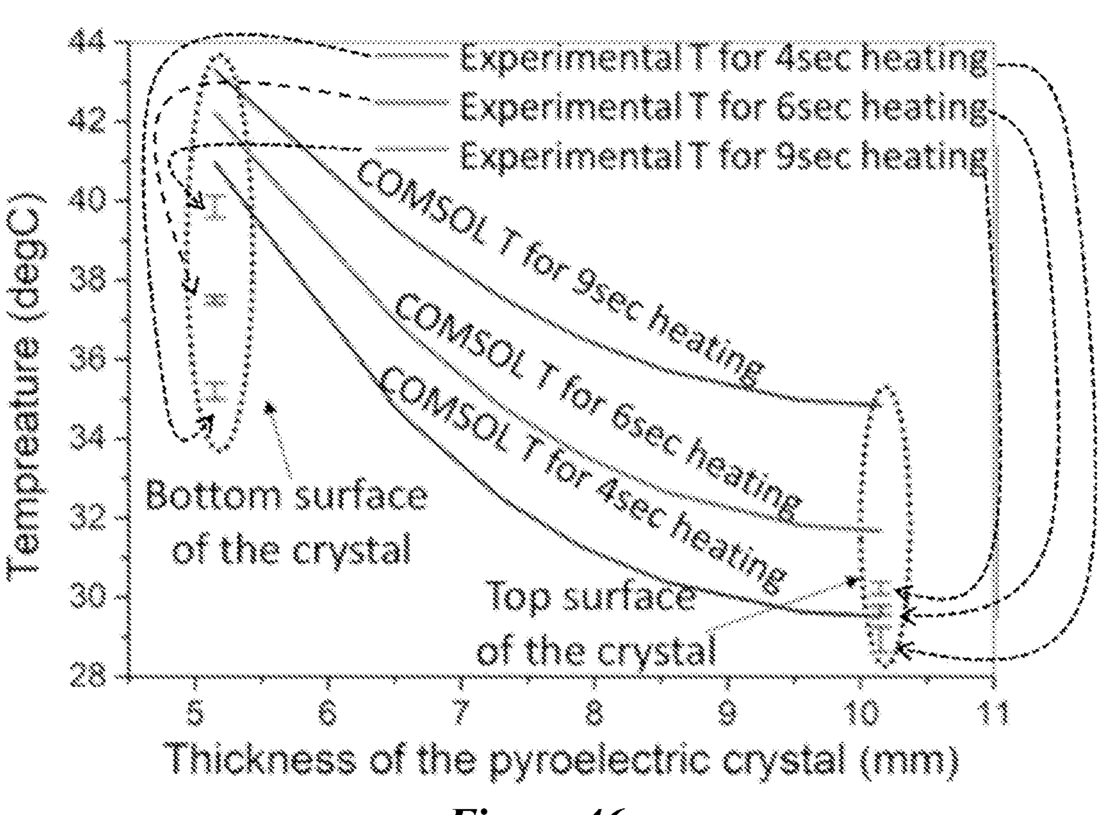
FIG. 46: COMSOL and experimental temperature (T) distribution across the pyroelectric crystal (5 mm thick crystal) for different heating time with constant power input.
Figure 47:
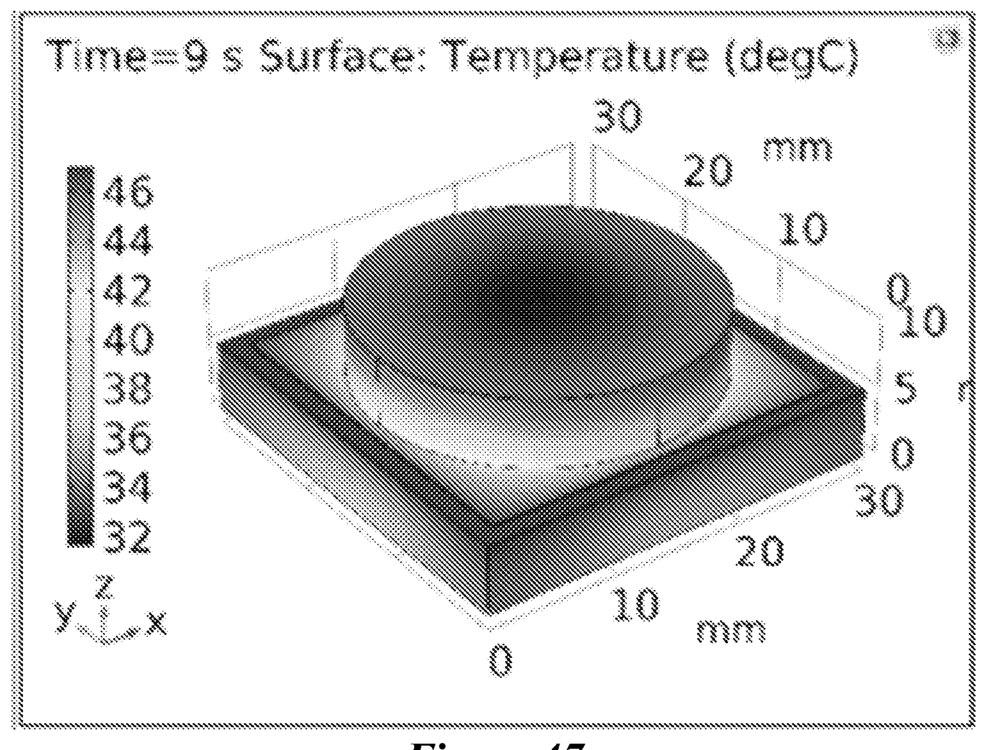
FIG. 47: COMSOL surface plot showing the temperature distribution for 9 sec heating time.

FIG. 46-FIG. 47 shows the measured and COMSOL simulated thermal distribution across the pyroelectric crystal. Deviation between simulated and experimentally measured temperatures on the surfaces of the crystal can be due to fact that there are more thermal dissipation paths from wires, extra metal, and temperature sensors for the latter.

Figure 48:
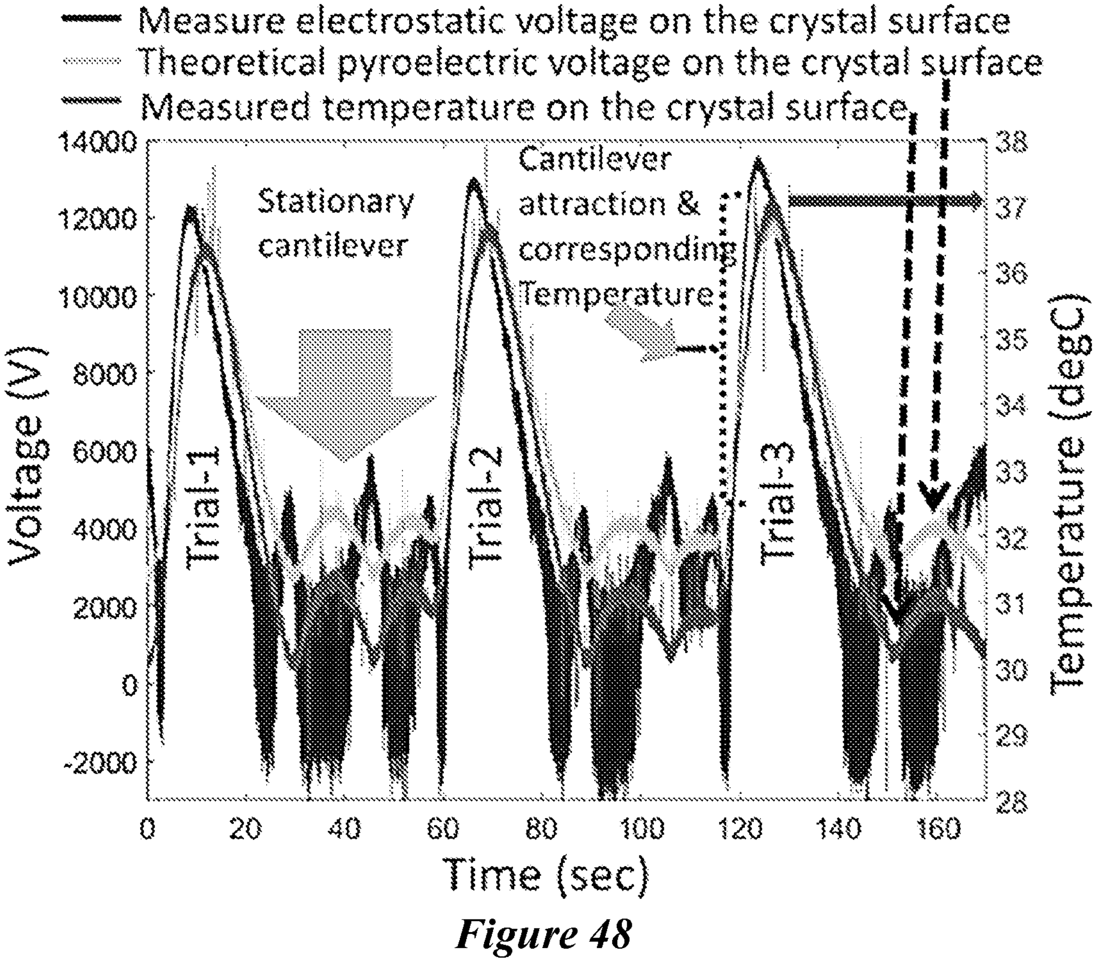
FIG. 48: Generated electrostatic voltage on the pyroelectric crystal (left axis) and corresponding temperature (right axis). The theoretical pyroelectric voltage (left axis) is calculated for the experimentally measured temperature using equation-1.

FIG. 48 shows the measured pyroelectric surface potential during the thermal cycling of the crystal. The cantilever attraction towards the pyroelectrically negatively charged surface corresponds to the temperature ramp given to the pyroelectric crystal. The measured cantilever displacement was converted into electrostatic voltage using Equation-2 and is plotted in FIG. 48. The theoretically calculated surface potential for the corresponding temperature (Equation 1) is also plotted with the experimentally measured electrostatic voltage in FIG. 48. The small deviation between the experimental and theoretical voltage can be due to uncounted thermal paths and rounded corners at the cantilever tip (theoretical calculation was carried assuming a square cantilever).

To measure the ionization of volatile organic compounds, ~50 μl of liquid analyte was dropped into the ionization region using a syringe. After dropping the liquid analyte into the ionization region, a wait time of 10 seconds for acetone and 20 seconds for isopropyl alcohol (IPA) and ethanol tests was counted to allow the drop to evaporate into the gas-phase before ramping the temperature on the crystal.

Figures 49A, 49B:
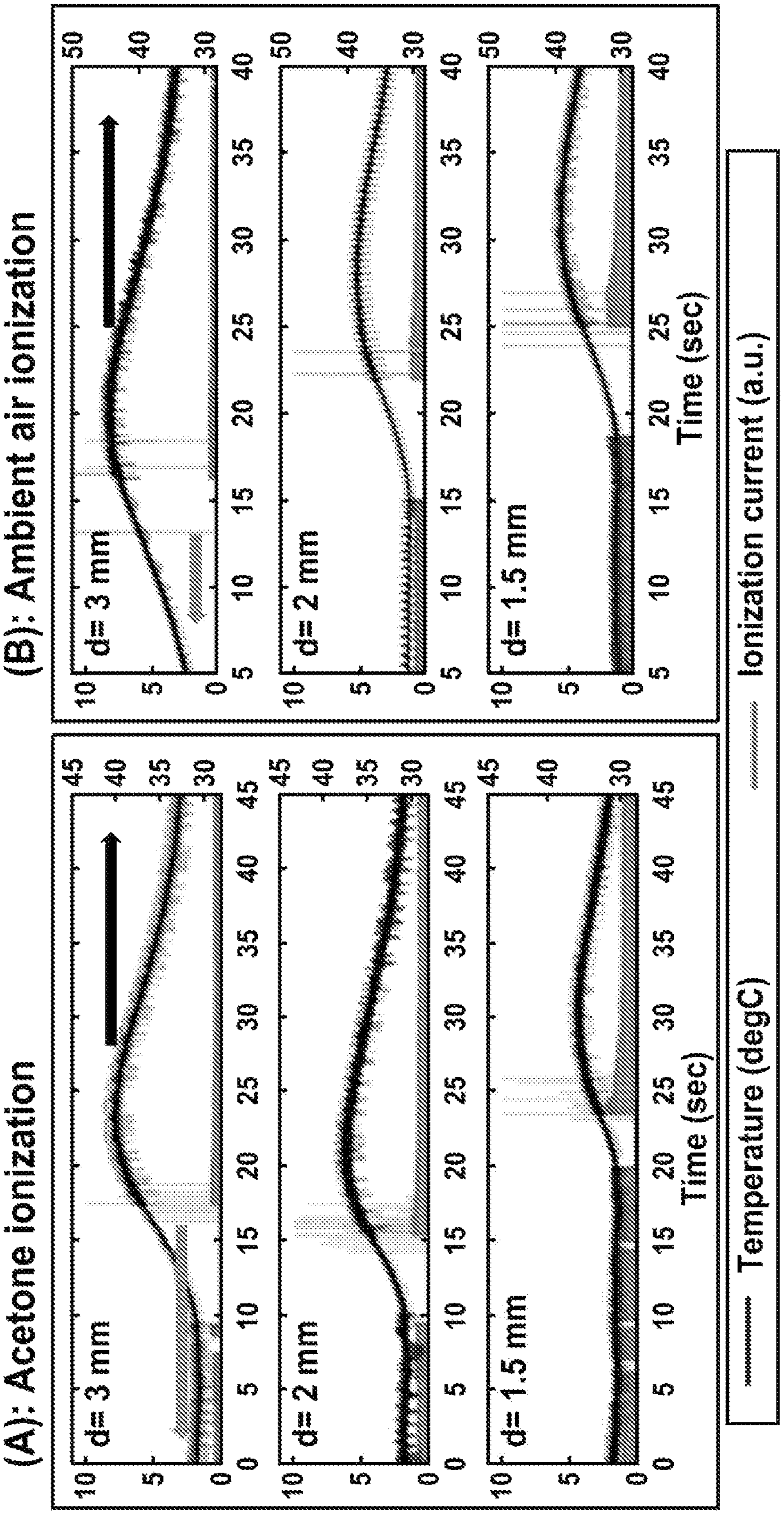
FIG. 49A-FIG. 49B: Ionization potential (left axis) for acetone and ambient air ionization for different temperature rate (right axis) and different electrode gap (top panels—3 mm, middle panels—2 mm, bottom panels—1.5 mm).

FIG. 49A shows the temperature ramp and corresponding acetone ionization for experiments with different gaps between the detection electrode and the pyroelectric ionization surface. Next, the experiments were carried out without any volatile organic compounds to ionize the ambient air. FIG. 49B shows the temperature ramp and corresponding ionization of the ambient air for the different gaps between the electrode and pyroelectric crystal. The temperature required to ionize acetone is much smaller than that required to ionize the ambient air for a fixed electrode gap. Hence, these results indicate the possibility of tuning ionization potential for ionizing and detecting different gases.

Further, the results in FIG. 49A and FIG. 49B indicate that the temperature required to ionize the surrounding molecules reduces as the gap between the detection electrode and the pyroelectric surface is reduced. This is because the reduced gap between the pyroelectric surface and the detection electrode enhances the electric field. Also, keeping the electrode close to the ionization surface can ensure that most of the ionized molecules are measured with the electrode at ambient pressure (without losing ionized molecules/electrons produced during ionization due to ambient air pressure scattering or recombination).

FIG. 49A and FIG. 49B show that the change in temperature on the pyroelectric current can correspond to the ionization events. Using a precision switched integrator transimpedance amplifier can help to integrate the generated ionization events during the temperature ramp and convert it into one single peak current (FIG. 38). This can simplify data analysis and gas differentiation. For this approach, an increase in the peak voltage can correspond to an increase in thermal rate. For different gas mixtures, the change in voltage behavior can be calibrated.

Figure 50:
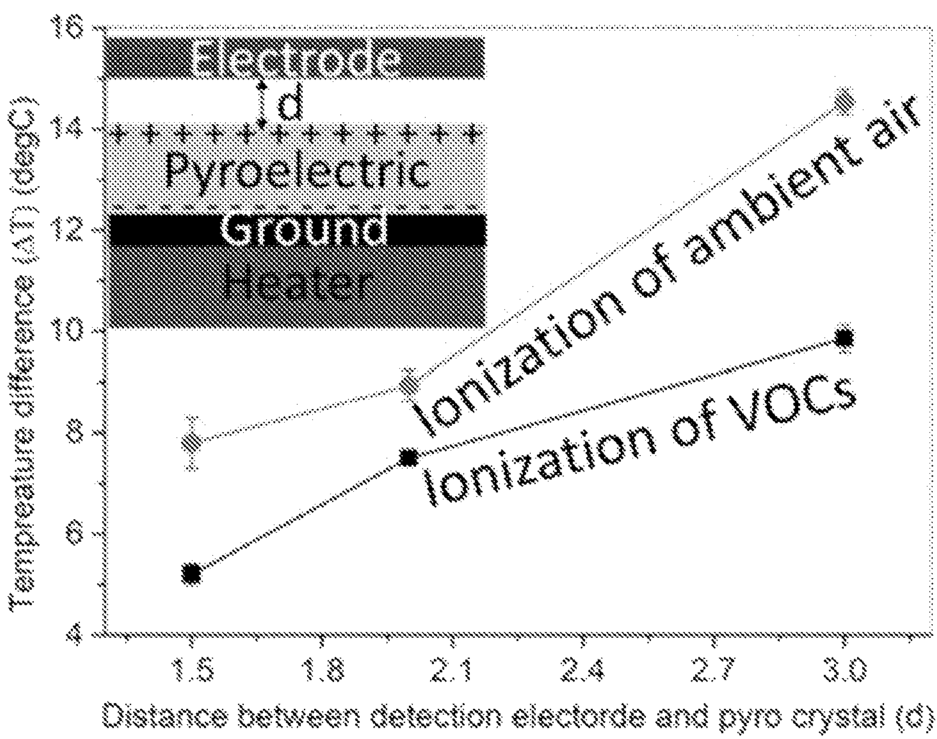
FIG. 50: Pyroelectric temperature difference required to ionize ambient air and volatile organic compounds (acetone/IPA/ethanol) at different gaps between the detection electrode and pyroelectric crystal surface.

Similar experiments were carried out for different volatile organic compounds such as acetone, isopropyl alcohol, and ethanol (FIG. 50). The results from these experiments indicated that the ionization temperature rate required to ionize these volatile organic compounds (acetone, isopropyl alcohol, and ethanol) is almost the same. This is consistent with FIG. 41A, which indicates that these volatile organic compounds have ionization potentials very close to each other. The ionization potential resolution required to detect the individual volatile organic compounds could be achieved by reducing the surface area and improving heating/cooling efficiency in the device. In the experiments described herein, the heating is directly proportional to the heating power; however, the cooling is slow due to the large thermal mass of the pyroelectric crystal and Peltier. Hence, a microfabricated heater and small pyroelectric crystal mounted with a silicon/metal electrode could provide monolithic integration of the system to achieve better selectivity between the volatile organic compounds and inorganic gases.

Summary and Future Work

The results discussed herein illustrate the possibility of ionization potential tunability to enable a multi-gas detection platform. Pyroelectrically generated voltage and the emitted electrons from the polarized surface provided the ionization energy for molecular detection. The obtained results for varying temperature and electrode gap between the detection electrode and the polarized surface showed a promising path forward in multi-gas detection with good selectivity and sensitivity. Further, the demonstrated device concept can be monolithically integrated using commercially available silicon micromachining and wafer bonding techniques. Hence, the overall device cost and operational power can be reduced, opening up opportunities for distributed gas sensors in IOT and IIOT application.

Example 2

Different molecules have different ionization energies. Commercially available photoionization detectors (PIDs) emit light to ionize molecules. There are four types of lamps available, each with a different and fixed ionization energy. When using a lamp of a fixed ionization energy, (E_lamp) all the molecules that have ionization energy lower than E_lamp will be ionized. In this configuration, detector provides a signal proportional to the concentration of all those molecules, therefore there is no information on the molecules themselves.

Described herein are gas-sensing platforms that allows measurement of several gases and volatile organic compounds using a miniature low-cost sensor. The devices described herein are ionization potential tunable pyroelectric ambient pressure multi-gas detection platforms. The devices described herein allows tuning, or sweeping, of the ionization potential, and therefore possibility of measuring different gases.

The principle is based on gas ionization, but unlike commercially available photoionization detectors (PIDs) that can only provide total volatile organic compound information, the ionization potential can be tuned/swept in the devices described herein, and therefore provide selectivity of detection. Tuning the ionization potential allows gradual ionization of different gases, therefore potentially enabling gas identification. It opens up significant opportunities for improving state-of-the-art low-cost gas sensing, and developing miniature sensors for applications in air quality, environmental monitoring, toxic gas detection, and consumer-related products.

The tunable ionization potential is produced using Lithium niobate pyroelectric crystal by controlling its heating temperature rate. The ionization potential generated from pyroelectrically emitted electrons can be tuned with the heating rate and gap controlled electric field distribution between the detection electrode and pyroelectrically charged surface. The lithium niobate pyroelectric ionization source was established by integrating a Peltier-based heating system and a fabricated ionization detection electrode.

Currently available small and low-costs detectors cannot measure multiple gases; they can either measure a single gas or measure a total gas concentration.

The devices and methods described herein have the ability to measure several gases and/or provide information on the type of gas, which is/are of industrially important. The devices and methods described herein have the ability to measure several gases in a small and low-cost package. The tunability of the ionization potential allows determination of the type and nature of the gases.

The devices and methods described herein allow for multi-gas detection under ambient conditions without the use of pumps or carrier gases. The devices described herein can be miniature, low-cost, CMOS compatible, and can be battery operated. Further work can include microfabrication using CMOS processes to make the sensors very small, potentially small to fit inside a mobile phone, a wearable device. CMOS will also further reduce the price of the devices.

The devices described herein can be used in a variety of applications, such as, for example, in wearables, military, air quality, industrial plants for gas leak detection, and medical applications.

Example 3

Figure 52:
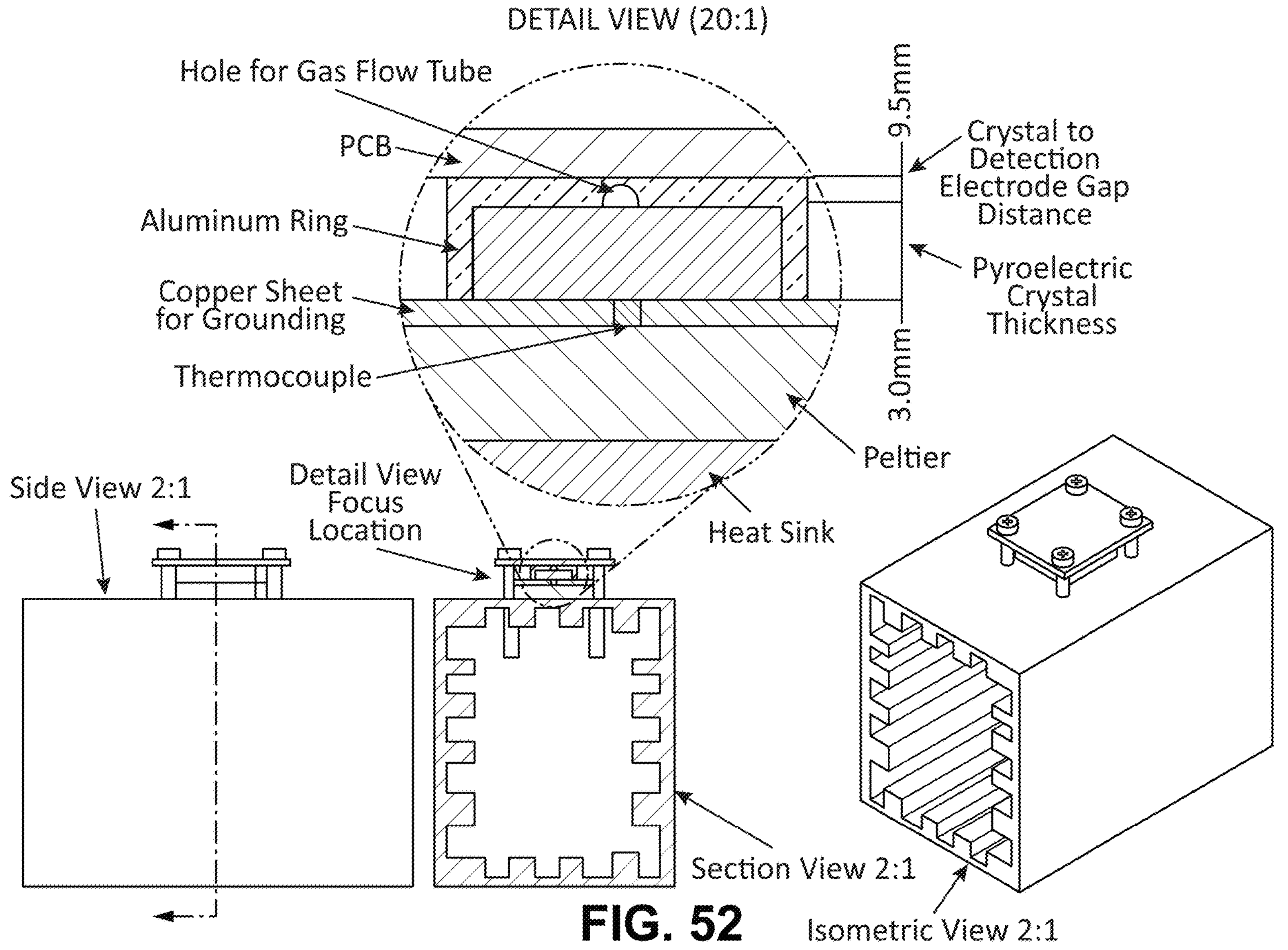
FIG. 52 is a schematic view of an example device as disclosed herein according to one implementation. Gas ionization occurs in the gap between the crystal and the PCB.
Figure 53:
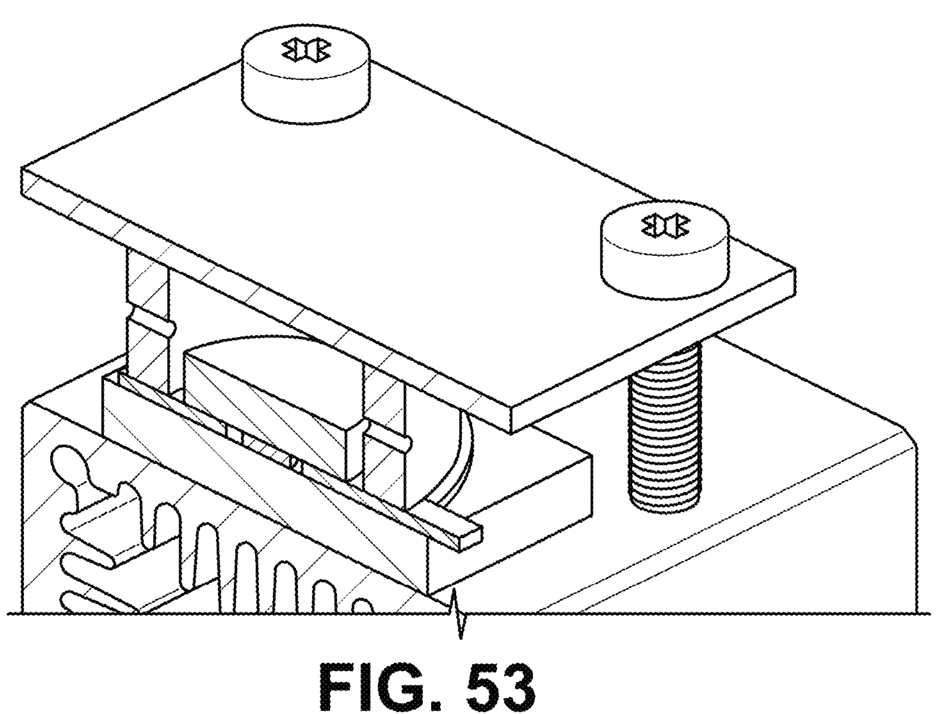
FIG. 53 is an isometric section view of the example device shown in FIG. 52.
Figure 54:
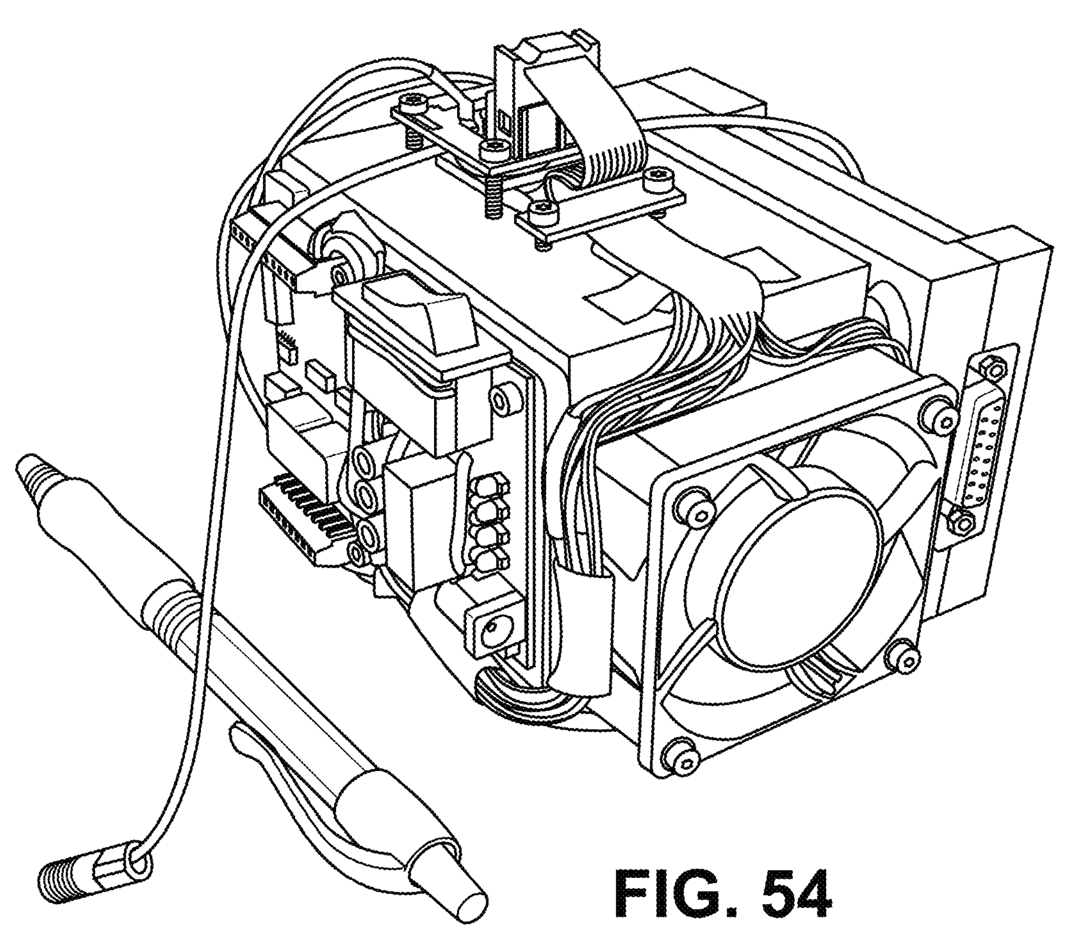
FIG. 54 is a photograph of a prototype of an example device as disclosed herein according to one implementation (pen in photograph is included for scale).

FIG. 52 is a schematic view of an example device as disclosed herein according to one implementation. Gas ionization occurs in the gap between the crystal and the PCB. FIG. 53 is an isometric section view of the example device shown in FIG. 52. FIG. 54 is a photograph of a prototype of an example device as disclosed herein according to one implementation (pen in photograph is included for scale).

Figure 55:
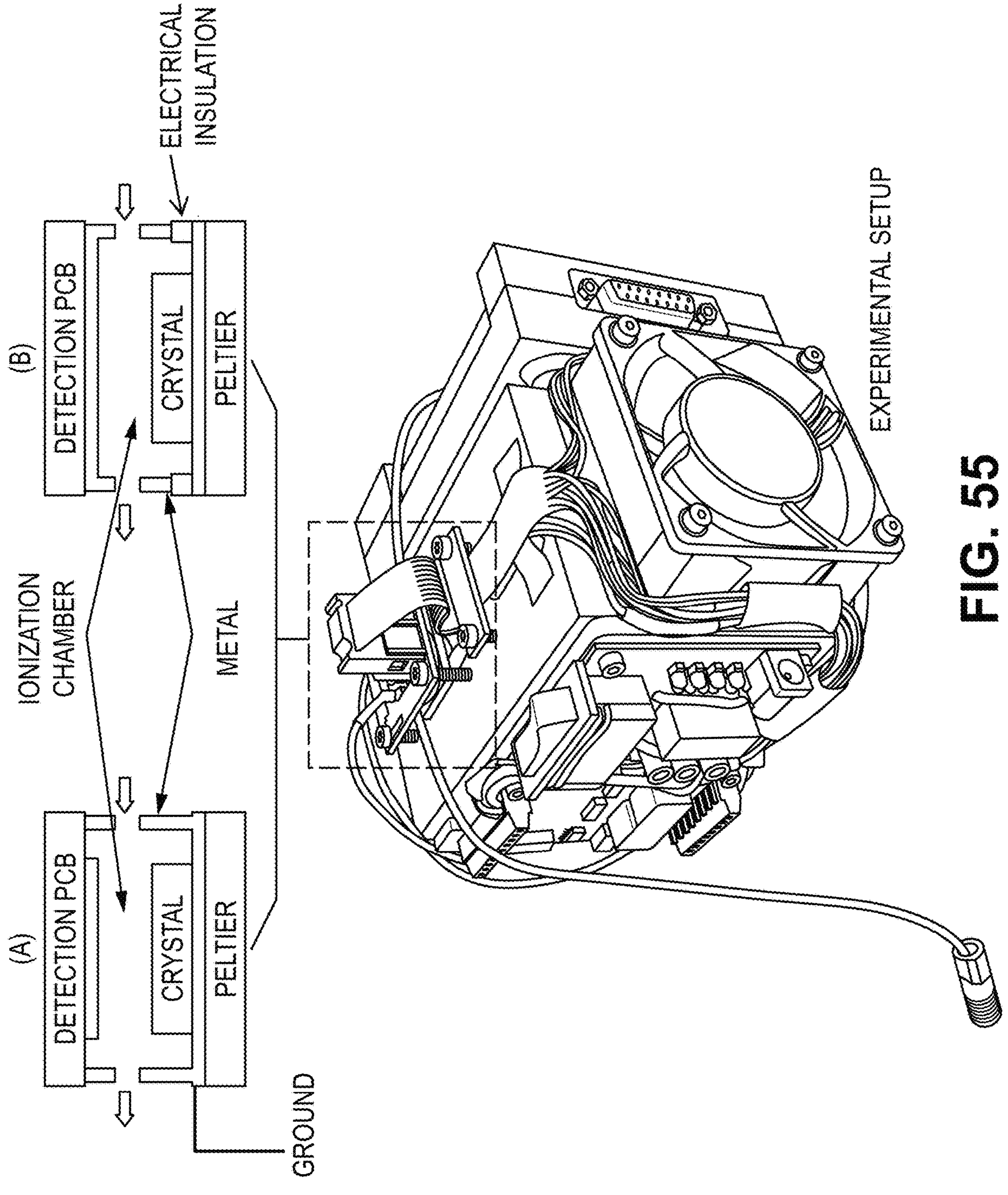
FIG. 55 is a schematic view of example devices as disclosed herein according to one implementation.

For the detection of ionized molecules in the ionization chamber, two experimental variants have been studied, as shown in FIG. 55. Schematic (A) in FIG. 55 represents the gas ionization chamber with a metallic structure around the ionization chamber which is connected to the ground potential. In schematic (B) in FIG. 55, the metallic structure around the ionization chamber is connected to the detection electrode via PCB and electrical insulation is used between the ground electrode and the metallic ionization chamber.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A gas detector device comprising:

a temperature control layer;

a grounded electrode disposed on the temperature control layer, wherein the grounded electrode is thermally conductive and is in thermal contact with the temperature control layer;

a pyroelectric layer comprising a pyroelectric material, wherein the pyroelectric layer is disposed on the grounded electrode such that the grounded electrode is disposed between the temperature control layer and the pyroelectric layer, wherein the pyroelectric layer is in thermal contact and electrical contact with the grounded electrode;

wherein the pyroelectric layer has a top surface and a bottom surface opposite and spaced apart from the top surface, and wherein the pyroelectric layer comprises a set of protrusions extending from the top surface; and a patterned detection electrode opposite and spaced apart from the pyroelectric layer by a distance, such that the patterned detection electrode and the top surface of the pyroelectric layer define an ionization zone between the patterned detection electrode and the top surface of the pyroelectric layer, wherein the patterned detection electrode comprises a set of cavities, a set of protrusions, a set of particles, or a combination thereof.

2. The gas detector device of claim 1, wherein the temperature control layer comprises a metallic resistive heating or cooling material, a ceramic heating or cooling material, a thermoelectric material, an induction heating or cooling material, an optical heating or cooling material, or a combination thereof.

3. The gas detector device of claim 1, wherein the pyroelectric material comprises lithium niobate ($LiNbO_3$), barium titanate ($BaTO_3$), lithium tantalate ($LiTaO_3$), lead zirconate titanate (PZT), cesium nitrate ($CsNO_3$), tourmaline, aluminum nitride (AlN), scandium doped aluminum nitride (ScAlN), potassium-sodium niobate (KNN), and combinations thereof.

4. The gas detector device of claim 1, wherein the set of protrusions comprises a plurality of protrusions arranged in an ordered array on the top surface of the pyroelectric layer.

5. The gas detector device of claim 1, wherein:

the set of protrusions extending from the top surface of the pyroelectric layer each has a longitudinal axis, a first surface, and a second surface opposite and axially spaced apart from the first surface, each of the set of protrusions has a cross-sectional shape in a plane perpendicular to the longitudinal axis, the cross-sectional shape of each of the set of protrusions independently being substantially circular, semicircular, ovate, ovoid, elliptic, triangular, rectangular, or polygonal, and wherein:

the longitudinal axis of the set of protrusions extending from the top surface of the pyroelectric layer are each substantially parallel to the top surface of the pyroelectric layer; or the first surface of each of the set of protrusions is planar and the longitudinal axis of each of the set of protrusions is substantially perpendicular to the top surface, such that each of the set of protrusions extends from the first surface at the top surface of the pyroelectric layer along the longitudinal axis to the second surface, wherein the second surface is planar or non-planar.

6. The gas detector device of claim 1, wherein the patterned detection electrode has a top surface and a bottom surface opposite and spaced apart from the top surface, and wherein the patterned detection electrode comprises a set of cavities, wherein each of the cavities perforates the patterned detection electrode from the top surface to the bottom surface.

7. The gas detector device of claim 6, wherein the set of cavities comprises a plurality of cavities arranged in an ordered array.

8. The gas detector device of claim 6, wherein each of the set of cavities has a longitudinal axis and a cross-sectional shape in a plane perpendicular to the longitudinal axis, wherein the cross-sectional shape of each of the set of cavities is independently substantially circular, ovate, ovoid, elliptic, triangular, rectangular, or polygonal, and wherein the longitudinal axis of each of the set of cavities is substantially parallel to each other and substantially perpendicular to the bottom surface of the patterned detection electrode.

9. The gas detector device of claim 1, wherein the patterned detection electrode has a top surface and a bottom surface opposite and spaced apart from the top surface, and wherein the patterned detection electrode comprises a set of protrusions, wherein each protrusion extends from the bottom surface of the patterned detection electrode.

10. The gas detector device of claim 9, wherein the set of protrusions extending from the bottom surface of the patterned detection electrode comprises a plurality of protrusions arranged in an ordered array.

11. The gas detector device of claim 9, wherein:

the set of protrusions extending from the bottom surface of the patterned detection electrode each has a longitudinal axis, a first surface, and a second surface opposite and axially spaced apart from the first surface, each of the set of protrusions has a cross-sectional shape in a plane perpendicular to the longitudinal axis, the cross-sectional shape of each of the set of protrusions independently being substantially circular, semicircular, ovate, ovoid, elliptic, triangular, rectangular, or polygonal, and wherein:

the longitudinal axis of the set of protrusions extending from the bottom surface of the patterned detection electrode are each substantially parallel to the bottom surface of the patterned detection electrode; or the first surface of each of the set of protrusions is planar and the longitudinal axis of each of the set of protrusions is substantially perpendicular to the bottom surface, such that each of the set of protrusions extends from the first surface at the bottom surface of the patterned detection electrode along the longitudinal axis to the second surface, wherein the second surface is planar or non-planar.

12. The gas detector device of claim 1, wherein the patterned detection electrode has a top surface and a bottom surface opposite and spaced apart from the top surface, and wherein the patterned detection electrode comprises a set of particles disposed on the bottom surface of the patterned detection electrode.

13. The gas detector device of claim 1, wherein the distance is from 1 nm to 10 mm.

14. The gas detector device of claim 1, wherein the distance is adjustable and the device further comprises a means for a means for controlling and/or adjusting the distance.

15. The gas detector device of claim 1, wherein the device further comprises:

a first substrate, wherein the temperature control layer is disposed on the first substrate, a second substrate, and a fluid flow control device, wherein the second substrate is disposed opposite and spaced apart from the first substrate and the fluid flow control device is disposed between the first substrate and the second substrate, and wherein the fluid flow control device is configured to control the flow of a fluid proximate to the first substrate to control dissipation of heat from temperature control layer.

16. A method of use of the device of claim 1, the method comprising using the gas detector devices for air quality monitoring, environmental monitoring, toxic gas detection, exhaled breath analysis, chemical process monitoring, monitoring of gases in pipes, monitoring inside reactors, monitoring inside fridge/oven/and other consumer appliances, monitoring inside a subject's body, or a combination thereof.

17. A gas detection method for distinguishing a first gas component and a second gas component, the method comprising:

introducing a gas into a gas detector device, the gas detector device comprising:

a temperature control layer;

a grounded electrode disposed on the temperature control layer, wherein the grounded electrode is thermally conductive and is in thermal contact with the temperature control layer;

a pyroelectric layer comprising a pyroelectric material, wherein the pyroelectric layer is disposed on the grounded electrode such that the grounded electrode is disposed between the temperature control layer and the pyroelectric layer, wherein the pyroelectric layer is in thermal contact and electrical contact with the grounded electrode;

wherein the pyroelectric layer has a top surface and a bottom surface opposite and spaced apart from the top surface, and wherein the pyroelectric layer comprises a set of protrusions extending from the top surface; and a detection electrode opposite and spaced apart from the pyroelectric layer by a distance, such that the detection electrode and the top surface of the pyroelectric layer define an ionization zone between the detection electrode and the top surface of the pyroelectric layer;

the method comprising:

introducing the gas into the ionization zone of the gas detector device while heating or cooling the temperature control layer to a first temperature at a first rate, which induces a first potential in the pyroelectric layer via the pyroelectric effect;

wherein the gas comprises the first gas component and the second gas component;

wherein the first gas component has a first ionization potential and the second gas component has a second ionization potential;

wherein the second ionization potential is greater than the first ionization potential;

wherein the first potential is greater than or equal to the first ionization potential and less than the second ionization potential;

thereby ionizing the first gas component to produce a first ion; and electrically detecting the first ion via the detection electrode;

subsequently, heating or cooling the temperature control layer to a second temperature at a second rate, which induces a second potential in the pyroelectric layer via the pyroelectric effect;

wherein the second potential is greater than or equal to the second ionization potential;

thereby ionizing the first gas component to produce the first ion and ionizing the second gas component to produce a second ion; and electrically detecting the first ion and the second ion via the detection electrode.

* * * * *